US012649899B2

(12) United States Patent
Lim et al.

(10) Patent No.: US 12,649,899 B2
(45) Date of Patent: Jun. 9, 2026

(54) GAS FLOW REGULATION FOR A CELL CULTURE INCUBATOR

(71) Applicant: XCELL BIOSCIENCES, INC., San Francisco, CA (US)

(72) Inventors: James Lim, Oakland, CA (US); Luke Cassereau, Emeryville, CA (US)

(73) Assignee: XCELL BIOSCIENCES, INC., San Francisco, CA (US)

( * ) Notice: Subject to any disclaimer, the term of this patent is extended or adjusted under 35 U.S.C. 154(b) by 1234 days.

(21) Appl. No.: 17/408,301

(22) Filed: Aug. 20, 2021

(65) Prior Publication Data

US 2021/0388306 A1 Dec. 16, 2021

Related U.S. Application Data

(63) Continuation of application No. 17/335,353, filed on Jun. 1, 2021, which is a continuation of application
(Continued)

(51) Int. Cl.
C12M 1/00 (2006.01)
C12M 1/34 (2006.01)
C12M 1/36 (2006.01)
(52) U.S. Cl.
CPC ............ *C12M 41/14* (2013.01); *C12M 41/34* (2013.01); *C12M 41/40* (2013.01); *C12M 41/48* (2013.01)
(58) Field of Classification Search
CPC ...... C12M 41/40; C12M 41/34; C12M 41/48; C12M 41/14
See application file for complete search history.

(56) References Cited

U.S. PATENT DOCUMENTS 3,873,423 A 3/1975 Munder et al.
3,941,662 A 3/1976 Munder et al.
(Continued)

FOREIGN PATENT DOCUMENTS

CN 1737106 A 2/2006
CN 202279825 U 6/2012
(Continued)

OTHER PUBLICATIONS

Ameri, et al.: Circulating tumour cells demonstrate an altered response to hypoxia and an aggressive phenotype. Br J Cancer. Feb. 2, 2010;102(3):561-9. doi: 10.1038/sj.bjc.6605491. Epub Jan. 5, 2010.
(Continued)

*Primary Examiner* — Shogo Sasaki
(74) *Attorney, Agent, or Firm* — Snell & Wilmer, L.L.P.; April Wurster

(57) ABSTRACT

Embodiments of the invention relate to a cell culture incubator having a gas flow regulation system that exerts control over atmospheric parameters within the incubator. Particular embodiments include an enclosed environmental chamber and a control unit operably linked thereto, the control unit having an oxygen module and a pressure module. Control unit embodiments, by way of these modules, are configured to regulate both oxygen partial pressure and total gas pressure within the enclosed environmental chamber. Embodiments of the control unit are adapted (a) to provide instructions to the oxygen module to regulate an oxygen level to an instructed hypoxic oxygen level and (b) to provide instructions to the pressure module to regulate total gas pressure to an instructed positive pressure level. The regulation of oxygen to the instructed hypoxic level prevails despite an oxygen partial pressure-increasing effect of the positive
(Continued)

pressure condition associated with the instructed positive pressure level.

27 Claims, 25 Drawing Sheets

Related U.S. Application Data

No. 17/077,222, filed on Oct. 22, 2020, now abandoned, which is a continuation of application No. 15/789,464, filed on Oct. 20, 2017, now abandoned, which is a continuation-in-part of application No. 15/566,337, filed as application No. PCT/US2016/027881 on Apr. 15, 2016, now abandoned.

(60) Provisional application No. 62/149,268, filed on Apr. 17, 2015.

(56) References Cited

U.S. PATENT DOCUMENTS

| | | | |
|---|---|---|---|
| 4,336,329 A | 6/1982 | Hesse et al. | |
| 5,330,915 A | 7/1994 | Wilson et al. | |
| 5,728,581 A | 3/1998 | Schwartz et al. | |
| 5,882,918 A | 3/1999 | Goffe et al. | |
| 5,922,687 A | 7/1999 | Mann et al. | |
| 5,958,763 A | 9/1999 | Goffe et al. | |
| 6,184,035 B1 | 2/2001 | Csete et al. | |
| 6,197,575 B1 | 3/2001 | Griffith et al. | |
| 6,255,495 B1 | 7/2001 | Yang et al. | |
| 6,322,989 B1 | 11/2001 | Cohen et al. | |
| 6,365,362 B1 | 4/2002 | Terstappen et al. | |
| 6,399,375 B2 | 6/2002 | Vajta et al. | |
| 6,589,728 B2 | 7/2003 | Csete et al. | |
| 6,656,683 B1 | 12/2003 | Reuben et al. | |
| 6,759,242 B1 | 7/2004 | Csete et al. | |
| 7,259,149 B2 | 8/2007 | Hiraoka et al. | |
| 7,282,350 B2 | 10/2007 | Rao et al. | |
| 7,367,550 B2 | 5/2008 | Lee et al. | |
| 7,476,541 B1 | 1/2009 | Dutra et al. | |
| 7,687,241 B2 | 3/2010 | Chen et al. | |
| 7,785,810 B2 | 8/2010 | Chen et al. | |
| 7,816,138 B2 | 10/2010 | Dutra et al. | |
| 7,819,934 B2 | 10/2010 | Galliher et al. | |
| 7,863,012 B2 | 1/2011 | Rao et al. | |
| 8,039,213 B2 | 10/2011 | Kornblith et al. | |
| 8,071,395 B2 | 12/2011 | Davis et al. | |
| 8,101,409 B2 | 1/2012 | Chiu et al. | |
| 8,131,053 B2 | 3/2012 | Ortyn et al. | |
| 8,137,912 B2 | 3/2012 | Kapur et al. | |
| 8,288,116 B2 | 10/2012 | Chen et al. | |
| 8,420,394 B2 | 4/2013 | Lin et al. | |
| 8,445,225 B2 | 5/2013 | Kuhn et al. | |
| 8,501,397 B2 | 8/2013 | Wise et al. | |
| 8,563,304 B2 | 10/2013 | Young et al. | |
| 8,709,793 B2 | 4/2014 | Taboas et al. | |
| 8,778,681 B2 | 7/2014 | Sano et al. | |
| 8,790,638 B2 | 7/2014 | Tankovich et al. | |
| 8,906,686 B2 | 12/2014 | Mizuno et al. | |
| 9,005,607 B2 | 4/2015 | Kumar et al. | |
| 9,029,147 B2 | 5/2015 | Colton et al. | |
| 9,138,460 B2 | 9/2015 | Sevrain et al. | |
| 9,279,105 B2 | 3/2016 | Wise et al. | |
| 9,303,244 B1 | 4/2016 | Kasra et al. | |
| 9,388,381 B2 | 7/2016 | Colton et al. | |
| 9,447,378 B2 | 9/2016 | Colton et al. | |
| 9,580,687 B2 | 2/2017 | Yang et al. | |
| 9,677,050 B2 | 6/2017 | Young et al. | |
| 9,857,360 B2 | 1/2018 | Lim et al. | |
| 2001/0021529 A1* | 9/2001 | Takagi | C12M 21/08 |
| | | | 435/395 |
| 2001/0034061 A1 | 10/2001 | Csete et al. | |
| 2002/0009803 A1 | 1/2002 | Vajta et al. | |
| 2002/0047311 A1 | 4/2002 | Hugh et al. | |

| | | | |
|---|---|---|---|
| 2002/0146825 A1 | 10/2002 | Uhler | |
| 2003/0092178 A1 | 5/2003 | Yerden | |
| 2004/0152188 A1 | 8/2004 | Yamamoto et al. | |
| 2004/0224401 A1 | 11/2004 | Ludwig et al. | |
| 2005/0079557 A1 | 4/2005 | Vendrell et al. | |
| 2005/0101008 A1 | 5/2005 | Diresta et al. | |
| 2005/0155099 A1 | 7/2005 | Rothenberg et al. | |
| 2005/0158701 A1* | 7/2005 | West | G05D 21/02 |
| | | | 435/286.1 |
| 2005/0181463 A1 | 8/2005 | Rao et al. | |
| 2005/0244843 A1 | 11/2005 | Chen et al. | |
| 2005/0260745 A1 | 11/2005 | Domansky et al. | |
| 2006/0094109 A1 | 5/2006 | Trainer et al. | |
| 2006/0275836 A1 | 12/2006 | Kirkpatrick et al. | |
| 2007/0184033 A1 | 8/2007 | Sevrain et al. | |
| 2007/0207538 A1* | 9/2007 | Amano | C12M 41/48 |
| | | | 702/19 |
| 2007/0264712 A1 | 11/2007 | Savant-Bhonsale et al. | |
| 2007/0298454 A1 | 12/2007 | Green et al. | |
| 2008/0176276 A1 | 7/2008 | Arai et al. | |
| 2008/0286862 A1 | 11/2008 | Ludwig et al. | |
| 2008/0305473 A1 | 12/2008 | Chowdary et al. | |
| 2009/0098641 A1 | 4/2009 | Grant et al. | |
| 2009/0105738 A1 | 4/2009 | Apperson et al. | |
| 2009/0317836 A1 | 12/2009 | Kuhn et al. | |
| 2010/0028915 A1 | 2/2010 | Gualberto et al. | |
| 2010/0104544 A1 | 4/2010 | Atala et al. | |
| 2010/0184219 A1 | 7/2010 | Forsyth et al. | |
| 2010/0216168 A1 | 8/2010 | Heinzman et al. | |
| 2010/0221833 A1 | 9/2010 | Chung et al. | |
| 2010/0233694 A1 | 9/2010 | Kopf-Sill et al. | |
| 2011/0020930 A1 | 1/2011 | Wise et al. | |
| 2011/0039338 A1 | 2/2011 | Yamanaka et al. | |
| 2011/0053152 A1 | 3/2011 | Goldkorn et al. | |
| 2011/0104718 A1 | 5/2011 | Rao et al. | |
| 2011/0129918 A1 | 6/2011 | Hung et al. | |
| 2011/0177597 A1 | 7/2011 | Menu et al. | |
| 2012/0015835 A1 | 1/2012 | Fuchs et al. | |
| 2012/0100538 A1 | 4/2012 | Mikolajczyk et al. | |
| 2012/0134965 A1 | 5/2012 | Kim et al. | |
| 2012/0141547 A1 | 6/2012 | Zhao et al. | |
| 2012/0213754 A1 | 8/2012 | Chapman et al. | |
| 2012/0280686 A1 | 11/2012 | White et al. | |
| 2013/0164848 A1 | 6/2013 | Munaka et al. | |
| 2013/0287743 A1 | 10/2013 | Colton et al. | |
| 2014/0099717 A1 | 4/2014 | Fraker et al. | |
| 2014/0120610 A1 | 5/2014 | Yamashita et al. | |
| 2014/0141499 A1 | 5/2014 | Nakajima et al. | |
| 2014/0142000 A1 | 5/2014 | Tung et al. | |
| 2014/0212895 A1 | 7/2014 | Lim et al. | |
| 2014/0273211 A1 | 9/2014 | Slukvin et al. | |
| 2014/0286910 A1 | 9/2014 | Tankovich et al. | |
| 2014/0287509 A1 | 9/2014 | Sharei et al. | |
| 2014/0370598 A1 | 12/2014 | Colton et al. | |
| 2015/0010517 A1 | 1/2015 | Chapman | |
| 2015/0017711 A1 | 1/2015 | Bennett et al. | |
| 2015/0023911 A1 | 1/2015 | Schilling et al. | |
| 2015/0110749 A1 | 4/2015 | Vacanti et al. | |
| 2015/0118755 A1 | 4/2015 | Jaenisch et al. | |
| 2015/0247112 A1 | 9/2015 | Orr et al. | |
| 2016/0113967 A1 | 4/2016 | Hedrick et al. | |
| 2016/0113968 A1 | 4/2016 | Hung | |
| 2016/0193605 A1 | 7/2016 | Sharei et al. | |
| 2016/0222353 A1 | 8/2016 | Yang et al. | |
| 2016/0244711 A1 | 8/2016 | Kiyama et al. | |
| 2016/0251620 A1 | 9/2016 | Gobbi | |
| 2016/0289635 A1 | 10/2016 | Sasai et al. | |
| 2017/0007677 A1 | 1/2017 | Ueda | |
| 2017/0009204 A1 | 1/2017 | Gerecht et al. | |
| 2017/0105984 A1 | 4/2017 | Saya et al. | |
| 2017/0121677 A1 | 5/2017 | Colton et al. | |
| 2017/0130198 A1 | 5/2017 | Tyvoll et al. | |
| 2017/0369904 A1 | 12/2017 | Lim et al. | |
| 2018/0066223 A1 | 3/2018 | Lim et al. | |
| 2018/0267025 A1 | 9/2018 | Lim | |

(56) References Cited

U.S. PATENT DOCUMENTS

FOREIGN PATENT DOCUMENTS

| EP | 1697391 B1 | 10/2011 |
| EP | 2948776 | 12/2015 |
| EP | 3283611 A1 | 2/2018 |
| JP | 2002530067 A | 9/2002 |
| JP | 2003325160 A | 11/2003 |
| JP | 2004242581 A | 9/2004 |
| JP | 2012508691 A | 4/2012 |
| WO | WO-9830676 A1 | 7/1998 |
| WO | WO-9921533 A2 | 5/1999 |
| WO | WO-2006108229 A1 | 10/2006 |
| WO | WO-2009007692 A2 | 1/2009 |
| WO | WO-2009035217 A1 | 3/2009 |
| WO | WO-2009083756 A1 | 7/2009 |
| WO | WO-2009135206 A1 | 11/2009 |
| WO | WO-2010056328 A1 | 5/2010 |
| WO | WO-2010058898 A1 | 5/2010 |
| WO | WO-2010099539 A1 | 9/2010 |
| WO | WO-2011006107 A1 | 1/2011 |
| WO | WO-2011113036 A2 | 9/2011 |
| WO | WO-2012065067 A2 | 5/2012 |
| WO | WO-2012168930 A2 | 12/2012 |
| WO | WO-2012168930 A3 | 4/2013 |
| WO | WO-2014117021 A2 | 7/2014 |
| WO | WO-2014117021 A3 | 10/2014 |
| WO | WO-2016064757 A1 | 4/2016 |
| WO | WO-2016070136 A1 | 5/2016 |
| WO | WO-2016077761 A1 | 5/2016 |
| WO | WO-2016115179 A1 | 7/2016 |
| WO | WO-2016168687 A1 | 10/2016 |

OTHER PUBLICATIONS

Atkuri, et al.: Importance of culturing primary lymphocytes at physiological oxygen levels. Proc Natl Acad Sci U S A. Mar. 13, 2007;104(11):4547-52. Epub Mar. 5, 2007.

Attard, et al.: Utilizing circulating tumor cells: challenges and pitfalls. Curr Opin Genet Dev. Feb. 2011;21(1):50-8. doi: 10.1016/j.gde.2010.10.010. Epub Nov. 26, 2010.

Bartlett, et al.: Isolation of a gene regulated by hydrostatic pressure in a deep-sea bacterium. Nature. Nov. 30, 1989;342(6249):572-4.

Basson, et al.: Effects of increased ambient pressure on colon cancer cell adhesion. J Cell Biochem. Apr. 2000;78(1):47-61.

Bichsel, et al.: Diagnostic microchip to assay 3D colony-growth potential of captured circulating tumor cells. Lab Chip. Jul. 7, 2012;12(13):2313-6. doi: 10.1039/c2c40130d. Epub May 8, 2012.

Biospherix: "OxyCycler C42", http://www.biospherix.com/pdf/cell%20Researc%20Literature_OxyCycler%20C42.pdf. Retrieved from the internet: http://www.biospherix.com/pdf/cell%20Researc%20Literature_OxyCycler%20C42.pdf. Retrieved on Oct. 30, 2018.

Biospherix: "ProOc C21", Biospherix, Retrieved from the internet: URL:https://www.biospherix.com/pdf/cel%20research%20literature_ProOx%20C21.pdf. Retrieved on Oct. 30, 2018.

Bondar, et al.: Monitoring of the Zeta Potential of Human Cells upon Reduction in Their Viability and Interaction with Polymers. Acta Naturae. 2012; 4:78-81.

Boucher, et al.: Microvascular pressure is the principal driving force for interstitial hypertension in solid tumors: implications for vascular collapse. Cancer Res. Sep. 15, 1992;52(18):5110-4.

Butcher et al.: A tense situation: forcing tumour progression, Nat Rev Cancer. Feb. 2009;9(2):108-122. doi: 10.1038/nrc2544.

Carey et al.: Mechanobiology of tumor invasion: engineering meets oncology, Crit Rev Oncol Hematol, Aug. 2012, 83(2):170-183.

Charnley, et al.: Integration column: microwell arrays for mammalian cell culture. Integr Biol (Camb). Dec. 2009;1(11-12):625-34. doi: 10.1039/b918172p. Epub Oct. 14, 2009.

Collins: ImageJ for microscopy. Biotechniques. Jul. 2007;43(1 Suppl):25-30.

Cristofanilli, et al.: Circulating tumor cells: a novel prognostic factor for newly diagnosed metastatic breast cancer. J Clin Oncol. Mar. 1, 2005;23(7):1420-30.

Cristofanilli, et al.: Circulating tumor cells, disease progression, and survival in metastatic breast cancer. N Engl J Med. Aug. 19, 2004;351(8):781-91.

De Giorgi, et al.: Circulating tumor cells and [18F]fluorodeoxyglucose positron emission tomography/computed tomography for outcome prediction in metastatic breast cancer. J Clin Oncol. Jul. 10, 2009;27(20):3303-11. doi: 10.1200/JCO.2008.19.4423. Epub May 18, 2009.

De Mattos-Arruda, et al.: Development of molecular biomarkers in individualized treatment of colorectal cancer. Clin Colorectal Cancer. Dec. 2011;10(4):279-89. doi: 10.1016/j.clcc.2011.03.030. Epub May 12, 2011.

Deguine, et al.: Intravital imaging reveals distinct dynamics for natural killer and CD8(+) T cells during tumor regression. Immunity. Oct. 29, 2010;33(4):632-44. doi: 10.1016/j.immuni.2010.09.016. Epub Oct. 14, 2010.

Deng, et al.: Enrichment with anti-cytokeratin alone or combined with anti-EpCAM antibodies significantly increases the sensitivity for circulating tumor cell detection in metastatic breast cancer patients. Breast Cancer Res. 2008;10(4):R69. doi: 10.1186/bcr2131. Epub Aug. 7, 2008.

Diamandis, et al.: Circulating cancer cells and their clinical applications. Clin Chem. Nov. 2011;57(11):1478-84. doi: 10.1373/clinchem.2011.166678. Epub May 17, 2011.

Dyugovskaya, et al., Bax/Mcl-1 balance affects neutrophil survival in intermittent hypoxia and obstructive sleep apnea: effects of p38MAPK and ERK1/2 signaling. Journal of translational medicine, 2012;10:211.

Edelstein, et al.: Computer Control of Microscopes Using UNIT 14.20 μManager. Current Protocols in Molecular Biology. 2010; 14.20.1-14.20.17.

EP16780896.3 Extended European Search Report dated Nov. 23, 2018.

European search report and opinion dated Jul. 25, 2016 for EP Application No. 14743533.3.

Flores, et al. Improving the yield of circulating tumour cells facilitates molecular characterisation and recognition of discordant HER2 amplification in breast cancer. Br J Cancer. May 11, 2010;102(10):1495-502. doi: 10.1038/sj.bjc.6605676.

Gao, et al.: Organoid cultures derived from patients with advanced prostate cancer. Cell. Sep. 25, 2014;159(1):176-87. doi: 10.1016/j.cell.2014.08.016. Epub Sep. 4, 2014.

Generali, et al.: Molecular oncology and the neoadjuvant setting: the perfect blend for treatment personalization and clinical trial design. J Natl Cancer Inst Monogr. 2011;2011(43):67-70. doi: 10.1093/jncimonographs/lgr029.

Gorges, et al.: Circulating tumour cells escape from EpCAM-based detection due to epithelial-to-mesenchymal transition. BMC Cancer. May 16, 2012;12:178. doi: 10.1186/1471-2407-12-178.

Guilak, et al.: Control of stem cell fate by physical interactions with the extracellular matrix. Cell Stem Cell. Jul. 2, 2009;5(1):17-26. doi: 10.1016/j.stem.2009.06.016.

Haltiwanger. The Electrical Properties of Cancer Cells. 2010.

Hayes, et al.: Circulating tumor cells at each follow-up time point during therapy of metastatic breast cancer patients predict progression-free and overall survival. Clin Cancer Res. Jul. 15, 2006;12(14 Pt 1):4218-24.

Heldin, et al.: High interstitial fluid pressure—an obstacle in cancer therapy. Nat Rev Cancer. Oct. 2004;4(10):806-13.

Hope, et al.: Acute myeloid leukemia originates from a hierarchy of leukemic stem cell classes that differ in self-renewal capacity. Nat Immunol. Jul. 2004;5(7):738-43. Epub May 30, 2004.

International Search Report and Written Opinion dated Jul. 15, 2016 for International PCT Patent Application No. PCT Application No. US2016-027881.

International search report and written opinion dated Jul. 30, 2014 for PCT/US2014/013048.

International search report and written opinion dated Sep. 8, 2017 for PCT Application No. US-2017038542.

(56) References Cited

OTHER PUBLICATIONS

Issadore, et al.: Ultrasensitive clinical enumeration of rare cells ex vivo using a micro-hall detector. Sci Transl Med. Jul. 4, 2012;4(141):141ra92. doi: 10.1126/scitranslmed.3003747.

Jan, et al.: Cell adhesion profiling for eukaryotic cell culture. Millipore Corporation. 2007.

Jin, et al.: Targeting of CD44 eradicates human acute myeloid leukemic stem cells. Nat Med. Oct. 2006;12(10):1167-74. Epub Sep. 24, 2006.

Jordan, et al.: Cancer stem cells. N Engl J Med. Sep. 21, 2006;355(12):1253-61.

Kanof, et al.: Preparation of human mononuclear cell populations and subpopulations. Immunologic studies in humans. Current Protocols in Immunology. 1996; Supplement 19.

Kao, et al.: Increased hydrostatic pressure enhances motility of lung cancer cells. 2014 36th Annual International Conference of the IEEE, Engineering in Medicine and Biology Society (EMBC). Aug. 26-30, 2014. 2928-2931. DOI: 10.1109/EMBC.2014.6944236.

Karagiannis, et al.: Cancer-associated fibroblasts drive the progression of metastasis through both paracrine and mechanical pressure on cancer tissue. Mol Cancer Res. Nov. 2012; 10(11):1403-18. doi: 10.1158/1541-7786.MCR-12-0307. Epub Sep. 28, 2012.

Kato, et al.: Calyculins, potent antitumour metabolites from the marine sponge Discodermia calyx: biological activities. Drugs Exp Clin Res. 1988; 14(12):723-8.

Kelloff, et al.: Cancer biomarkers: selecting the right drug for the right patient. Nat Rev Drug Discov. Feb. 10, 2012;11(3):201-14. doi: 10.1038/nrd3651.

Koyama; et al.: Post-transcriptional regulation of immunomodulatory cytokines production in human skin fibroblasts by intense mechanical stresses. Journal of Bioscience and Bioengineering. vol. 93, Issue 2, Feb. 2002, pp. 234-239.

Krebs, et al.: Circulating tumor cells: their utility in cancer management and predicting outcomes. Ther Adv Med Oncl. 2010; 2(6):351-365.

Lang, et al.: Significance of micrometastasis in bone marrow and blood of operable breast cancer patients: research tool or clinical application? Expert Rev Anticancer Ther. Oct. 2007;7(10):1463-72.

Leary: The Importance of Zeta Potential for Drug/Gene Delivery in Nanomedicine. Malvern Instruments Workshop. Purdue University, West Lafayette, Indiana USA. Sep. 21, 2011.

Li, et al.: Hypoxia-inducible factors regulate tumorigenic capacity of glioma stem cells. Cancer Cell. Jun. 2, 2009;15(6):501-13. doi: 10.1016/j.ccr.2009.03.018.

Lim, et al.: Enrichment and characterization of propagating circulating tumor cells from late stage prostate and pancreatic cancer pateitns. Xcell Biosciences. Stanfford Poster. 2014.

Lin, et al.: Portable filter-based microdevice for detection and characterization of circulating tumor cells. Clin Cancer Res. Oct. 15, 2010;16(20):5011-8. doi: 10.1158/1078-0432.CCR-10- 1105. Epub Sep. 28, 2010.

Liu, et al.: ROCK inhibitor feeder cells induce the conditional reprogramming of epithelial cells. The American Journal of Pathology. 2012; 180(2):599-607.

Louie, et al.: Identification of a stem-like cell population by exposing metastatic breast cancer cell lines to repetitive cycles of hypoxia and reoxygenation. Breast Cancer Res. 2010;12(6):R94. doi: 10.1186/bcr2773. Epub Nov. 10, 2010.

Lu, et al.: Isolation of circulating epithelial and tumor progenitor cells with an invasive phenotype from breast cancer patients. Int. J. Cancer. 2010; 126:669-683.

Lugli, et al.: Prognostic impact of the expression of putative cancer stem cell markers CD133, CD166, CD44s, EpCAM, and ALDH1 in colorectal cancer. British Journal of Cancer. 2010; 103:382-390.

Mammoto, et al.: Mechanical control of tissue and organ development. Development. May 1, 2010; 137(9):1407-1420.

Manalo, et al.: Transcriptional regulation of vascular endothelial cell responses to hypoxia by HIF-1. Blood. Jan. 15, 2005;105(2):659-69. Epub Sep. 16, 2004.

Mani, et al.: The epithelial-mesenchymal transition generates cells with properties of stem cells. Cell. May 16, 2008;133(4):704-15. doi: 10.1016/j.cell.2008.03.027.

Mann, et al.: Pressure-mediated oligonucleotide transfection of rat and human cardiovascular tissues, Proc. Natl. Acad. Sci. USA, May 1999, 96:6411-16.

McCuskey, et al.: The microcirculation during endotoxemia. Cardiovascular Research. 1996; 32:752-763.

Mikolajczyk, et al.: Detection of EpCAM-Negative and Cytokeratin-Negative Circulating Tumor Cells in Peripheral Blood. Journal of Oncology. 2011; Article ID 252361, 10 pages. http://dx.doi.org/10.1155/2011/252361.

Milosevic, et al.: High tumor interstitial fluid pressure identifies cervical cancer patients with improved survival from radiotherapy plus cisplatin versus radiotherapy alone. Int J Cancer. Oct. 1, 2014;135(7):1692-9. doi: 10.1002/ijc.28403. Epub Apr. 25, 2014.

Smith, et al.: Incubators: Keeping Your Cells in Style, Life Science, 2011, 8 Pages.

Nagrath et al.: Isolation of rare circulating tumour cells in cancer patients by microchip technology. Nature 450(7173):1235-1239 (2007).

Ng, et al.: Isolation of human and mouse hematopoietic stem cells. Methods Mol Biol. 2009;506:13-21. doi: 10.1007/978-1-59745-409-4_2.

Noman, et al.: PD-L1 is a novel direct target of HIF-1α, and its blockade under hypoxia enhanced MDSC-mediated T cell activation. J Exp Med. May 5, 2014;211(5):781-90. doi: 10.1084/jem.20131916. Epub Apr. 28, 2014.

Notice of Allowance dated Oct. 27, 2017 for U.S. Appl. No. 14/163,456.

Office action dated May 25, 2017 for U.S. Appl. No. 14/163,456.

Office Action dated Feb. 19, 2016 for U.S. Appl. No. 14/163,456.

Office Action dated Jun. 27, 2016 for U.S. Appl. No. 14/163,456.

Oxygen and Cancer: Low Oxygen Levels Breed Cancer . . . Increasing Cellular Oxygen Levels Kills Cancerous Cells. http://www.cancerfightingstrategies.com/oxygen-and-cancer.html#sthash.OrFzrozo.qN7WsJL1.dpbs. 2014.

Ozkumur, et al.: Inertial focusing for tumor antigen-dependent and -independent sorting of rare circulating tumor cells. Sci Transl. Med. Apr. 3, 2013;5(179):179ra47. doi: 10.1126/scitranslmed.3005616.

Palazon, et al.: Molecular pathways: hypoxia response in immune cells fighting or promoting cancer. Clin Cancer Res. Mar. 1, 2012;18(5):1207-13. doi: 10.1158/1078-0432.CCR-11-1591. Epub Dec. 28, 2011.

Peng, et al.: A microfluidic cell culture array with various oxygen tensions. Lab Chip. Aug. 21, 2013;13(16):3239-45. doi: 10.1039/c3lc50388g. Epub Jun. 20, 2013.

Piotrowski-Daspit, et al.: Interstitial fluid pressure regulates collective invasion in engineered human breast tumors via Snail, vimentin, and E-cadherin. Integr Biol (Camb). Mar. 14, 2016;8(3):319-31. doi: 10.1039/c5ib00282f.

Preparation of Human Mononuclear Cell Populations and Subpopulations. (2009). John Wiley & Sons, Inc. Retrieved from http://onlinelibrary.wiley.com/doi/10.1002/0471142735.im07100s85/abstract.

Riethdorf, et al.: Disseminated tumor cells in bone marrow and circulating tumor cells in blood of breast cancer patients: current state of detection and characterization. Pathobiology. 2008;75(2):140-8. doi: 10.1159/000123852. Epub Jun. 10, 2008.

Roberto; Scatena et al.: "Circulating tumour cells and cancer stem cells: A role for proteomics in defining the interrelationships between function, phenotype and differentiation with potential clinical applications", Biochimica et Biophysica Acta, Apr. 2013, vol. 1835, No. 2, 129-143.

Saitoh, et al.: Selective inhibition of catalytic activity of smooth muscle myosin light chain kinase. J Biol Chem. Jun. 5, 1987;262(16):7796-801.

Salvagiotto et al.: A Defined, Feeder-Free, Serum-Free System to Generate In Vitro Hematopoietic Progenitors and Differentiated Blood Cells from hESCs and hiPSCs, PLoS ONE, Mar. 2011, 6(3):e17829, 9 pages.

(56)     References Cited

OTHER PUBLICATIONS

Schwartz et al.: Exposure of Human Vascular Endothelial Cells to Sustained Hydrostatic Pressure Stimulates Proliferation Involvement of the $\alpha$V Integrins, Circ Res, 1999, 84:315-322.

Shel Lab. Bactron Anaerobic/Environmental Chambers. Dec. 2013.

Sottnik, et al.: Tumor-induced pressure in the bone microenvironment causes osteocytes to promote the growth of prostate cancer bone metastases. Cancer Res. Jun. 1, 2015;75(11):2151-8. doi: 10.1158/0008-5472.CAN-14-2493. Epub Apr. 8, 2015.

Stohrer, et al.: Oncotic pressure in solid tumors is elevated. Cancer Res. Aug. 1, 2000;60(15):4251-5.

Stott, et al.: Isolation of circulating tumor cells using a microvortex-generating herringbone-chip. Proc Natl Acad Sci U S A. Oct. 26, 2010;107(43):18392-7. doi: 10.1073/pnas.1012539107. Epub Oct. 7, 2010.

Straight, et al.: Dissecting temporal and spatial control of cytokinesis with a myosin II Inhibitor. Science. Mar. 14, 2003;299(5613):1743-7.

Su, et al.: High extracellular pressure promotes gastric cancer cell adhesion, invasion, migration and suppresses gastric cancer cell differentiation. Oncol Rep. Aug. 2016;36(2):1048-54. doi: 10.3892/or.2016.4841. Epub May 30, 2016.

Suda, et al.: Hydrodynamic Gene Delivery: Its Principles and Applications, The American Society of Gene Therapy, Molecular Therapy, Dec. 2007, 15: 2063-2069.

Sullivan et al.: Hypoxia-induced resistance to anticancer drugs is associated with decreased senescence and requires hypoxia-inducible factor-1 activity, Mol Cancer Ther Jul. 2008, 7(7):1961-73.

Sun, et al.: A simple and effective pressure culture system modified from a transwell cell culture system. Biol Res. 2013; 46: 47-52.

Suprynowicz, et al.: Conditionally reprogrammed cells represent a stem-like state of adult epithelial cells. Proc Natl Acad Sci. 2012; 109(49):20035-20040.

Swartz, et al.: Tumor microenvironment complexity: emerging roles in cancer therapy. Cancer Res. May 15, 2012;72(10):2473-80. doi: 10.1158/0008-5472.CAN-12-0122. Epub Mar. 13, 2012.

Takahashi, et al.: A developmental framework for induced pluripotency. The Company of Biologist 2015, 142, pp. 3274-3285.

Tokuda, et al.: Effects of Hydrostatic Pressure on Carcinogenic Properties of Epithelia. PLoS One. Dec. 30, 2015;10(12):e0145522. doi: 10.1371/journal.pone.0145522. eCollection 2015.

Tse, et al.: Mechanical compression drives cancer cells toward invasive phenotype. Proc Natl Acad Sci U S A. Jan. 17, 2012;109(3):911-6. doi: 10.1073/pnas.1118910109. Epub Dec. 27, 2011.

U.S. Appl. No. 15/566,337 Office Action dated Jun. 6, 2019.

U.S. Appl. No. 15/566,337 Office Action dated Nov. 6, 2018.

U.S. Appl. No. 15/629,240 Office Action dated Apr. 30, 2019.

U.S. Appl. No. 15/629,240 Office Action dated Feb. 12, 2020.

U.S. Appl. No. 15/629,240 Office Action dated Sep. 24, 2019.

U.S. Appl. No. 15/789,464 Office Action dated Apr. 23, 2020.

U.S. Appl. No. 15/789,464 Office Action dated Jun. 13, 2019.

U.S. Appl. No. 15/817,872 Office Action dated Apr. 12, 2019.

Wang et al.: Targeting HIF1$\alpha$ eliminates cancer stem cells in hematological malignancies. Cell Stem Cell 8(4):399-411 (2011).

Warburg, et al.: Archives of Biochem, 1958, 78:578-86.

Wicha, et al.: Circulating tumor cells: not all detected cells are bad and not all bad cells are detected. J Clin Oncol. Apr. 20, 2011;29(12):1508-11. doi: 10.1200/JCO.2010.34.0026. Epub Mar. 21, 2011.

Williams: Circulating tumor cells. Proc Natl Acad Sci U S A. Mar. 26, 2013;110(13):4861. doi: 10.1073/pnas.1304186110.

Wion, et al.: PO(2) matters in stem cell culture. Cell Stem Cell. Sep. 4, 2009;5(3):242-3. doi: 10.1016/j.stem.2009.08.009.

Wright, et al.: Inexpensive low-oxygen incubators. Nature Protocols. 2006; 4:2088-2090.

Yoshida, et al.: Hypoxia enhances the generation of induced pluripotent stem cells. Cell Stem Cell. Sep. 4, 2009;5(3):237-41. doi: 10.1016/j.stem.2009.08.001. Epub Aug. 27, 2009.

Yu, et al.: Circulating tumor cells: approaches to isolation and characterization. J Cell Biol. Feb. 7, 2011;192(3):373-82. doi: 10.1083/jcb.201010021.

Yu, et al.: Ex vivo culture of circulating breast tumor cells for individualized testing of drug susceptibility. Science. Jul. 11, 2014;345(6193):216-20. doi: 10.1126/science.1253533.

Zhang, et al.: The identification and characterization of breast cancer CTCs competent for brain metastasis. Sci Transl Med. Apr. 10, 2013;5(180):180ra48. doi: 10.1126/scitranslmed.3005109.

Zhang, et al.: Zeta potential: a surface electrical characteristic to probe the interaction of nanoparticles with normal and cancer human breast epithelial cells. Biomed Microdevices. 2008; 10:321-328.

Zhe, et al.: Circulating tumor cells: finding the needle in the haystack. Am J Cancer Res. 2011;1(6):740-51. Epub Jun. 1, 2011.

Ishizaki, et al. Pharmacological Properties of Y-27632, a Specific Inhibitor of Rho-Associated Kinases, Mol. Pharmacol, (2000) 57(5):976-83.

U.S. Appl. No. 17/335,353 Office Action dated Dec. 19, 2024 (41 pages).

* cited by examiner

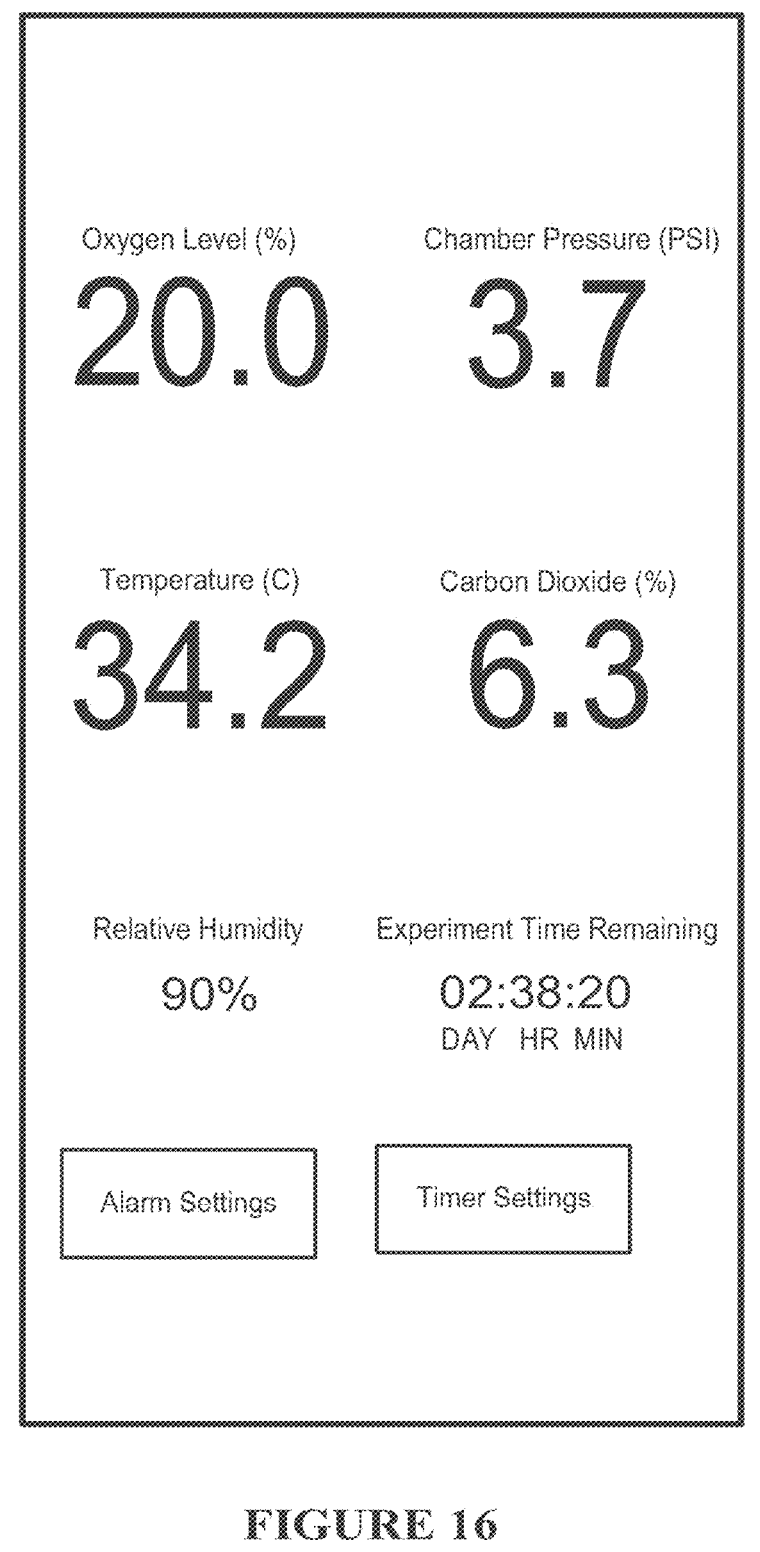

Oxygen Level (%)     Chamber Pressure (PSI)

20.0     3.7

Temperature (C)     Carbon Dioxide (%)

34.2     6.3

Relative Humidity     Experiment Time Remaining

90%     02:38:20

DAY   HR   MIN

Alarm Settings          Timer Settings

FIGURE 16

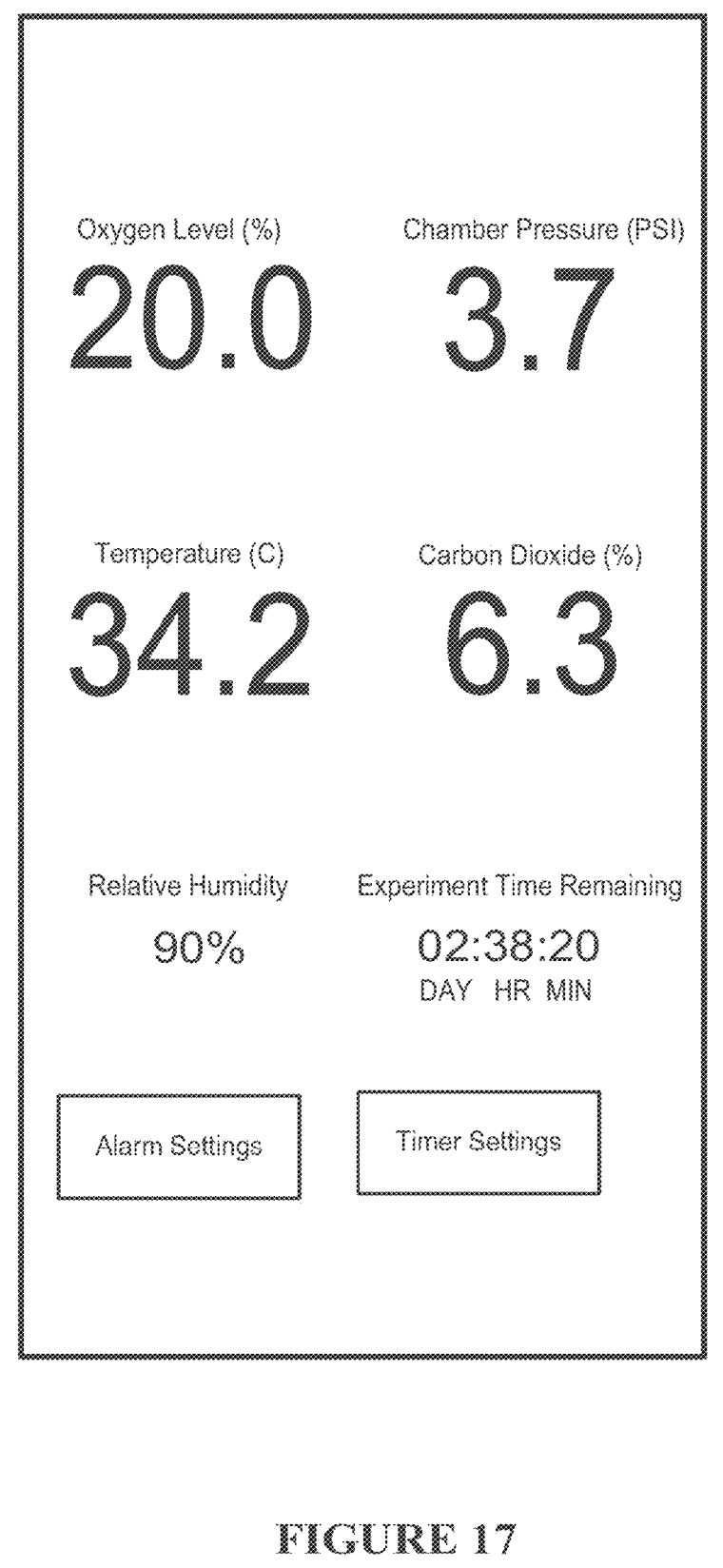

Oxygen Level (%)  Chamber Pressure (PSI)

20.0  3.7

Temperature (C)  Carbon Dioxide (%)

34.2  6.3

Relative Humidity  Experiment Time Remaining

90%  02:38:20
DAY  HR  MIN

| Alarm Settings | Timer Settings |

FIGURE 17

Door Heater

Precision Hollow Shaft

Copper Plate

Mica Washers

Back Plate

Heating Element

Paddles

Poron Insulation

Front Plate

GAS FLOW REGULATION FOR A CELL CULTURE INCUBATOR

CROSS REFERENCE

This Application is a continuation of U.S. application Ser. No. 17/335,353 filed Jun. 1, 2021, which Application is a continuation of U.S. application Ser. No. 17/077,222 filed Oct. 22, 2020, which is a continuation of U.S. application Ser. No. 15/789,464 filed Oct. 20, 2017, which is a continuation-in-part of U.S. application Ser. No. 15/566,337, filed Oct. 13, 2017, which is a national stage entry of PCT/US2016/027881, filed Apr. 15, 2016, which claims the benefit of U.S. Provisional Application No. 62/149,268, filed Apr. 17, 2015, each of which is incorporated herein by reference in its entirety.

FIELD OF THE INVENTION

The invention relates to instruments and systems for cell culture. More particularly, the invention relates to cell culture systems that can regulate aspects of the atmospheric environment within a cell culture incubator chamber.

BACKGROUND

Cell enrichment systems can be used to enrich, isolate, and expand different populations of cells. These cell populations can include, for example, cancer cells, circulating tumor cells, stem cells, and immune cells. Isolation and characterization of different cell types that are induced through a cell enrichment system can be used to understand tumor etiology, the biology of metastasis, stem cell differentiation, immune cell proliferation, and to provide a biomarker for tumor progression.

Atmospheric conditions, such as the atmospheric pressure and the concentrations of particular gases, such as oxygen, can be significant factors in cell culture that can affect the growth rate, viability, and expression of phenotypic aspects of various cell populations. To understand these biological effects, cell culture instruments that can regulate various atmospheric conditions precisely and independently of each other could be valuable for research, diagnostic, and therapeutic goals.

INCORPORATION BY REFERENCE

Each patent, publication, and non-patent literature cited in the application is hereby incorporated by reference in its entirety as if each was incorporated by reference individually.

SUMMARY OF THE INVENTION

Embodiments of the invention relate to a cell culture incubator that includes gas flow regulation system that exerts control over the atmospheric parameters to which cells in culture are exposed. Particular embodiments of the invention include an enclosed environmental chamber and a control unit operably linked to the enclosed environmental chamber, the control unit having an oxygen module and a pressure module. Embodiments of the control unit, by way of these modules, are configured to regulate both oxygen level and total gas pressure within the enclosed environmental chamber. Embodiments of the control unit are adapted (a) to provide instructions to the oxygen module to regulate an oxygen level to an instructed hypoxic oxygen level and (b) to provide instructions to the pressure module to regulate total gas pressure to an instructed positive pressure level. Embodiments may also be instructed to operate at an ambient oxygen level and an ambient pressure level. The oxygen level and the total gas pressure level are regulated independently of each other. The regulation of oxygen to the instructed hypoxic level prevails despite the oxygen partial pressure-increasing effect of the positive pressure condition associated with the instructed positive pressure level.

Some embodiments of the cell culture incubator further include one or more oxygen sensors configured to measure the oxygen level within the enclosed environmental chamber and to convey an informative signal to the oxygen module, and one or more pressure sensors configured to measure the total atmospheric gas pressure within the enclosed environmental chamber and to convey an informative signal to the pressure module. Both the oxygen module and the pressure module are within the control unit. The control unit may include further control units related to the regulation of atmospheric parameters. Typically, atmospheric control units are configured to receive sensory input from the enclosed environmental chamber or the ambient environment, and to direct instructions to other elements of a gas flow regulation system.

Embodiments of a cell culture incubator and an included gas flow regulation system may include a nitrogen source operably connected to the cell culture incubator, wherein the flow of nitrogen is regulated by the control unit.

In some of these gas flow regulation embodiments, the regulated nitrogen flow is directed into the enclosed environmental chamber by way of a chamber gas flow path, wherein the regulated nitrogen flow includes a response to oxygen sensor data by way of the oxygen module, and wherein the response to a sensed oxygen level that is above the instructed oxygen level includes an instruction to flow nitrogen into the environmental chamber. In such embodiments and consequent response, as a result of a dilution of oxygen within the enclosed environmental chamber by the inflow of nitrogen, the sensed oxygen level may come into compliance with the instructed oxygen level. At that point, the control unit may then instruct a cessation of the nitrogen flow into the environmental chamber.

In some of these gas flow regulation system embodiments for a cell culture incubator, the regulated nitrogen flow is directed into the enclosed environmental chamber by way of a chamber gas flow path, the regulated nitrogen flow includes a response to pressure sensor data by way of the pressure module, wherein the response to a pressure level that is below the instructed pressure level includes an instruction to flow nitrogen into the environmental chamber. In such embodiments and consequent response, as a result of an increase in pressure level within the enclosed environmental chamber brought about by the inflow of nitrogen, the pressure level may come into compliance with the instructed pressure level. At that point, the control unit may then instruct a cessation of the nitrogen flow into the environmental chamber.

In some of these gas flow regulation system embodiments for a cell culture incubator, the regulation of pressure within the enclosed environmental chamber by the control unit includes a response to the pressure sensor, as mediated by the pressure module. In some of these particular embodiments, the regulation of pressure within the enclosed environmental chamber includes a response to a pressure lower than the instructed pressure level, wherein such response to the high pressure includes an inflow of nitrogen. In some embodiments, the regulation of pressure within the enclosed environmental chamber includes a response to a pressure lower than the instructed pressure level, wherein such response to the high pressure includes an inflow of carbon dioxide. In some embodiments, the regulation of pressure within the enclosed environmental chamber includes a response to a pressure lower than the instructed pressure level, wherein such response to the low pressure includes a cessation of inflow of carbon dioxide or a cessation of inflow of nitrogen.

Some of these gas flow regulation system embodiments for a cell culture incubator include regulation of the level of carbon dioxide, at least in part, to engage a pH buffering system within the cell culture medium. In some of these embodiments, the regulation of carbon dioxide flow into the enclosed environmental chamber by the control unit include a response to the carbon dioxide sensor, as mediated by the carbon dioxide module. In some of these embodiments, the regulation of carbon dioxide flow into the enclosed environmental chamber by the control unit includes a response to the pressure sensor, as mediated by the pressure module.

Particular embodiments of these gas flow regulation system embodiments for a cell culture incubator are directed toward regulating oxygen level within the incubator to a hypoxic level. Accordingly, the oxygen level within the enclosed environmental chamber is regulated by the oxygen module, the oxygen module providing instructions to regulate any one or both of a flow of nitrogen or a flow of carbon dioxide into the enclosed environmental chamber. Inasmuch as oxygen level is typically regulated to a level lower than that of the ambient level, approaches to lowering oxygen include dilution by addition of nitrogen or carbon dioxide, with a venting in order to keep total gas pressure at an instructed level. In the event that the oxygen level drifts below the instructed level, input of air by an air injection pump provides an oxygen source.

In some embodiments of a gas flow regulation system, the instructions to regulate to an instructed hypoxic level include instructions to adjust the oxygen level to a value within a range of about 0.1% to about 21% oxygen. In other embodiments, the instructions to regulate to an instructed hypoxic level include instructions to adjust the oxygen level to a value within a range of about 1.0% to about 12% oxygen. In other embodiments, the instructions to regulate to an instructed hypoxic level include instructions to adjust the oxygen level to a value within a range of about 2% to about 6% oxygen.

Particular embodiments of these gas flow regulation system embodiments for a cell culture incubator are directed toward regulating the total gas pressure within the incubator to a level that is greater than the ambient total gas pressure. The total gas pressure units used here (PSIG) refer to an amount of pressure over the ambient atmospheric pressure. In typical embodiments of the gas flow regulation system, the pressure level within the enclosed environmental chamber is regulated by the pressure module, the pressure module providing instructions to regulate any one or more of a flow of nitrogen or a flow of carbon dioxide, the inflow of either gas resulting in an increased pressure.

In some embodiments of the gas flow regulation system that are directed to creating a high pressure condition, the instructions to regulate pressure to an instructed positive pressure level include instructions to adjust the pressure to a value within a range of about 0.5 PSIG to about 30 PSIG. In some embodiments, the instructions to regulate pressure to an instructed positive pressure level include instructions to adjust the pressure to a value within a range of about 1.0

PSIG to about 20 PSIG. In some embodiments, the instructions to regulate pressure to an instructed positive pressure level include instructions to adjust the pressure to a value within a range of about 2.0 PSIG to about 10 PSIG. In some embodiments, the instructions to regulate pressure to an instructed positive pressure level include instructions to adjust the pressure to a value within a range of about 2.5 PSIG to about 5.0 PSIG.

In some embodiments, the invention provides a cell culture incubator, wherein the cell culture incubator comprises: a) an enclosed environmental chamber; and b) a control unit, wherein the control unit is operably linked to the enclosed environmental chamber, wherein the control unit comprises a computer program product comprising a computer-readable medium having computer-executable code encoded therein, the computer-executable code adapted to encode: (i) an oxygen level module, wherein the oxygen level module is encoded to regulate an oxygen level of the enclosed environmental chamber, wherein the oxygen level module is encoded to control the removal of oxygen in the enclosed environmental chamber to generate a hypoxic oxygen level within the enclosed environmental chamber; (ii) a pressure module, wherein the pressure module is encoded to regulate the pressure of the enclosed environmental chamber, wherein the pressure module controls the addition of gas to generate a positive pressure condition in the enclosed environmental chamber; (iii) a temperature module, wherein the temperature module is encoded to regulate the temperature of the enclosed environmental chamber; and (iv) a humidity module, wherein the humidity module is encoded to regulate the humidity of the enclosed environmental chamber, wherein each of the oxygen level, pressure, temperature, and humidity mimics an in vivo microenvironment for a cell, wherein the cell culture incubator reaches each of an instructed oxygen level, pressure, temperature, and humidity within about 20 minutes of receiving an input of each of the instructed oxygen level, pressure, temperature, and humidity.

BRIEF DESCRIPTION OF THE FIGURES

FIG. 16 depicts an illustrative user interface for a system of the invention.

FIG. 17 depicts an illustrative user interface for a system of the invention.

DETAILED DESCRIPTION

Method of the Invention

A method of the present invention can be used to isolate CTCs, and other target cell subpopulations, from a biological sample. A method of the invention can be used, for example, to isolate cell populations, selectively separate cell populations, maintain cells in a differentiated or an undifferentiated state, forcibly differentiate cells, enrich cell populations, expand cell populations (through proliferation or selective enrichment), modulate functions of cell populations, modulate morphology of cell populations, modulate epigenetic characteristics, and modulate gene and protein expression profiles. A method of the invention can be used in, for example, primary cells, cell lines, or microbial communities.

Target cell subpopulations can include, for example, CTCs, cancer stem cells (CSCs), hematopoietic stem cells (HSCs), endothelial progenitor cells (EPCs), pre-cancerous cells, stem cells, fetal stem cells, undifferentiated stem cells, fetal cells, bone marrow cells, progenitor cells, foam cells, mesenchymal cells, epithelial cells, epithelial progenitor cells, endothelial cells, endometrial cells, trophoblasts, cancer cells, red blood cells, white blood cells, immune system cells, connective tissue cells, hepatocytes, neurons, induced pluripotent stem (IPS) cells, or any combination thereof.

A method of the invention can be used, for example, to maintain neuronal cells in culture, to maintain hepatocytes in culture, and toxicity screening. The invention can be used to differentiate IPS cells and stems cell into, for example, cells of the mesoderm, ectoderm, and endoderm. A method of the invention can be used to differentiate cells into neurons, cardiomyocytes, hepatocytes, hematopoietic stem cells, osteoblasts, osteoclasts, epithelial cells, endothelial cells, astrocytes, adipocytes, immune cells, mast cells, erythrocytes, oocytes, or spermatocytes.

CTCs can be composed of heterogeneous clusters of cancer and immune cells in vivo and can display differential expression of immunomodulatory and stem cell signaling pathway in vitro.

Figure 1:
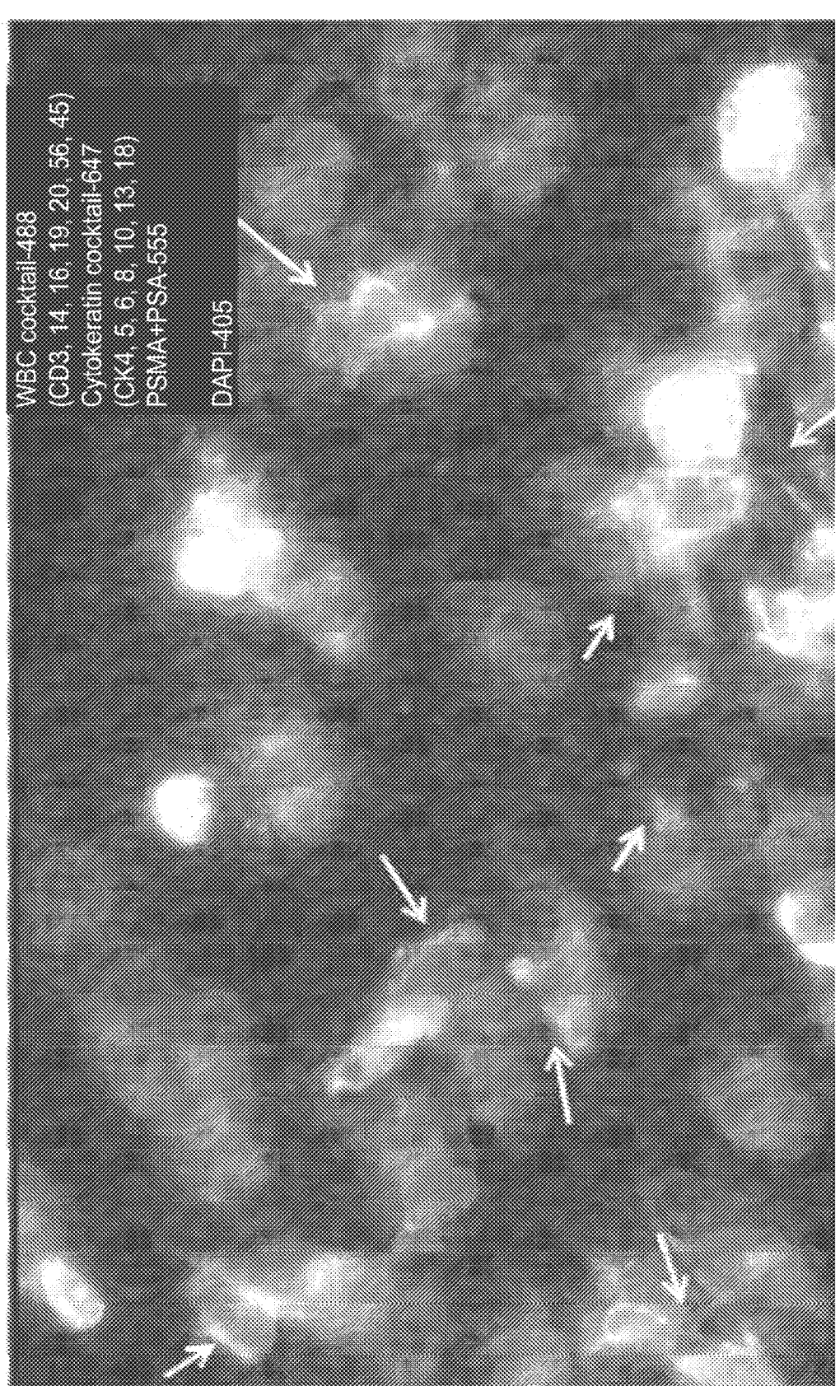
FIG. 1 is an immunofluorescence image of a representative CTC cluster.

FIG. 1 displays immunofluorescence (IF) for a circulating tumor cell cluster from a subject with castration-resistant prostate cancer (CRPC). The IF image demonstrates that CTCs can contain both cancer and immune cells. The DAPI staining (indicated by oval-shaped cell staining) indicates the nuclei of the cells. A white blood cell (WBC) antibody cocktail can be used to detect, for example, CD3, CD14, CD16, CD19, CD20, CD45, and CD56, in the CTC cluster (white arrows in FIG. 1). A cytokeratin antibody cocktail can be used to detect, for example, CK4, CK5, CK6, CK8, CK10, CK13, and CK18 in the CTC cluster (fibrillar staining seen in and around oval-shaped nuclei in FIG. 1). The bright white staining, and the fibrillar staining around the oval-shaped nuclei, indicates prostate-specific membrane antigen (PSMA) and prostate-specific antigen (PSA) proteins. The numbers in the legend indicate the wavelength (nm) used for excitation of the stains.

Figure 2:
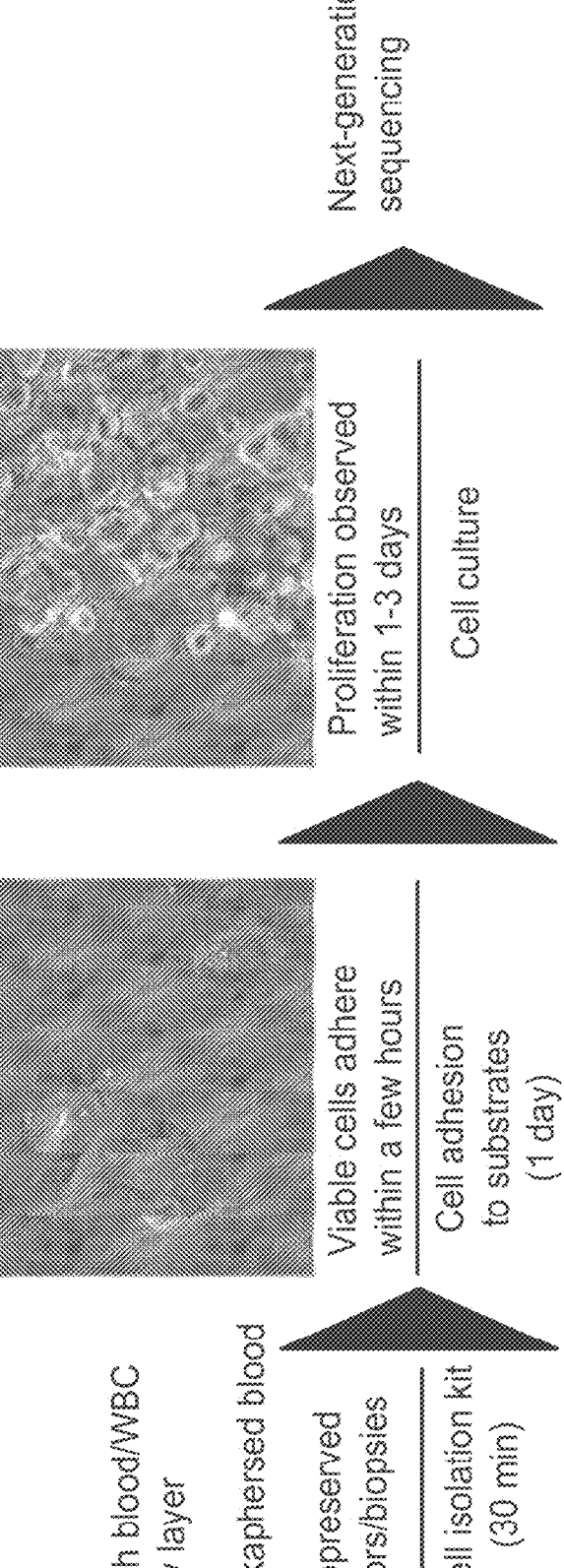
FIG. 2 is an illustrative workflow for enrichment of a target subpopulation of cells.

FIG. 2 depicts an illustrative workflow that can be used to obtain an enriched population of cells from a heterogeneous cell population. The sources of cells used in a method of the invention can include, for example, fresh blood, white blood cells (WBC), the buffy layer of centrifuged blood, cryopreserved tumors and biopsies, samples for leukapheresis, fine needle aspirates, fresh biopsies, urine, or fecal matter. After obtaining a sample from a subject, the sample can be prepared for use in a cell isolation kit to separate, for example, a blood sample into plasma, white blood cells and platelets, and red blood cells. CTCs can be found in the white blood cell and platelet fraction of centrifuged blood. The cell isolation step can be about 30 minutes long. After the heterogeneous cell population has been isolated, the cells can be applied to the enrichment medium for propagation and enrichment of viable CTC colonies. The adhesion of the cells to the substrate can take from a few hours to about one day. Proliferation during culture of the cells can be observed within about 1 to 3 days after adherence, after which next-generation sequencing (NGS) can be performed on the cell colonies for the markers of interest. Next-generation sequencing methods can include, for example, whole genome sequencing, whole genome resequencing, whole exome sequencing, whole transcriptome mRNA sequencing, ChIP-sequencing, and bioinformatics.

Figure 3:
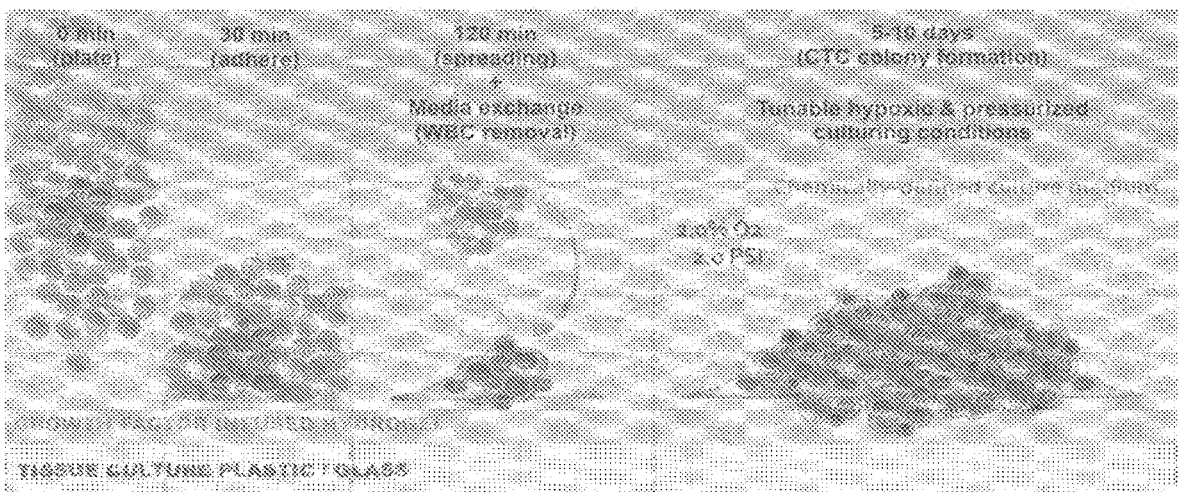
FIG. 3 depicts enrichment and propagation of a target subpopulation of cells using a method of the invention.

FIG. 3 depicts adherence and propagation of a collected heterogeneous cell population from a subject. First, the cells can be applied to a plate, which can be coated with a substance, such as a growth factor-infused hydrogel. After about 30 minutes, the cells are adhered to the plate. Over the next two hours, the cells spread across the plate, and the growth medium is exchanged allowing for removal of any remaining white bloods cells (WBCs). The media is replaced with a chemically-defined culture medium to promote the growth of CTC colonies. The cells can be grown in an environment that can be adjusted to mimic, for example, the tumor microenvironment, via changes in oxygen or pressure levels to obtain viable CTCs. In some embodiments, the cells are grown in hypoxic conditions.

The present invention can use a substrate to capture target cell subpopulations from a sample. The heterogeneous cell population can be applied to, for example, a culture dish coated with a substrate that can promote growth and enrichment of the target cell population. The target cell subpopulation can adhere to the substrate with higher affinity than other cells, for example, white blood cells. Cells that do not adhere to the substrate can be washed away with media or maintained in culture. Once adhered, the cells can spread and begin dividing on the substrate.

The substrate can comprise, for example, 1, 2, 3, 4, or 5 layers. The distance between two substrates layers may range from about 0.001 to about 20 mm, about 1 to about 10 mm, or about 1 to about 5 mm and each layer can be about 0.001, about 1, about 2, about 3, about 4, about 5, about 6, about 7, about 8, about 9, about 10, about 12, about 15, about 17, or about 20 mm.

The cells can be plated on a material made of, for example, plastic, glass, gelatin, polyacrylamide, or any combination thereof. The dishes used to the plate the cells can be, for example, microscope slides, culture plates, culture dishes, Petri dishes, microscope coverslips, an enclosed environmental chamber, a sealed culture dish, or multi-well culture dishes.

The binding surface layer of the substrate can be the portion of the substrate that is in contact with the captured cells. In some instances, the binding surface layer is the only layer, adjacent to the base layer, or separated from the base layer by one or more middle layers.

The binding surface layer of the substrate can comprise, for example, cell monolayers, cell lysates, biological materials associated with the extracellular matrix (ECM), gelatin, or any combination thereof.

Biological materials associated with the ECM can include, for example, collagen type I, collagen type IV, laminin, fibronectin, elastin, reticulin, vimentin, hygroscopic molecules, glycosaminoglycanse, proteoglycans, roteoglycans, glycocalyx, bovine serum albumin, human serum albumin, Poly-L-lysine, Poly-D-lysine, or Poly-L-ornithine. The gelatin can be from an animal source, for example, the gelatin can porcine or bovine.

The monolayer of cells used in the substrate can be, for example, mammalian cells, endothelial cells, vascular cells, venous cells, capillary cells, human umbilical vein endothelial cells (HUVEC), human lung microvascular endothelial cells (HLMVEC), human keratinocytes, human mesenchymal stem cells, human bone marrow stromal cells, and human astroglial cells. The cell lines can be obtained from a primary source or from an immortalized cell line. The monolayer of cells can be irradiated by ultraviolet light or X-ray sources to cause senescence of cells. The monolayer can also contain a mixture of one or more different cell types. The different cell types may be co-cultured together. One non-limiting example of co-culture is a combination of primary human endothelial cells co-cultured with transgenic mouse embryonic fibroblasts mixed to form a monolayer.

The binding surface layer of the substrate can contain, for example, a mixture of intracellular components. One method that can be used to obtain a mixture of intracellular components is lysis of the cells and collection of the cytosolic and cytoskeletal components. The lysed cells may be primary or immortalized. The lysed cells can be from either mono- or co-cultures.

The binding surface layer of the substrate can contain biological materials associated with the extracellular matrix (ECM) or binding moieties such as hyaluronic acid hydrogels. For example, gelatin can be mixed directly with cells, binding moieties, biological materials associated with the ECM, or any combination thereof, to make a binding surface layer for the substrate. For example, the binding surface layer can comprise a gelatin mixed with a collagen.

The substrate can have one or more middle layers. The middle layer of the substrate can be one or more monolayers of cells. The cells of the monolayer can be of varying origin. For example, the middle layer of the substrate can be made by growing a confluent monolayer of mouse embryonic fibroblasts on the base layer and then growing another layer of cells, for example, the binding surface layer, on top of the confluent mouse embryonic fibroblasts.

A feeder layer can be used in the substrate for growth and enrichment of the target cell subpopulation. A feeder layer can sit adjacent to a base layer and can be separated from the binding surface layer of the substrate. The feeder layer can be a monolayer of feeder cells. The cells of the monolayer can be of varying origin. For example, the feeder layer can be made by growing a monolayer of human endothelial cells or mouse embryonic fibroblasts on a base layer.

Conjugation of layers of the substrate can be done by allowing cells to grow in a monolayer on top of the base layer or middle layer. Conjugation of layers can also be done by pre-treating the surface with a surface of either net positive, net negative, or net neutral charge. The conjugation procedure can be aided by chemical moieties, linkers, protein fragments, nucleotide fragments, or any combination thereof.

The configuration and composition of the substrate can be tailored for enrichment of a particular target cell subpopulation. The composition of the substrate can vary based on, for example, patient type, cancer type, stage of cancer, patient medical history, and genomic and proteomic analysis of the patient tumor.

The enrichment media used for growing the cells can be supplemented or made with culture media that has been collected from cell cultures, blood plasma, or any combination thereof. The enrichment media can be, for example, Plating Culture Medium, Type R Long Term Growth Medium, Type DF Long Term Growth Medium, Type D Long Term Growth Medium, and MEF—Enrichment Medium, or any combination thereof. The enrichment medium can contain, for example, a primary nutrient source, animal serum, ions, elements, calcium, glutamate, magnesium, zinc, iron, potassium, sodium, amino acids, vitamins, glucose, growth factors, hormones, tissue extracts, proteins, small molecules, or any combination thereof.

Non-limiting examples of amino acids that can used in the enrichment media include essential amino acids, phenylalanine, valine, threonine, tryptophan, isoleucine, methionine, leucine, lysine, and histidine, arginine, cysteine, glycine, glutamine, proline, serine, tyrosine, alanine, asparagine, aspartic acid, glutamic acid, or any combination thereof.

Non-limiting examples of growth factors that can be used in the enrichment media include epidermal growth factor (EGF), nerve growth factor (NGF), brain derived neurotrophic factor (BDNF), fibroblast growth factor (FGF), stem cell factor (SCF), insulin-like growth factor (IGF), transforming growth factor-beta (TGF-$\beta$), basic fibroblast growth factor (bFGF), testosterone, estrogen, thyroid-stimulating hormone (TSH), follicle-stimulating hormone, luteinizing hormone, eicosanoids, melatonin, thyroxine, vasopressin, oxytocin, or any combination thereof.

Non-limiting examples of hormones include peptide hormones, insulin, steroidal hormones, hydrocortisone, progesterone, testosterone, estrogen, dihydrotestosterone, or any combination thereof.

Non-limiting examples of tissue extracts include pituitary extract. Non-limiting examples of small molecule additives include sodium pyruvate, endothelin-1, transferrin, cholesterol, or any combination thereof.

Non-limiting examples of other components that can be used in the enrichment media include pipecolic acid, gamma-Aminobutyric acid (GABA), human serum albumin, bovine serum albumin, glutathione, human alpha-fetoprotein, bovine alpha-fetoprotein, human holo-transferrin, or any combination thereof.

Non-limiting examples of salts that can be used in the enrichment media include calcium chloride, magnesium chloride, sodium bicarbonate, magnesium sulfate, sodium chloride, citrate, potassium phosphate, sodium phosphate, or any combination thereof.

In some embodiments, the enrichment media contains pipecolic acid, GABA, bFGF, TGFβ-1, human insulin, human holo-transferrin, human serum albumin, and reduced glutathione.

The amino acids, growth factors, hormones, tissue extracts, salts, or any other component that can be used in the enrichment media can be at a concentration of, for example, about 0.001 nM, about 0.005 nM, about 0.01 nM, about 0.015 nM, about 0.02 nM, about 0.25 nM, about 0.03 nM, about 0.035 nM, about 0.04 nM, about 0.045 nM, about 0.05 nM, about 0.055 nM, about 0.06 nM, about 0.065 nM, about 0.07 nM, about 0.075 nM, about 0.08 nM, about 0.085 nM, about 0.09 nM, about 0.1 nM, about 0.015 nM, about 0.2 nM, about 0.25 nM, about 0.3 nM, about 0.35 nM, about 0.4 nM, about 0.45 nM, about 0.5 nM, about 0.55 nM, about 0.6 nM, about 0.65 nM, about 0.7 nM, about 0.75 nM, about 0.8 nM, about 0.85 nM, about 0.9 nM, about 0.95 nM, about 0.001 µM, about 0.005 µM, about 0.01 µM, about 0.015 µM, about 0.02 µM, about 0.025 µM, about 0.03 µM, about 0.035 µM, about 0.04 µM, about 0.045 µM, about 0.05 µM, about 0.055 µM, about 0.06 µM, about 0.065 µM, about 0.07 µM, about 0.075 µM, about 0.08 µM, about 0.085 µM, about 0.09 µM, about 0.085 µM, about 0.09 µM, about 0.085 µM, about 0.09 µM, about 0.085 µM, about 0.09 µM, about 0.085 µM, about 0.09 µM, about 0.085 µM, about 0.09 µM, about 0.085 µM, about 0.09 µM, about 0.095 µM, about 0.1 µM, about 0.15 µM, about 0.2 µM, about 0.25 µM, about 0.3 µM, about 0.35 µM, about 0.4 µM, about 0.45 µM, about 0.5 µM, about 0.55 µM, about 0.6 µM, about 0.65 µM, about 0.7 µM, about 0.75 µM, about 0.8 µM, about 0.85 µM, about 0.9 µM, about 0.95 µM, about 0.001 mM, about 0.005 nM, about 0.01 mM, about 0.015 mM, about 0.02 mM, about 0.025 mM, about 0.03 mM, about 0.035 mM, about 0.04 mM, about 0.045 mM, about 0.05 mM, about 0.055 mM, about 0.06 mM, about 0.065 mM, about 0.07 mM, about 0.075 mM, about 0.08 mM, about 0.085 mM, about 0.09 mM, about 0.095 mM, about 0.1 mM, about 0.15 mM, about 0.2 mM, about 0.25 mM, about 0.3 mM, about 0.35 mM, about 0.4 mM, about 0.45 mM, about 0.5 mM, about 0.55 mM, about 0.6 mM, about 0.65 mM, about 0.7 mM, about 0.75 mM, about 0.8 mM, about 0.85 mM, about 0.9 mM, about 0.95 mM, about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 250 mM, about 300 mM, about 350 mM, about 400 mM, about 450 mM, about 500 mM, about 600 mM, about 700 mM, about 800 nM, about 900 mM, and about 1 M.

The culturing conditions in a method of the invention can be adjusted to simulate oxygen and pressure levels found in a particular microenvironment to promote the collection of a desired cell population. The microenvironment can be, for example, a tumor microenvironment, bone metastatic environment, vasculature environment, or brain microenvironment. The oxygen level used during culturing conditions or in a cell incubator can be, for example, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% oxygen in the incubator. In some embodiments, the cells can be grown under hypoxic conditions.

The culturing condition in a method of the invention can be adjusted to simulate the pressure found in the tumor microenvironment to promote the collection of, for example, CTCs, maintenance of a tumor biopsy, or expansion of a tumor biopsy. The pressure used during culturing conditions can be a PSI gauge (PSIG) reading of, for example, about 0.5 PSIG, about 0.6 PSIG, about 0.7 PSIG, about 0.8 PSIG, about 0.9 PSIG, about 1 PSIG, about 1.1 PSIG, about 1.2 PSIG, about 1.3 PSIG, about 1.4 PSIG, about 1.5 PSIG, about 1.6 PSIG, about 1.7 PSIG, about 1.8 PSIG, about 1.9 PSIG, about 2 PSIG, about 2.5 PSIG, about 3 PSIG, about 3.5 PSIG, about 4 PSIG, about 4.5 PSIG, about 5 PSIG, about 6 PSIG, about 7 PSIG, about 8 PSIG, about 9 PSIG, about 10 PSIG, about 15 PSIG, about 20 PSIG, about 25 PSIG, about 30 PSIG, about 35 PSIG, about 40 PSIG, about 45 PSIG, about 50 PSIG, or about 55 PSIG.

The pressure used during culturing conditions can be, for example, about 3.45 kPa, about 4.14 kPa, about 4.83 kPa, about 5.52 kPa, about 6.21 kPa, about 6.89 kPa, about 7.58 kPa, about 8.27 kPa, about 8.96 kPa, about 9.65 kPa, about 10.3 kPa, about 11 kPa, about 11.7 kPa, about 12.4 kPa, about 13.1 kPa, about 13.8 kPa, about 17.2 kPa, about 20.7 kPa, about 24.1 kPa, about 27.6 kPa, about 31 kPa, about 34.4 kPa, about 41.4 kPa, about 48.3 kPa, about 55.2 kPa, about 62.1 kPa, about 68.9 kPa, about 103 kPa, about 138 kPa, about 172 kPa, about 207 kPa, about 241 kPa, about 276 kPa, about 310 kPa, about 345 kPa, or about 379 kPa.

The pH of the enrichment media used in a method of the invention can be, for example, about 2, about 2.1, about 2.2, about 2.3, about 2.4, about 2.5, about 2.6, about 2.7, about 2.8, about 2.9, about 3, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.55, about 4.6, about 4.7, about 4.8, about 4.9, about 5, about 5.5, about 6, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.5, about 9, about 9.5, about 10, about 10.5, or about 11 pH units.

The viscosity of the enrichment media can be adjusted by, for example, at least 0.001 Pascal-second (Pa·s), at least 0.001 Pa·s, at least 0.0009 Pa·s, at least 0.0008 Pa·s, at least 0.0007 Pa·s, at least 0.0006 Pa·s, at least 0.0005 Pa·s, at least 0.0004 Pa·s, at least 0.0003 Pa·s, at least 0.0002 Pa·s, at least 0.0001 Pa·s, at least 0.00005 Pa·s, or at least 0.00001 Pa·s, depending on the cell types being cultured.

The oxygen solubility of the enrichment media can be, for example, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 65%, about 70%, about 75%, about 80%, about 85%, about 90%, about 95%, about 96%, about 97%, about 98%, or about 99%.

A method of the invention can further comprise coating surfaces for cell adhesion with particular media compositions to promote cellular and cellular protein binding to the surface. The surface can be, for example, a cell culture plate, a cell culture plate with multiple wells, a petri dish, a glass slide, a cover slip, or a glass dish. The media used for coating of the cell adhesion surfaces can include, for example, 3-(aminopropyl)-trimethoxysilane, (3-mercaptopropyl)trimethoxysilane, (3-Aminopropyl)triethoxysilane, N-[3-(trimethoxysilyl)-propyl]-ethylenediamine, (3-Glycidyloxypropyl)trimethoxysilane, [3-(2-aminoethyl-amino)-propyl]trimethoxysilane, trimethoxy[3-(methylamino)propyl]silane, 3-aminopropyl(diethoxy)-methylsilane, or glutaraldehyde.

The surface coating can further comprise an extracellular matrix (ECM) mix to facilitate cell binding. The mix can include, for example, collagens, basement membrane proteins, collagen IV, laminins, fibronectin, vitronectin, vimentin, tumor-derived extracellular matrix proteins, or inert self-assembling peptides systems. The components used can be animal- or human-derived. The ECM mix can be diluted to a pH of about 4 to about 10 using, for example, potassium hydroxide (KOH), l-glycine, DMEM powder, sodium hydroxide (NaOH), or PBS. The ECM mix can be further supplemented with, for example, human plasma or animal-derived serum. The animal-derived serum can be, for example, bovine serum or fetal bovine serum.

The cells can be cultured in enrichment media, or in a cell culture incubator, for about 1 minute, about 2 minutes, about 3 minutes, about 4 minutes, about 5 minutes, about 10 minutes, about 15 minutes, about 20 minutes, about 25 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 18 hours, about 24 hours, about 30 hours, about 36 hours, about 42 hours, about 2 days, about 3 days, about 4 days, about 5 days, about 6 days, about 1 week, about 2 weeks, about 3 weeks, about 4 weeks, about 2 months, about 3 months, about 4 months, about 5 months, about 6 months, about 7 months, about 8 months, about 9 months, about 10 months, about 11 months, about 1 year, about 1.5 years, about 2 years, about 2.5 years, or about 3 years.

Databases containing information regarding genetic mutations that are prevalent in specific types of cancer can be used to compare the genetic profile or biomarker expression of the target subpopulations derived using the present invention to known mutations. Non-limiting examples of databases that can be used for comparison include COSMIC, cBio Portal, Human Gene Mutation Database (HGMD™), GWAS central, and the Universal Mutation Database.

Cell Culture Incubator

Figure 24A:
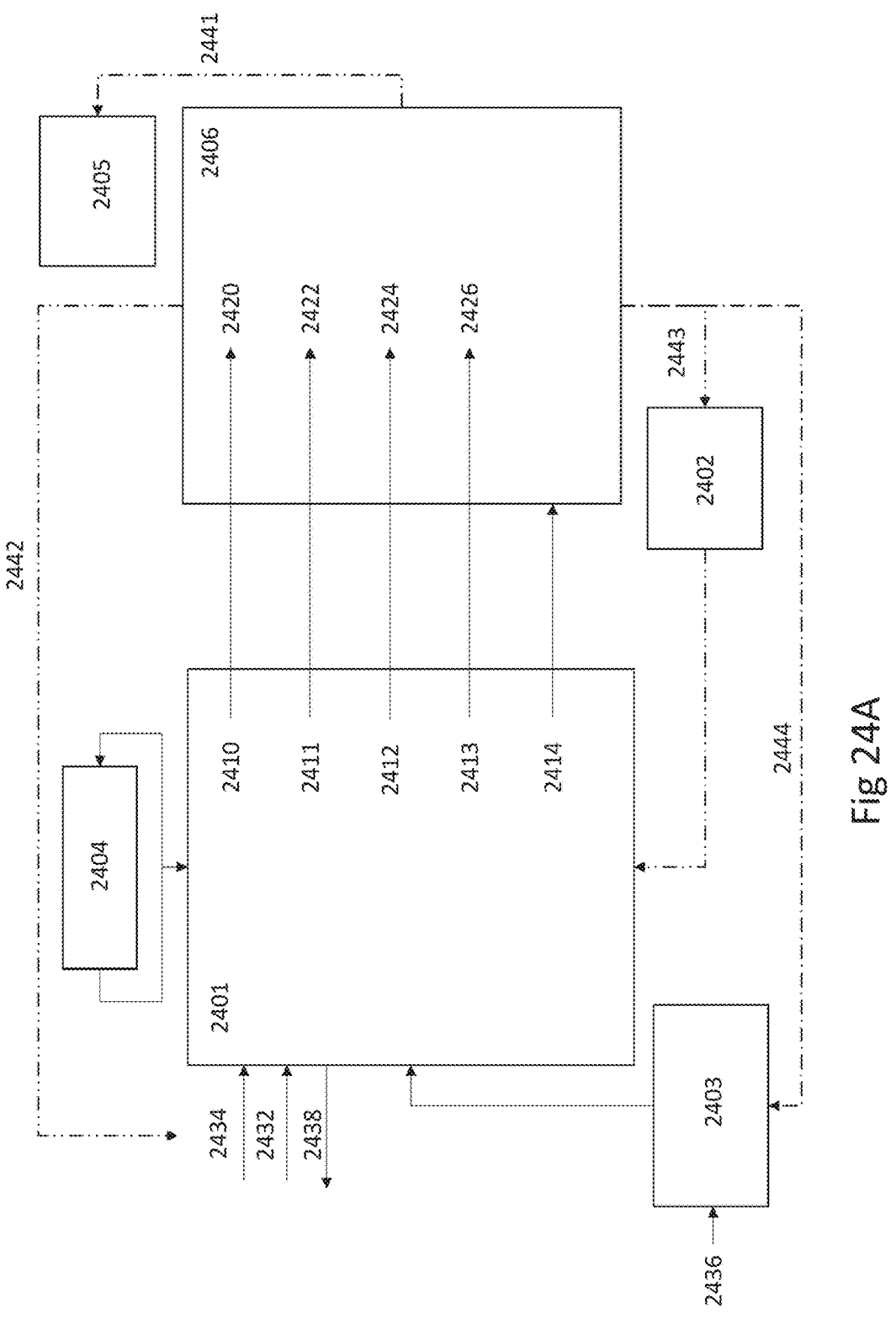
FIG. 24A is an illustrative embodiment of gas flow control system to be used with a cell culture incubator and a method of the invention.
Figure 24B:
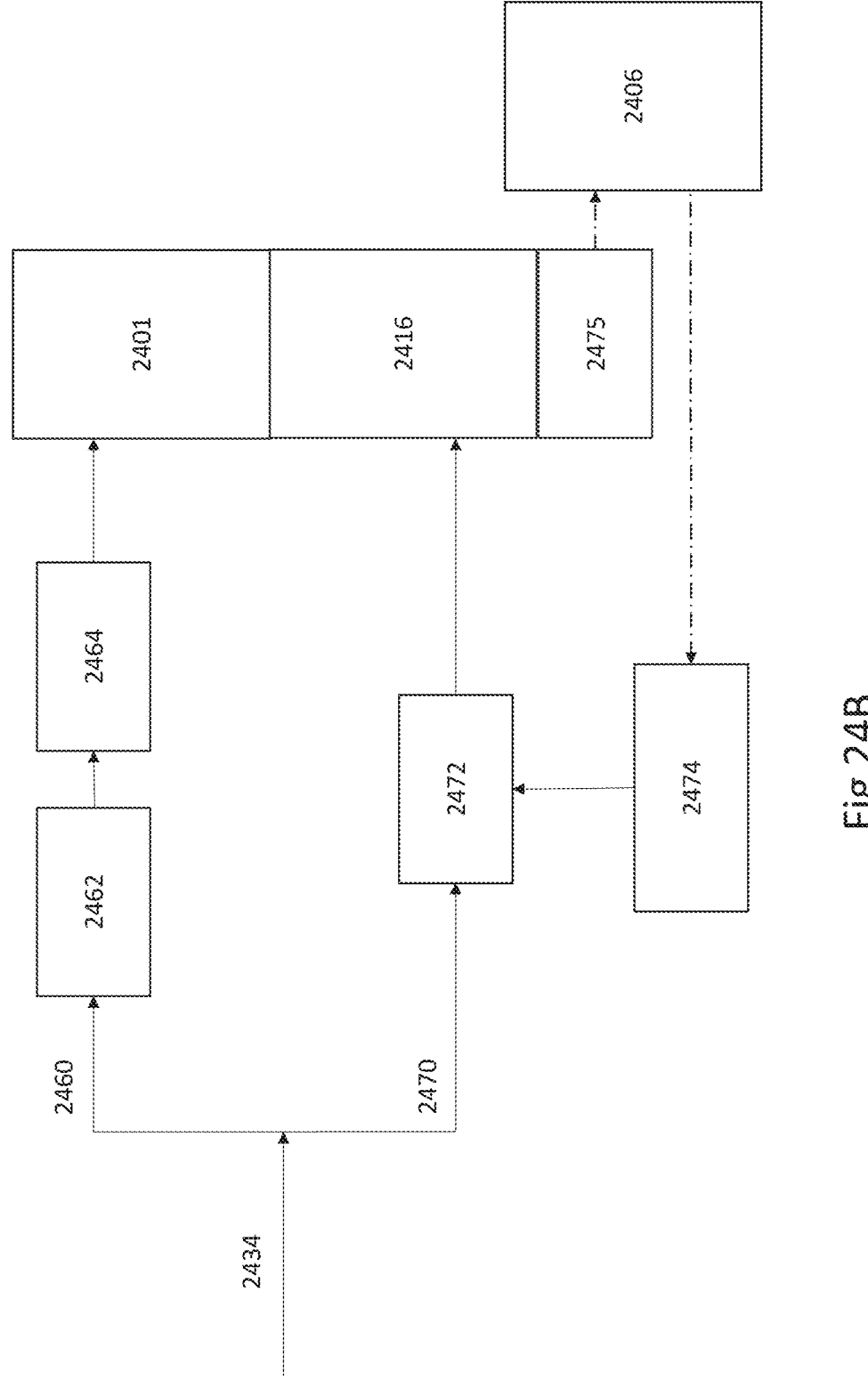
FIG. 24B is an illustrative embodiment of nitrogen flow system to be used with a cell culture incubator and a method of the invention.

The invention further provides a cell culture incubator. The cell culture incubator can comprise an enclosed environmental chamber. The cell culture incubator can be configured to maintain a gas composition of the enclosed environmental chamber, an atmospheric pressure of the enclosed environmental chamber, humidity, carbon dioxide level, oxygen level, and an internal ambient temperature of the enclosed environmental chamber. The cell culture incubator can comprise a control unit, wherein the control unit can be configured to maintain at least one of the gas composition, the atmospheric pressure, humidity, carbon dioxide level, oxygen level, or the internal ambient temperature. The control unit can be operably linked to the enclosed environmental chamber. The control unit can be configured to maintain at least two of the gas compositions, the atmospheric pressure, humidity, carbon dioxide level, oxygen level, and the internal ambient temperature. The control unit can be configured to maintain the gas composition, the atmospheric pressure, humidity, carbon dioxide level, oxygen level, and the internal ambient temperature. The control unit of the cell culture incubator can be user-controlled or automated based on sensors in the cell culture incubator. The control unit can be configured to create a dynamic gas composition, atmospheric pressure, humidity, carbon dioxide level, oxygen level and the internal ambient temperature as a function of time. The control unit can be configured to cycle between several different gas compositions, atmospheric pressure, humidity level, carbon dioxide level, oxygen level, and the internal ambient temperature as a function of time, and can be stochastic or periodic. Some aspects of embodiments of the cell culture incubator are described further below in the section entitled "Gas Flow Regulation System", and are depicted in FIGS. 24A-24B.

At least one of the gas composition, the atmospheric pressure, humidity, carbon dioxide level, oxygen level, and the internal ambient temperature can be configured for selective proliferation of a target primary cell subpopulation as compared to a non-target primary cell subpopulation. The selective proliferation of a target cell subpopulation can be evidenced by, for example, a two-fold increase in the proliferation rate of the target primary cell subpopulation as compared to the proliferation rate of the non-target primary cell subpopulation. At least one of the gas composition, the atmospheric pressure, humidity, carbon dioxide level, oxygen level, and the internal ambient temperature can be configured for selective adherence of a target primary cell subpopulation as compared to a non-target primary cell subpopulation. The selective adherence of a target primary cell subpopulation can be evidenced by a two-fold increase in adherence of the target primary cell subpopulation as compared to adherence of the non-target primary cell subpopulation. At least one of the gas composition, the atmospheric pressure, humidity, carbon dioxide level, oxygen level, and the internal ambient temperature can be configured to promote selective colony formation of the target primary cell as compared to colony formation of the non-target primary cell subpopulation. The selective colony formation can be evidenced by a two-fold increase in colony formation of the target primary cell subpopulation as compared to colony formation of the non-target primary cell subpopulation. The colony formation can be a two-dimensional or three-dimensional colony formation.

The gas composition in the cell culture incubate can comprise an oxygen level between about 0.1 to about 21%. In some embodiments, the cell culture incubator maintains an oxygen level of the enclosed environmental chamber of no more than about 5%. In some embodiments, the cell culture incubator maintains an oxygen level of the enclosed environmental chamber of no more than about 2%. In some embodiments, the cell culture incubator maintains an oxygen level of the enclosed environmental chamber of no more than about 1%.

The cell culture incubator can maintain a user-controlled or automated atmospheric pressure of the enclosed environmental chamber of about 1 PSIG (6.89 kPa) or greater. In some embodiments, the cell culture incubator maintains a user-controlled atmospheric pressure of the enclosed environmental chamber of about 2 PSIG (13.8 kPa) or greater. In some embodiments, the cell culture incubator maintains a user-controlled atmospheric pressure of the enclosed environmental chamber of about 5 PSIG (34.5 kPa). The cell culture incubator can maintain the atmospheric pressure of the enclosed environmental chamber by controlling an inlet gas pressure.

The cell culture incubator can comprise a user interface. The user interface can be configured to allow a user to control the gas composition, oxygen level, carbon dioxide level, humidity, atmospheric pressure, or internal ambient temperature. The user interface can be configured to provide a display of the gas composition to a user. The user interface can be configured to provide a display of the oxygen level, carbon dioxide level, humidity, atmospheric pressure of the enclosed environmental chamber, and internal ambient temperature to a user. The cell culture incubator can be configured to maintain an internal humidity of the enclosed environmental chamber. The enclosed environmental chamber can comprise a shelf, a pressure sensor, an oxygen sensor, a carbon dioxide sensor, a temperature sensor, or an oxygen removal catalyst. The shelf in the enclosed environmental chamber can be made of, for example, stainless steel, silver, gold, or copper. In some embodiments, the shelf of the enclosed environmental chamber is a copper shelf.

The cell culture incubator can be operably linked to a gas tank. The gas tank can comprise a CO2 tank, a nitrogen gas tank, an oxygen gas tank, a gas tank comprising a defined mixture of one or more gases, or any combination thereof. The cell culture incubator can be operably linked to the gas tank via a pressurized pump or pressure sensor (e.g., a pressure gauge). The pressurized pump or pressure sensor can maintain a controlled flow of gas from the gas tank to the enclosed environmental chamber of the cell culture incubator. The controlled flow of gas from the one or more tanks can have a set inlet pressure, the set inlet pressure of the one or more tanks configured to maintain the desired internal gas composition or internal atmospheric pressure of the enclosed environmental chamber. The enclosed environmental chamber can have a vacuum seal on the door of the enclosed environmental chamber. The enclosed environment chamber can be sealed by an inflatable seal.

The incubator can comprise a pressurized door. In some embodiments, the incubator comprises an outer pressurized door and an inner pressurized door. The outer pressurized door and/or inner pressurized door can be, e.g., a double-walled door. The double-walled door can have a vacuum-sealed latch. The outer pressurized door may include an integrated pressure sensor on the door. The incubator can comprise a door entry. The door entry can provide an entrance into an enclosed environmental chamber. Dimensions of the door entry opening can be less than the pressurized door. The door entry can comprise a rubber gasket. The rubber gasket can create a pressurized seal.

The cell culture incubator can comprise an integrated pressure sensor. The integrated pressure sensor can be a manifold pressure sensor. The integrated pressure sensor can be a water-based or silicon based pressure sensor. The incubator can comprise a sterilization unit. The sterilization unit can be a UV-based sterilization unit. The UV-based sterilization unit can be configured to provide UV rays to the entire space of an enclosed environmental chamber of the incubator. The incubator can comprise a CO2 sensor. The CO2 sensor can be configured to provide a detectable alarm upon deviation of +/−0.5% from a defined CO2 level of the enclosed environmental chamber. The incubator can comprise an enclosed environmental chamber. The incubator can comprise a water humidity tray. The water humidity tray can promote sterility of the enclosed environmental chamber. The water humidity tray may be tethered directly to humidity sensor or regulator. The incubator can comprise an air jacket. The air jacket can maintain optimal temperature and proper gas regulation. The air jacket can be a physically distinct compartment. The air jacket may house electrical controllers and circuit boards. The incubator can comprise an oxygen removal catalyst and sensor for regulating oxygen levels within the incubator.

The incubator can comprise a heating element or temperature control. The heating element or temperature control can comprise silent fan-based heating elements. The silent fan-based heating elements can dispense a constant flow of heated air into the air-jacket compartment. Passive heating can then warm the inner chamber in an evenly distributed and constant manner. The incubator can comprise a pressurized pump and regulator configured to provide a defined gas composition and internal atmospheric pressure. A motor based pump can dispense defined gas mixtures to maintain chamber pressure and gas composition levels (e.g., 1% oxygen, 5% CO2, 94% N2). The incubator can comprise a user interface. A user can use the user interface to set gas levels and pressures. The user interface can be integrated to the sensor and pump for direct control. The pressurized pump and regulator can comprise a gas inlet. The gas inlet can allow flow of any gas into the enclosed environmental chamber. For example, the gas inlet can be connected to an oxygen tank. The gas inlet can be connected to a CO2 tank. The gas inlet can be connected to a nitrogen tank. In some embodiments, the incubator comprises a gas inlet connected to an oxygen tank, a gas inlet connected to a CO2 tank, and a gas inlet connected to a nitrogen tank. The gas inlet can be connected to a tank containing a custom gas mixture. In some embodiments, a user can control a flow of gas through any gas inlet. Any one of the gas inlets may be connected to a flow meter. The flow meter can regulate an inlet gas pressure. The cell culture incubator can comprise a humidity control unit/sensor. The humidity control unit/sensor can be directly connected to the water humidity tray.

The enclosed environmental chamber of the cell culture incubator can comprise a sterilization unit, which can be a UV sterilization unit. The enclosed environmental chamber can comprise a pressurized door. The enclosed environmental chamber can comprise a sensor that provides a detectable alarm upon detection of an oxygen level of the enclosed environmental chamber that differs by more than about ±0.5% from a user-desired oxygen level. The enclosed environmental chamber can comprise a sensor that provides a detectable alarm upon detection of an atmospheric pressure of the enclosed environmental chamber that differs by more than about ±0.5% from a user-desired atmospheric pressure. The enclosed environmental chamber can comprise a user display that displays an atmospheric pressure level of the enclosed environmental chamber. In some embodiments, the enclosed environmental chamber comprises a user display that displays an O2 level of the enclosed environmental chamber. In some embodiments, the enclosed environmental chamber comprises a user display which displays a CO2 level of the enclosed environmental chamber. In some embodiments, the enclosed environmental chamber comprises a user display which displays a temperature level of the enclosed environmental chamber.

A user can program the cell culture incubator to mimic, for example, physiological, tumor microenvironment, hypoxic, high pressure, low pressure, or supraphysiological conditions. The cell culture incubator can be configured to calibrate to the conditions set by the user within about one minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 30 minutes, about 35 minutes, about 40 minutes, about 45 minutes, about 50 minutes, about 55 minutes, or about one hour. In some embodiments, the cell culture incubator can reach the desired conditions set by the user in less than about 20 minutes. In some embodiments, the cell culture incubator can reach the desired conditions set by the user in about 20 minutes. In some embodiments, the cell culture incubator can reach the desired conditions set by the user within 20 minutes.

In some embodiments, the enclosed environmental chamber occupies no more than 6 cubic feet of space. In some embodiments, the enclosed environmental chamber occupies no more than 3.5 cubic feet of space. In some embodiments, the enclosed environmental chamber occupies no more than 2 cubic feet of space. In some embodiments, the enclosed environmental chamber occupies no more than 1.5 cubic feet of space. In some embodiments, the enclosed environmental chamber occupies no more than 1 cubic foot of space. In some embodiments, the enclosed environmental chamber occupies less than 1 cubic foot of space. In some embodiments, the cell culture plate comprises 1, 6, 12, 24, 48, 96, 384, 1056, 1536, or 3456 wells.

Figure 19:
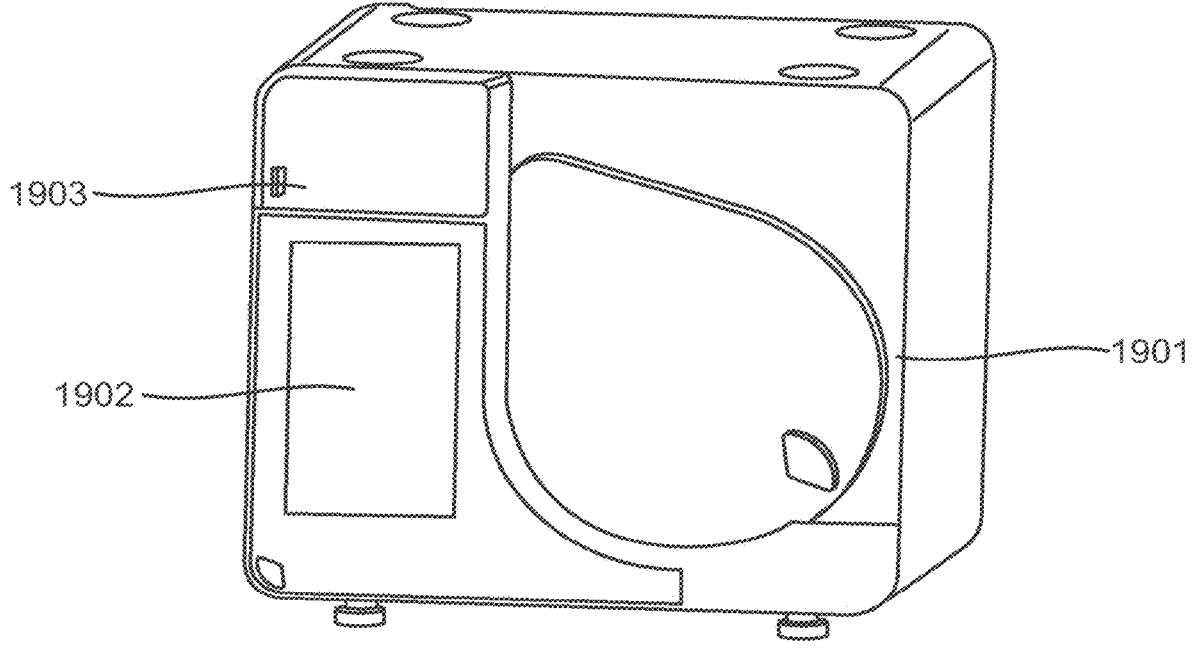
FIG. 19 displays an illustrative cell culture incubator of the invention.

A method of the invention can employ a cell culture incubator for culturing of a target cell population. FIG. 19 provides an illustrative example of a cell culture incubator that can be used in a system of the invention. 1901 is the door of the incubator that can be opened to place a cell culture in the incubator. 1902 is a control unit that can be used to program the cell culture incubator using parameters including, for example, temperature, humidity, oxygen level, carbon dioxide level, time of incubation, nitrogen level, and chamber pressure. 1903 is a USB port that can be used to input data to or extract data from the cell culture incubator.

Figure 20:
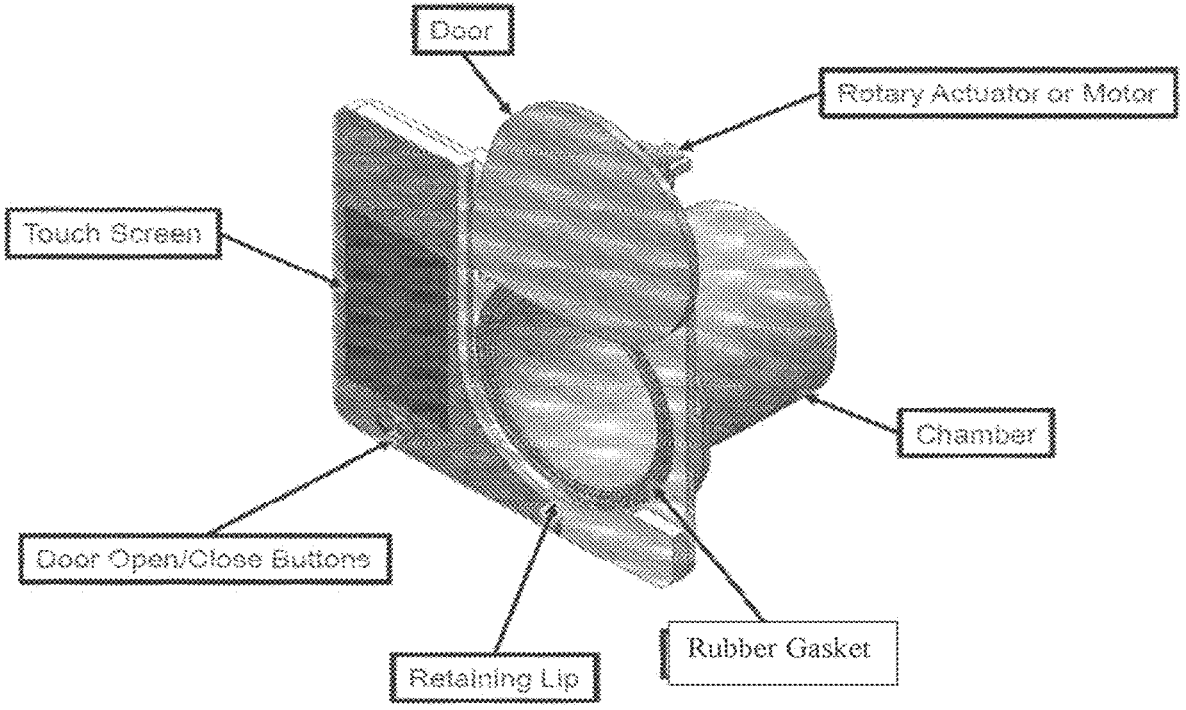
FIG. 20 displays a door configuration of a cell culture incubator of the invention.
Figure 21:
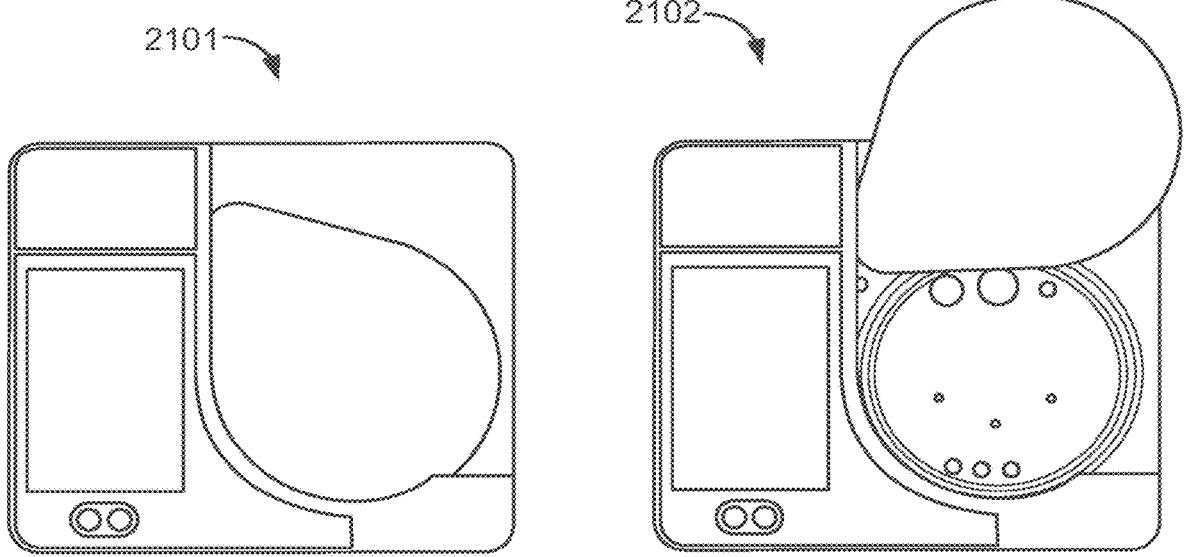
FIG. 21 displays a door configuration of a cell culture incubator of the invention.
Figure 22:
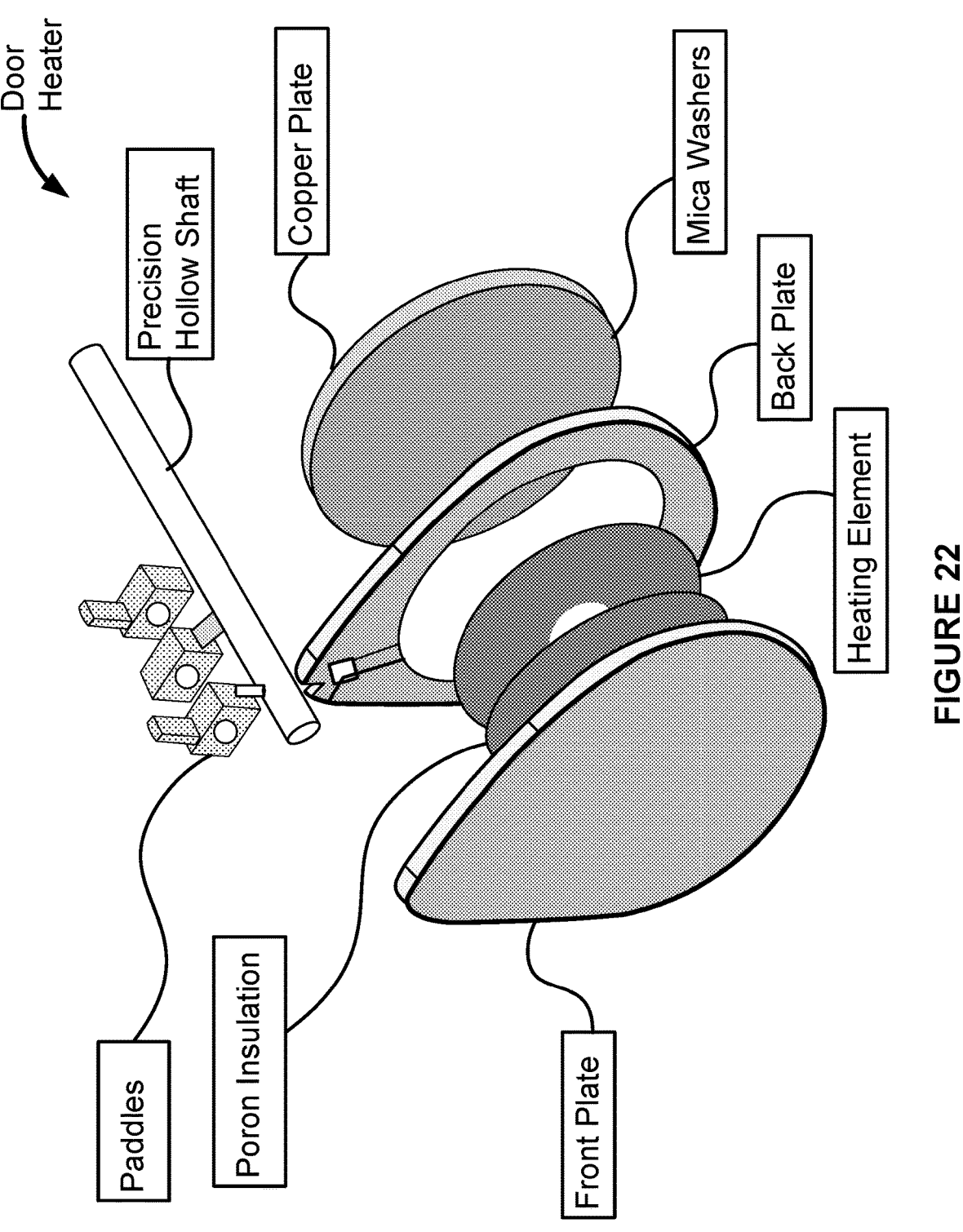
FIG. 22 depicts a door heater of a cell culture incubator of the invention.

FIG. 20 is a diagram of the front of the cell culture incubator. FIG. 20 depicts the door, a rubber gasket around the edge of the door that can fit tightly using a door handle latch, retaining lip, open and close buttons for the door, touch screen, rotary actuator or motor, and chamber of the incubator. FIG. 21 shows the cell culture incubator door closed (2101) and open (2102). FIG. 22 depicts a door heater than can be used in a system of the invention. The figure shows the front plate, heating element, poron insulation, back plate, mica washers, copper plate, precision hollow shaft, and paddles that can be used to heat the cell culture incubator to a desired temperature.

The height, width, depth, or length of the cell culture incubator can be, for example, about 6 in, about 6.5 in, about 7 in, about 7.5 in, about 8 in, about 8.5 in, about 9 in, about 9.5 in, about 10 in, about 10.5 in, about 11 in, about 11.5 in, about 12 in, about 12.1 in, about 12.2 in, about 12.3 in, about 12.4 in, about 12.5 in, about 12.6 in, about 12.7 in, about 12.8 in, about 12.9 in, about 13 in, about 13.1 in, about 13.2 in, about 13.3 in, about 13.4 in, about 13.5 in, about 13.6 in, about 13.7 in, about 13.8 in, about 13.9 in, about 14 in, about 14.5 in, about 15 in, about 15.5 in, about 16 in, about 16.5 in, about 17 in, about 17.5 in, about 18 in, about 18.5 in, about 19 in, about 19.5 in, about 20 in, about 20.5 in, about 21 in, about 21.5 in, about 22 in, about 22.5 in, about 23 in, about 23.5 in, about 24 in, about 24.5 in, about 25 in, about 25.5 in, about 26 in, about 26.5 in, about 27 in, about 27.5 in, about 28 in, about 28.5 in, about 29 in, about 29.5 in, about 30 in, about 30.5 in, about 31 in, about 31.5 in, about 32 in, about 32.5 in, about 33 in, about 33.5 in, about 34 in, about 34.5 in, about 35 in, about 35.5 in, about 36 in, about 36.5 in, about 37 in, about 37.5 in, about 38 in, about 38.5 in, about 39 in, about 39.5 in, about 40 in, about 40.5 in, about 41 in, about 41.5 in, about 42 in, about 42.5 in, about 43 in, about 43.5 in, about 44 in, about 44.5 in, about 45 in, about 45.5 in, about 46 in, about 46.5 in, about 47 in, about 47.5 in, about 48 in, about 48.5 in, about 49 in, about 49.5 in, about 50 in, about 50.5 in, about 51 in, about 51.5 in, about 52 in, about 52.5 in, about 53 in, about 53.5 in, about 54 in, about 54.5 in, about 55 in, about 55.5 in, about 56 in, about 56.5 in, about 57 in, about 57.5 in, about 58 in, about 58.5 in, about 59 in, about 59.5 in, about 60 in, or any combination thereof.

In some embodiments, the height of the cell culture incubator is 12 in. In some embodiments, the width of the cell culture incubator is 13.5 in. In some embodiments, the depth of the cell culture incubator is 13.1 in.

The capacity of the enclosed environmental chamber can be, for example, about 100 inch3, about 110 inch3, about 120 inch3, about 130 inch3, about 140 inch3, about 150 inch3, about 160 inch3, about 170 inch3, about 180 inch3, about 190 inch3, about 200 inch3, about 205 inch3, about 210 inch3, about 211 inch3, about 212 inch3, about 213 inch3, about 214 inch3, about 215 inch3, about 216 inch3, about 217 inch3, about 218 inch3, about 219 inch3, about 220 inch3, about 221 inch3, about 222 inch3, about 223 inch3, about 224 inch3, about 225 inch3, about 226 inch3, about 227 inch3, about 228 inch3, about 229 inch3, about 230 inch3, about 240 inch3, about 250 inch3, about 260 inch3, about 270 inch3, about 280 inch3, about 290 inch3, about 300 inch3, about 310 inch3, about 320 inch3, about 330 inch3, about 340 inch3, about 340 inch3, about 350 inch3, about 360 inch3, about 370 inch3, about 380 inch3, about 390 inch3, about 400 inch3, about 420 inch3, about 440 inch3, about 460 inch3, about 480 inch3, or about 500 inch3. In some embodiments, the capacity of the enclosed environmental chamber is about 220 inch3. In some embodiments, the capacity of the enclosed environmental chamber is about 221 inch3. In some embodiments, the capacity of the enclosed environmental chamber is about 222 inch3. In some embodiments, the capacity of the enclosed environmental chamber is about 223 inch3. In some embodiments, the capacity of the enclosed environmental chamber is about 224 inch3. In some embodiments, the capacity of the enclosed environmental chamber is 224 inch3.

Materials that can be used in the manufacture of the cell culture incubator include, for example, stainless steel, glass, copper, silver, gold, plastic, blanket batting, hard-board insulation, or any combination thereof. The enclosed environmental chamber can be made of, for example, copper or stainless steel. In some embodiments, the enclosed environmental chamber is made of copper.

The cell culture incubator can be maintained at a desired humidity level. The humidity level can be, for example, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 90.5%, about 91%, about 91.5%, about 92%, about 92.5%, about 93%, about 93.5%, about 94%, about 94.5%, about 95%, about 95.5%, about 96%, about 96.5%, about 97%, about 97.5%, about 98%, about 98.5%, about 99%, about 99.5%, or about 99.9%.

The CO2 levels in the cell culture incubator can be, for example, about 10%, about 9.5%, about 9%, about 8.5%, about 8%, about 7.5%, about 7%, about 6.9%, about 6.8%, about 6.7%, about 6.6%, about 6.5%, about 6.4%, about 6.3%, about 6.2%, about 6.1%, about 6%, about 5.9%, about 5.8%, about 5.7%, about 5.6%, about 5.5%, about 5.4%, about 5.3%, about 5.2%, about 5.1%, about 5%, about 4.9%, about 4.8%, about 4.7%, about 4.6%, about 4.5%, about 4.4%, about 4.3%, about 4.2%, about 4.1%, about 4%, about 3.9%, about 3.8%, about 3.7%, about 3.6%, about 3.5%, about 3.4%, about 3.3%, about 3.2%, about 3.1%, about 3%, about 2.9%, about 2.8%, about 2.7%, about 2.6%, about 2.5%, about 2.4%, about 2.3%, about 2.2%, about 2.1%, about 2%, about 1.9%, about 1.8%, about 1.7%, about 1.6%, about 1.5%, about 1.4%, about 1.3%, about 1.2%, about 1.1%, about 1%, about 0.9%, about 0.8%, about 0.7%, about 0.6%, about 0.5%, about 0.4%, about 0.3%, about 0.2%, or about 0.1%.

The cell culture incubator can be used in combination with the culturing conditions described herein, for example, to isolate specific cell populations, to induce changes in cells, to introduce exogenous materials into cells, to determine biomarker expression, and as a diagnostic tool for patients.

The methods of the invention can be used to increase, for example, transfection and transduction efficiency in cells. Transduction can be used, for example, to introduce a viral vector in a cell. Viral nucleic acid delivery systems can use recombinant viruses to deliver nucleic acids for gene therapy. Non-limiting examples of viruses that can be used to deliver nucleic acids include retrovirus, adenovirus, herpes simplex virus, adeno-associated virus, vesicular stomatitis virus, reovirus, vaccinia, pox virus, and measles virus.

Transfection methods that can be used with methods of the invention include, for example, lipofection, electroporation, calcium phosphate transfection, chemical transfection, polymer transfection, gene gun, magnetofection, or sonoporation. The transfection can be a stable or transient transfection. The transfection can be used to transfect DNA plasmids, RNA, siRNA, shRNA, or any nucleic acid. The plasmids can encode, for example, green fluorescent protein (GFP), selectable markers, and other proteins of interest. The selectable markers can provide resistance to, for example, G418, hygromycin B, puromycin, and blasticidin. The transfection method used with a method of the invention can further introduce a vector system encoding the CRISPR-Cas9 system into a cell.

A method of the invention can increase the transfection or transduction efficiency by, for example, about 2-fold, about 3-fold, about 4-fold, about 5-fold, about 6-fold, about 7-fold, about 8-fold, about 9-fold, about 10-fold, about 12-fold, about 14-fold, about 16-fold, about 18-fold, about 20-fold, about 25-fold, about 30-fold, about 35-fold, about 40-fold, about 45-fold, about 50-fold, about 60-fold, about 70-fold, about 80-fold, about 90-fold, or about 100-fold.

Therapeutic Uses

Subjects can be, for example, elderly adults, adults, adolescents, pre-adolescents, children, toddlers, infants. Subjects can be non-human animals, for example, a subject can be a mouse, rat, cow, horse, donkey, pig, sheep, dog, cat, or goat. A subject can be a patient.

A method of the invention can be used to treat or diagnose, for example, cancer in a subject. A method of the invention can be used to identify a therapeutic, a biomarker, a genetic mutation, an epigenetic marker, or a therapeutic target for cancer. A method of the invention can also be used to develop a library or database of genetic mutations found in cancer. A method of the invention can be used for personalized medicine. A method of the invention can be used to determine the effect of a therapeutic on a specific cell type.

A method of the invention can be used, for example, to enrich specific populations of cells or induce expression of specific genes, for example, biomarkers or epigenetic markers. A method of the invention can be used, for example, to affect the potency of stem cells or somatic cells. For example, a method of the invention can be used to test the ability of stem cells to go from, for example, totipotent to, for example, pluripotent, oligopotent, or unipotent.

The change in gene expression can affect, for example, cell quantity, cell morphology, cell growth, cell motility, cell invasion, or cell adhesion.

Genomic, proteomic, and metabolic analysis can be conducted on the cultured cells to, for example, identify biomarkers that can be used for development of cancer therapies, drug development, cancer vaccines, cancer screening, diagnostics, personalized antibody development, hematopoietic stem cell transplantation, organ transplantation, or cardiovascular disease treatment.

Non-limiting examples of cancers that can be analyzed in a method of the invention include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/-malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

Cell surface marker molecules, such as EPCAM, CD133, EGFR, HER2, or CD20 can be used to identify a population of cells. In some embodiments, a combination of cell surface markers, or a cell surface marker signature, can be used to identify a population of cells. In some embodiments, a cell surface marker, and/or a cell surface marker signature can be used in medical diagnosis.

Epigenetic markers that can be assessed using a method of the invention include, for example, DNA methylation, cytosine methylation, hydroxymethylation, histone methylation, lysine acetylation, lysine methylation, arginine methylation, serine phosphorylation, threonine phosphorylation, protein phosphorylation, protein ubiquitination, protein sumoylation, presence of 5-methylcytosine, histone H3 acetylation, or histone H4 acetylation.

Methods that can be used to determine the presence of biological markers include, for example, qPCR, RT-PCR, immunofluorescence, immunohistochemistry, western blotting, high-throughput sequencing, ELISA, or mRNA sequencing.

Target cell subpopulations can be used for personalized medicine. For example, CTCs and CSCs can be used for chemosensitivity testing whereby chemotherapy regimens can be tested on cultured CTCs. An assessment of the effects of chemotherapy drugs on CTCs including, for example, cell viability and cell division, can be done to determine the efficacy of a given drug.

The methods of the present invention can be used to monitor subject response to a given cancer therapy conducted by serial monitoring of the subject's CTC population as treatment progresses. Blood samples can be analyzed on a regular basis, before, during, and after treatment to assess CTC viability.

The methods of the invention can be used to monitor subjects who are currently in remission to investigate the potential of cancer relapse. Serial testing of subject blood for CTCs can be conducted on a regular basis to determine the potential or likelihood for cancer relapse. In some cases, serial testing can result in earlier detection of relapse. Serial testing can also be used for long-term longitudinal studies.

A method of the invention can be used to collect data about patients for patient stratification during clinical trials. For example, the presence of a specific biomarker found in a patient's CTCs can be used to place the patient in appropriate clinical trial groups, or can be used as exclusion criteria for other clinical trial groups.

The invention described herein can provide data that can be used for a medical professional to treat a patient. Treatment of a patient can include diagnosis, prognosis or theranosis. Diagnoses can comprise determining the condition of a patient. Diagnosis can be conducted at one time point or on an ongoing basis. For example, a patient can be diagnosed with cancer. In another example, a cancer patient who is in remission can be routinely screened to determine if a cancer relapse has occurred. Prognosis can comprise determining the outcome of a patient's disease, the chance of recovery, or how the disease will progress. For example, identifying CTCs of a certain type can provide information upon which a prognosis can be based. Theranosis can comprise determining a therapy treatment. For example, a patient's cancer therapy treatment can include chemotherapy, radiation, drug treatment, no treatment, or any combination thereof. A patient can be monitored, for example by serial blood testing, to measure CTC populations before, during and after a patient undergoes treatment. A positive response to therapy can result in a decreased CTC viability and lower division rates.

Computer Systems

A method of the invention can be used to, for example, sequence, image, or characterize the collected target cell subpopulations. Further methods can be found in PCT/US14/13048, the entirety of which is incorporated herein by reference.

Figure 4:
FIG. 4 is an illustrative computer system to be used with a method of the invention.
Figure 4:
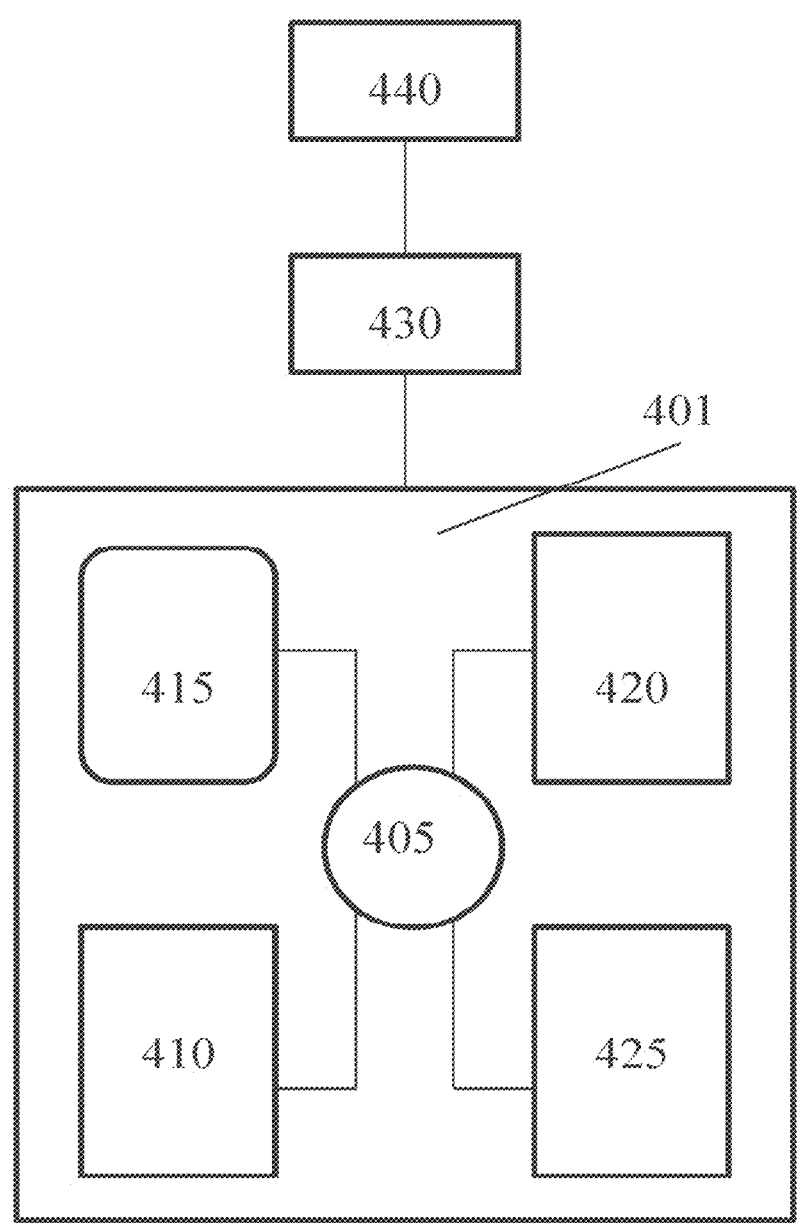

The invention provides a computer system that is configured to implement the methods of the disclosure. The system can include a computer server ("server") that is programmed to implement the methods described herein. FIG. 4 depicts a system 400 adapted to enable a user to detect, analyze, and process images of cells and sequence cells. The system 400 includes a central computer server 401 that is programmed to implement exemplary methods described herein. The server 401 includes a central processing unit (CPU, also "processor") 405 which can be a single core processor, a multi core processor, or plurality of processors for parallel processing. The server 401 also includes memory 410 (e.g. random access memory, read-only memory, flash memory); electronic storage unit 415 (e.g. hard disk); communications interface 420 (e.g. network adaptor) for communicating with one or more other systems; and peripheral devices 425 which may include cache, other memory, data storage, and/or electronic display adaptors. The memory 410, storage unit 415, interface 420, and peripheral devices 425 are in communication with the processor 405 through a communications bus (solid lines), such as a motherboard. The storage unit 415 can be a data storage unit for storing data. The server 401 is operatively coupled to a computer network ("network") 430 with the aid of the communications interface 420. The network 430 can be the Internet, an intranet and/or an extranet, an intranet and/or extranet that is in communication with the Internet, a telecommunication or data network. The network 430 in some cases, with the aid of the server 401, can implement a peer-to-peer network, which may enable devices coupled to the server 401 to behave as a client or a server. The microscope and micromanipulator can be peripheral devices 425 or remote computer systems 440.

The storage unit 415 can store files, such as individual images, time lapse images, data about individual cells, cell colonies, or any aspect of data associated with the invention. The data storage unit 415 may be coupled with data relating to locations of cells in a virtual grid.

The server can communicate with one or more remote computer systems through the network 430. The one or more remote computer systems may be, for example, personal computers, laptops, tablets, telephones, smart phones, or personal digital assistants.

In some situations the system 400 includes a single server 401. In other situations, the system includes multiple servers in communication with one another through an intranet, extranet and/or the Internet.

The server 401 can be adapted to store cell profile information, such as, for example, cell size, morphology, shape, migratory ability, proliferative capacity, kinetic properties, and/or other information of potential relevance. Such information can be stored on the storage unit 415 or the server 401 and such data can be transmitted through a network.

Methods as described herein can be implemented by way of machine (e.g., computer processor) computer readable medium (or software) stored on an electronic storage location of the server 401, such as, for example, on the memory 410, or electronic storage unit 415. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410. Alternatively, the code can be executed on a second computer system 440.

Aspects of the systems and methods provided herein, such as the server 401, can be embodied in programming. Various aspects of the technology may be thought of as "products" or "articles of manufacture" typically in the form of machine (or processor) executable code and/or associated data that is carried on or embodied in a type of machine readable medium (e.g., computer readable medium). Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, tangible storage medium, a carrier wave medium, or physical transmission medium. Non-volatile storage media can include, for example, optical or magnetic disks, such as any of the storage devices in any computer(s) or the like, such may be used to implement the system. Tangible transmission media can include: coaxial cables, copper wires, and fiber optics (including the wires that comprise a bus within a computer system). Carrier-wave transmission media may take the form of electric or electromagnetic signals, or acoustic or light waves such as those generated during radio frequency (RF) and infrared (IR) data communications. Common forms of computer-readable media therefore include, for example: a floppy disk, a flexible disk, hard disk, magnetic tape, any other magnetic medium, a CD-ROM, DVD, DVD-ROM, any other optical medium, punch cards, paper tame, any other physical storage medium with patterns of holes, a RAM, a ROM, a PROM and EPROM, a FLASH-EPROM, any other memory chip or cartridge, a carrier wave transporting data or instructions, cables, or links transporting such carrier wave, or any other medium from which a computer may read programming code and/or data. Many of these forms of computer readable media may be involved in carrying one or more sequences of one or more instructions to a processor for execution.

Gas Flow Regulation System

Embodiments of the cell culture incubator include sensors for atmospheric parameters such as oxygen, carbon dioxide, total gas pressure, temperature, and dew point, each of which deliver sensory data to the control unit. Within the control unit, these data are received and acted upon by various atmospheric control modules such as an oxygen module, a pressure module, a carbon dioxide module, a temperature module, and a dew point module. By way of various control pathways, these modules each engage features and mechanics of a cell culture incubator gas flow system that operate to establish the atmospheric parameters within the incubators, such as individual gas sources, flow lines, flow valves, pumps, and vents.

FIGS. 24A-24B depict embodiments of a gas flow system 2400 for a cell culture incubator that control the flow of various gases into enclosed environment chamber 2401 in order to regulate aspects of the gaseous or atmospheric environment within the chamber. These parameters particularly include the total gas pressure and the oxygen concentration of the total gas composition, but further may include carbon dioxide, nitrogen, and water vapor. FIG. 24A is a schematic diagram of an embodiment of gas flow control system 2400 to be used with a cell culture incubator and a method of the invention. FIG. 24B is schematic diagram of an embodiment of a nitrogen flow system 2450 (which may be considered a subsystem of gas flow control system 2400) to be used with a cell culture incubator and a method of the invention. Embodiments of the invention, per systems as depicted in FIGS. 24A-24B, are directed toward creating cell culture conditions that include both low oxygen and high pressure, both parameters being regulated independently of each other.

FIGS. 24A-24B show major components of system 2400 and 2450, respectively, which include an incubator chamber 2401, a chamber door 2416 (FIG. 24B) an incubator chamber heater 2402, an air injection pump 2403, a recirculation pump 2404, a display 2405, and a control unit 2406. Label 2401 refers to a cell culture incubator's enclosed environmental chamber, but, for simplicity, may also refer more generally to an incubator as a whole. Both pumps 2403 and 2404 are in operative communication with the interior of enclosed incubator chamber 2401. As described earlier in the disclosure, embodiments of the cell culture incubator and its control systems are typically controlled by way of user input via a user interface (FIG. 15), and by automatic action of pumps and valves by way of sensory feedback from within the incubator chamber 2401, as mediated by control unit 2406 and its component control modules, as described further below.

Gas flow into and out of enclosed environmental chamber 2401 by way of gas control system 2400 includes controlled input of nitrogen gas 2434, controlled input of carbon dioxide 2432, and controlled input of air 2436 (by way of injection pump 2403). The internal atmosphere within the incubator also has an influx and efflux by way of recirculation pump 2404, which facilitates a homogeneous mixing of gases within enclosed environmental chamber 2401. Influx of nitrogen, carbon dioxide, and air, by way of their respective pumps, is controlled by way of control unit 2406, by way of sensors and gas control modules, as described below.

A number of types of sensors may be included within incubator chamber 2401 that are responsive to various atmospheric conditions, and which transmit sensed data to control unit 2406 and its various control modules. These sensors include an oxygen sensor 2410, a carbon dioxide sensor 2411, a pressure sensor 2412, a temperature probe 2413, a dew point sensor 2414. In some embodiments of system 2400, one or more pressure sensors may be included that are disposed and configured to measure external ambient atmospheric pressure. Various types of oxygen sensors are commercially available and suitable for embodiments of the invention. For example, AMI (Huntington Beach, CA) manufacturers an oxygen probe that delivers oxygen level data in terms of concentration. Instruments that deliver concentration data typically make use of a reference gas or reference to ambient air. Another example of a suitable oxygen probe is provided by SST (Coatbridge, UK), which delivers oxygen level data in terms of partial pressure. Control unit 2406 (via display 2405) provides oxygen level data in terms of concentration, even if sensor data reports oxygen partial pressure. Most fundamentally, the basic oxygen parameter is its partial pressure, which can be expressed either directly or by conversion, or by comparison to reference data, as a relative percent of a total atmospheric composition.

In a typical embodiment, data from dew point sensor is directed by control unit 2406 to display 2405, and in some embodiments, control of humidity is passive (as for example when humidity is maintained by way of evaporation of liquid water in the enclosed chamber) without the intervention of a dedicated control module.

A contact sensor 2475 (FIG. 24B) may also disposed at a site interfacing between chamber door 2416 that is sensitive to contact between the door and its frame. In one embodiment, for example, contact sensor 2475 is a depressable button that operates valve 2474. The role of valve 2474 in controlling gas input, particularly nitrogen input, into incubator chamber 2401 is described further below.

Within control unit 2406 are several control modules; these include an oxygen module 2420, a carbon dioxide module 2422, a pressure module 2424, and a temperature module 2426. Each of these modules receive sensory input from their corresponding sensors, i.e., oxygen sensor 2410, carbon dioxide sensor 2411, pressure sensor 2412, and temperature probe 2413, respectively. Signals from each of these types of sensor are received by corresponding modules and used to formulate instructions that are sent to the various gas flow control mechanisms and pumps, as described herein, to achieve the instructed atmospheric parameters. Sensor values, or an algorithm-derived expression thereof, may also be shown in display 2405, as exemplified by FIGS. 16-18.

Control unit 2406 effects control of the atmospheric environment within enclosed environmental chamber 2401 by several control paths. Display control path 2441 informs the read out on display 2405. Heater path 2443 is responsive to temperature module 2426, and controls the operation of heater 2402. Recirculation pump 2404 operates at a constant rate that can be set, but is typically not subject to sensory feedback control.

Gas control path 2442 is shown in a simplified depiction as a single line, but it represents control paths for the operation of nitrogen 2434 inflow, carbon dioxide 2432 inflow, vent efflux 2438 control, and air 2436 injection by way of air injection pump 2403. The control of nitrogen inflow, carbon dioxide inflow, gas efflux through the vent, and air inflow are all controlled more particularly by valves or flow regulators that are not shown for the sake of simplicity. Nitrogen 2434 inflow control is responsive to oxygen module 2420 and pressure module 2424. Injection of nitrogen may be used both to increase pressure within enclosed environmental chamber 2401 and to decrease the oxygen concentration, as described further below.

In typical operation, cell culture incubator 2401 operates at an oxygen level that ranges from an ambient oxygen level to a lower oxygen level, as described earlier. Although some embodiments of incubator 2401 may be configured to operate at oxygen levels higher than ambient levels, typical embodiments of incubator do not. A typical operational task, therefore, is to decrease oxygen concentration to a level less than that of the ambient condition. This oxygen-lowering task is accomplished primarily by injection of nitrogen 2434, which is controlled by control unit 2406 with input from the oxygen module 2420. If the oxygen level drifts to level higher than a targeted or instructed level, nitrogen injected into enclosed environmental chamber 2401 mixes with existing gas composition and drives the oxygen level by dilution. Once the instructed oxygen level is achieved, control unit 2406 shuts off nitrogen injection.

Referring now particularly to FIG. 24B, and returning to a description of a gas driven safety lock mechanism 2472. For orientation, it can be seen that as a gas such as nitrogen 2434 enters the incubator, it splits into two paths: a chamber gas flow path 2460 and a door lock control path 2470. Chamber gas flow path 2460 includes intervention of regulator 2462 and valve 2464. Details of the control of chamber gas flow path are covered above in the description of gas control system 2400 as a whole, and as shown in FIG. 24A.

The operation of a cell culture incubator at a higher-than-ambient total gas pressure is benefited from a construction that is fortified against gas leakage, and which allows a door to the incubator to opened safely, without undue disturbance of the atmosphere within the incubator, undue disruption of gas regulation controls, and without unnecessary loss of gas that being injected in to enclosed environmental chamber 2401. Accordingly, some embodiments of the cell culture incubator include a door 2416 to the enclosed environmental chamber and a safety lock 2472 configured to prevent opening of the door when the enclosed environmental chamber is in a pressurized condition.

Some of these the safety lock embodiments 2472 include a piston configured to be able to assume a locked position and an unlocked position, the locked position of the safety lock being secured by a gas pressure behind the piston, and the unlocked position being assumed by a release of such gas pressure. In some of these embodiments, the gas pressure is provided by nitrogen, the nitrogen being delivered to a piston chamber behind the piston, the nitrogen being provided to the chamber by way of a piston gas flow control path 2470 from the nitrogen source. Use of nitrogen for the purpose of driving door control path 2470 is a practical choice; but oxygen or carbon dioxide, or any other gas being put into the system would also work. Nitrogen is practical for this use because it is already used in relatively high volume and because release of nitrogen into the atmosphere is benign.

Tracking the elements of door lock control path 2470, it can be seen that nitrogen 2434 encounters locking piston 2472 which is configured to penetrate into enclosed environmental chamber door 2416 in its on position, the on position being secured by nitrogen pressure behind locking piston 2472. A contact sensor 2475 (as noted above in the context of enumerating the various sensors in the system) is positioned at a point of contact between chamber door 2416 and its enclosing frame, such that it senses whether the door is open or closed, and communicates the open/closed status to controller 2406.

During operation of enclosed environmental chamber 2401, door 2416 is closed and locked by locking piston 2472. An opening sequence begins with user input to allow the door to open, in response, controller 2406 instructs valve 2474 to open, thereby stopping the flow of nitrogen into a chamber behind the piston, thereby releasing the pressure that supports the projection of the piston into door 2416, thereby allowing the door to be manually opened. In a locking sequence, contact sensor 2475 senses that the door has been closed, the controller opens valve 2474, thereby resuming the flow of nitrogen into the chamber behind the piston, thereby driving the front portion of locking piston 2472 into door 2416, and securely locking it shut.

Figure 18:
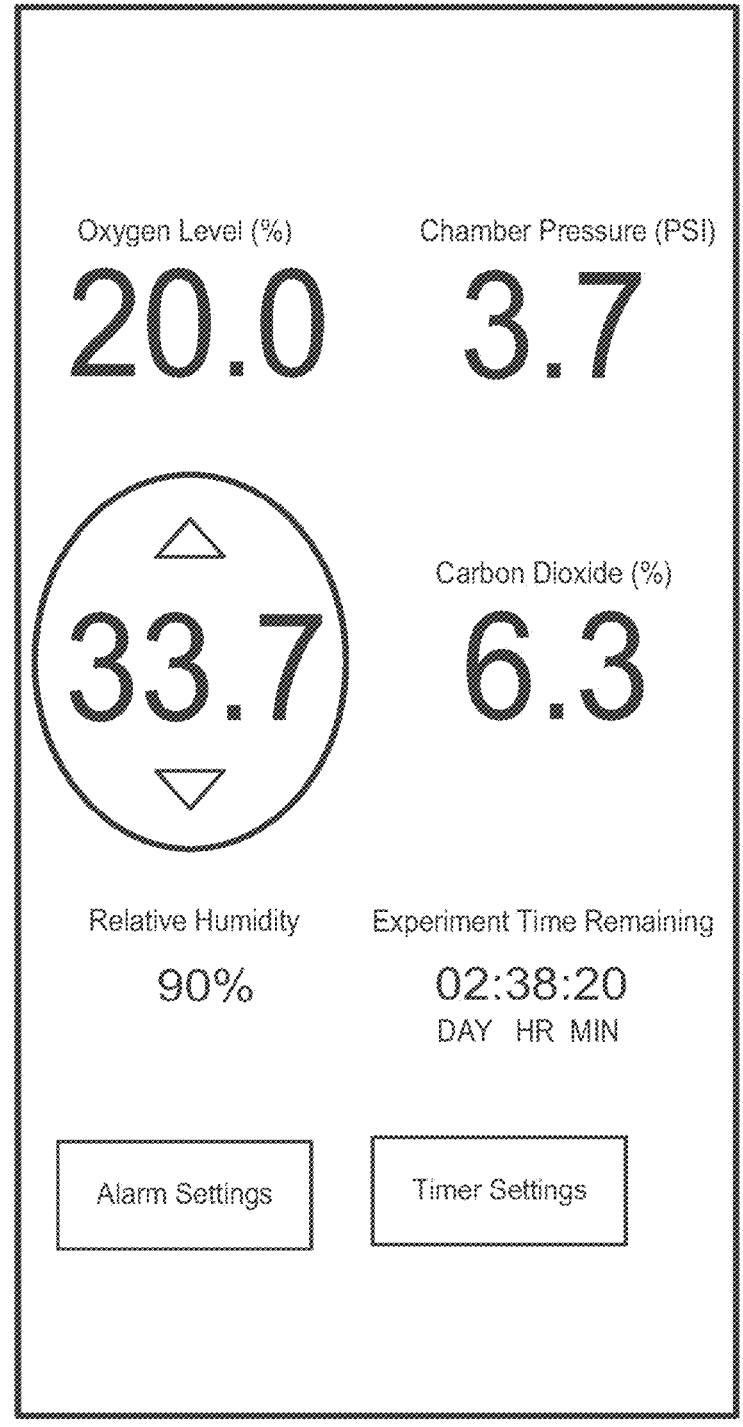
FIG. 18 depicts an illustrative user interface for a system of the invention.

Central to the operation of enclosed environment chamber 2401 and to the mission of controlling atmospheric or gaseous aspects of the environment for the purpose of creating particular effects on cultured cells is the formation of high fidelity and tunable atmosphere typically characterized by low oxygen (lower than the ambient level) and high pressure (higher than the ambient level), these two parameters being independently adjustable. It is noteworthy that the goal of instilling high pressure, in and of itself, inherently works against instilling low oxygen. Low oxygen is commonly and reasonably expressed as a percent, as, for example, can be read on display 2405, and as seen in FIGS. 16-18. In some embodiments, oxygen sensor 2410 is actually sensing a partial pressure of oxygen gas, an absolute term, not a relative % term. To derive an oxygen percent concentration, control unit 2406 considers both the partial pressure signal from oxygen sensor 2410 and either a total gas pressure signal or a reference gas, and by way of a formula delivers the "oxygen level %" value seen on display 2405.

In addition to oxygen partial pressure being the most basic oxygen level parameter, partial pressure is also the oxygen parameter of importance to cells in culture. Total gas pressure, by itself, is also a highly important atmospheric parameter for cells in culture, but it is separate from the effects of oxygen, as measured in partial pressure terms. This description of the oxygen level in terms of a fraction of the total gas pressure is being provided because it makes it clear that increasing the total gas pressure also, inherently, increases the partial pressure of any component gas species within the total gas composition. Accordingly, increasing total gas pressure increases the oxygen partial pressure, which is working against the goal of decreasing oxygen partial pressure. Accordingly, in embodiments of the invention, and to the extent that total gas pressure works to counter the goal of creating a low oxygen environment, instructions from control unit 2406 to create a low oxygen condition prevail despite the coincident instructions to create a high pressure condition.

EXAMPLES

Example 1: Identification of Markers Associated with Prostate Cancer

Figure 5:
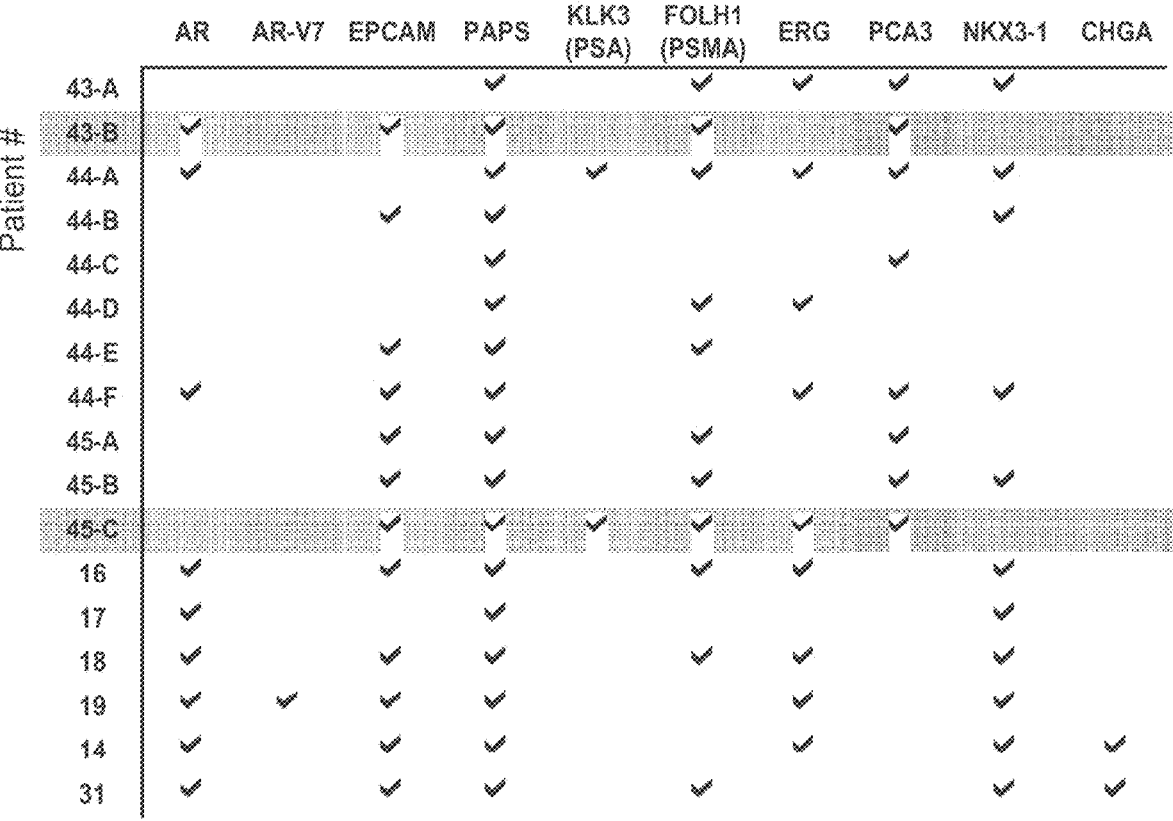
FIG. 5 depicts results of biomarker assessment in CTCs from prostate cancer cells.
Figure 5:
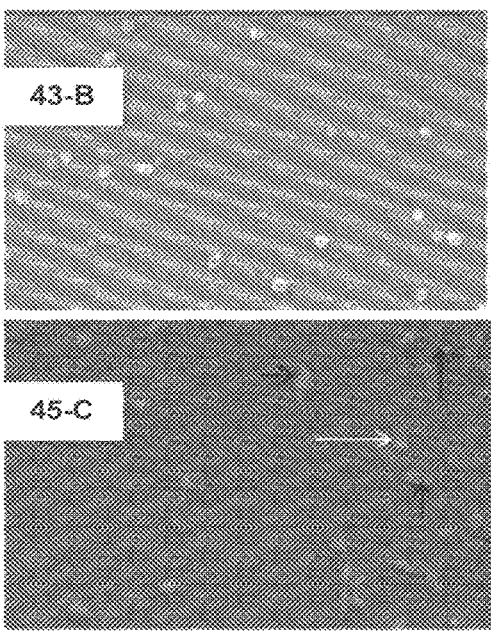

FIG. 5 shows the results of an experiment measuring expression levels of cancer-associated proteins using samples of CTCs obtained from a sample of patients with prostate cancer. The CTCs were grown and cultured according to a method of the invention to obtain an enriched CTC population. Gene expression of various markers associated with prostate cancer was assessed using qPCR. CD45 expression was assessed via immunofluorescence for two subjects, 43-B and 45-C. The white arrow indicates staining for CD45 and the black arrows indicate staining for EPCAM (epithelial cell adhesion molecule)/PSMA. The top panel only contains CD45 staining. The markers assessed included androgen receptor (AR), androgen receptor splice variant 7 (AR-V7), EPCAM, prostatic acid phosphatase (PAPS), prostate-specific antigen (KLK3/PSA), prostate-specific membrane antigen (FOLH1/PSMA), v-ets avian erythroblastosis virus E26 oncogene homolog (ERG), prostate cancer antigen 3 (PCA3), Nk3 homeobox 1 (NKX3-1), and chromogranin A or parathyroid secretory protein 1 (CHGA).

The results indicated that PAPS was expressed in all prostate tumor samples. The expression of other prostate cancer markers differed among the samples indicating that CTC colonies can be genetically diverse between subjects.

Example 2: Identification of Markers Associated with Prostate Cancer

Figure 6:
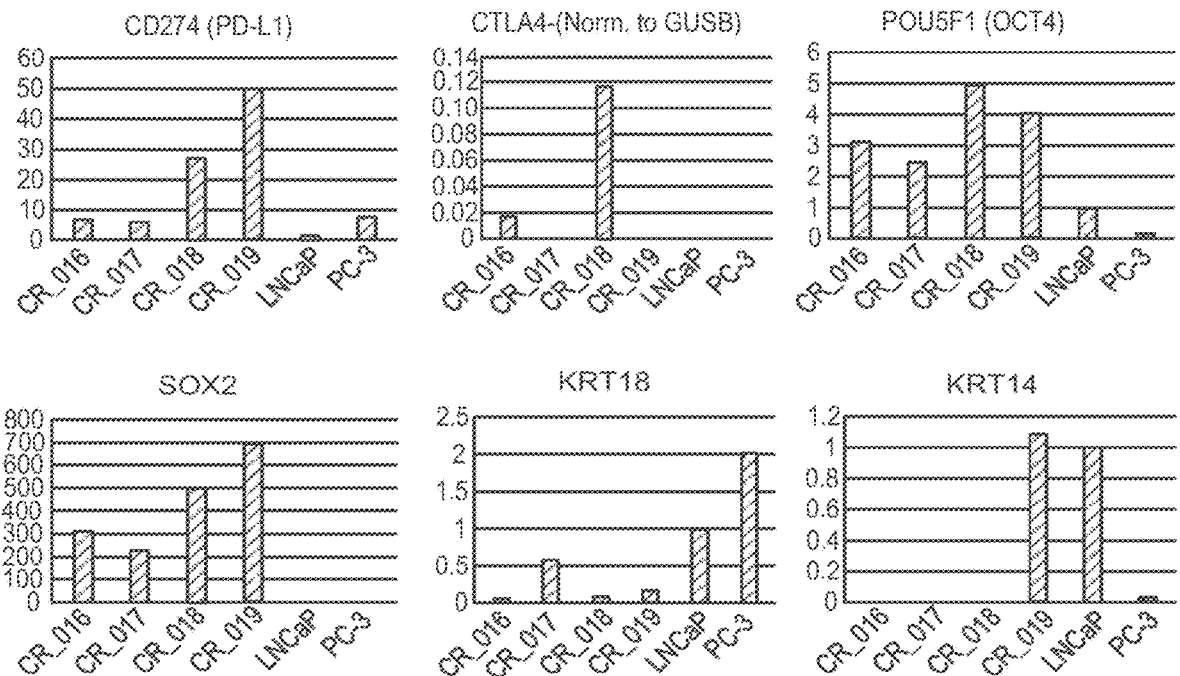
FIG. 6 shows results of biomarker determination for prostate cancer cells.
Figure 6:
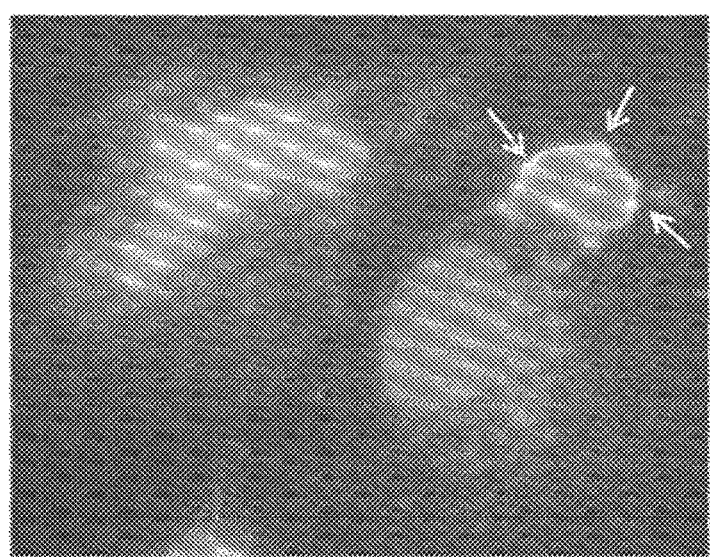

To identify immunotherapeutic targets and stem cell markers that can be expressed by prostate CTC colonies, 10 to 20 mL of peripheral blood was collected from over 30 subjects with metastatic CRPC (mCRPC). Eight of the subject samples yielded CTC colonies after culturing using a method of the invention as described in FIGS. 2-3. Four of the samples were used for qPCR analysis of several markers and were compared to the LNCaP (prostate adenocarcinoma) and PC-3 (prostate adenocarcinoma) cell lines as shows in FIG. 6, which contains the same staining pattern described for FIG. 1.

A representative immunofluorescence image is shown with DAPI, WBC, cytokeratin, and PSMA/PSA staining as in FIG. 1. The results indicated that several of the patient samples and cell lines expressed the immunotherapeutic targets programmed death ligand 1 (CD274/PD-L1) and cytotoxic T-lymphocyte-associated protein 4 (CTLA4) and the stem cell markers octamer-binding transcription factor 4 (PUSF1/Oct4), SRY (sex determining region Y)-box 2 (SOX2), keratin 18, type 1 (KRT18), and keratin 14, type 1 (KRT14), and that there was upregulation in Oct4, SOX2, and PD-L1.

Example 3: RNA Sequencing of Prostate Cancer CTC Colonies

Figure 7:
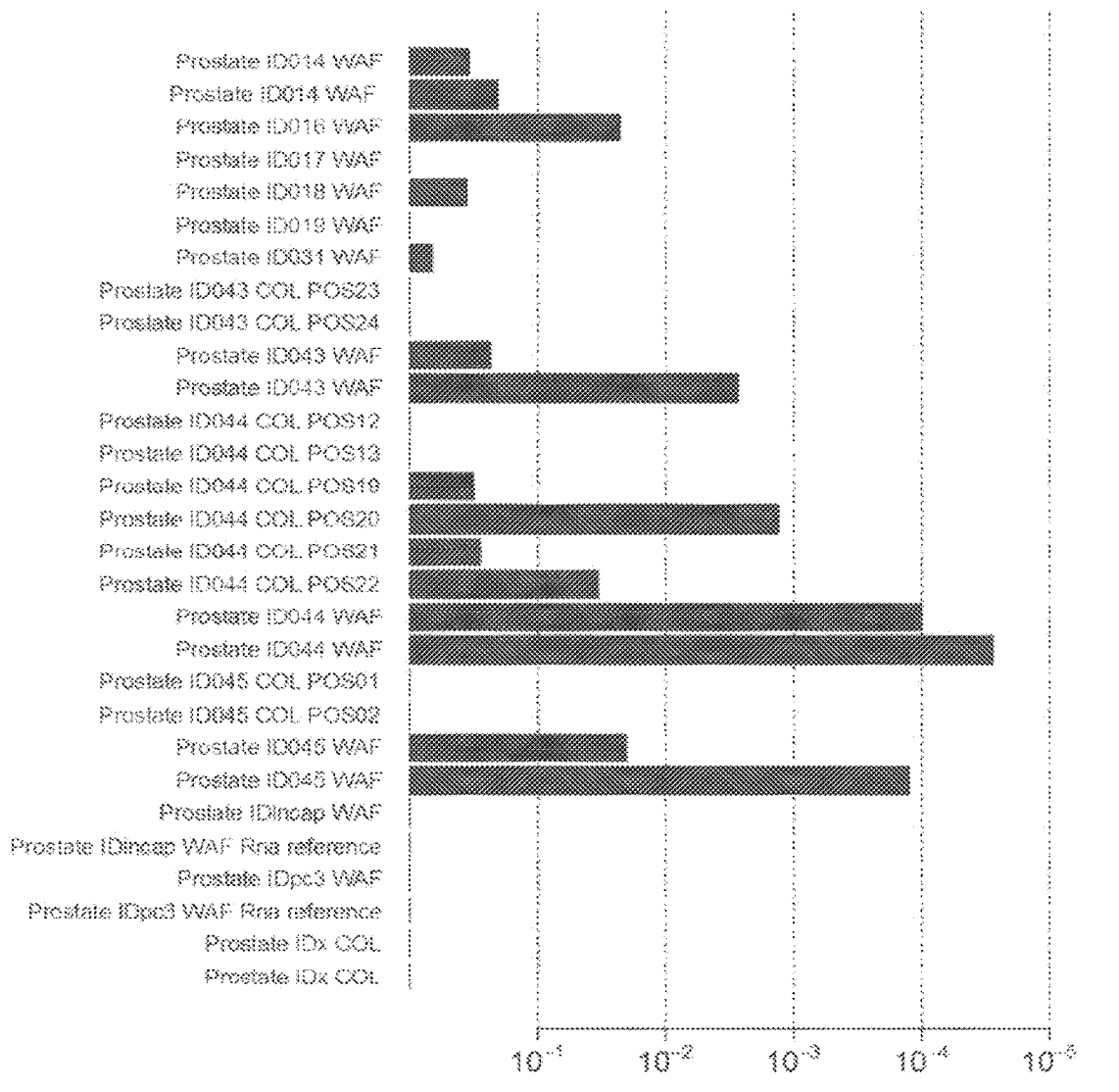
FIG. 7 displays results of mRNA sequencing analysis for the nerve growth factor signaling pathway.
Figure 8:
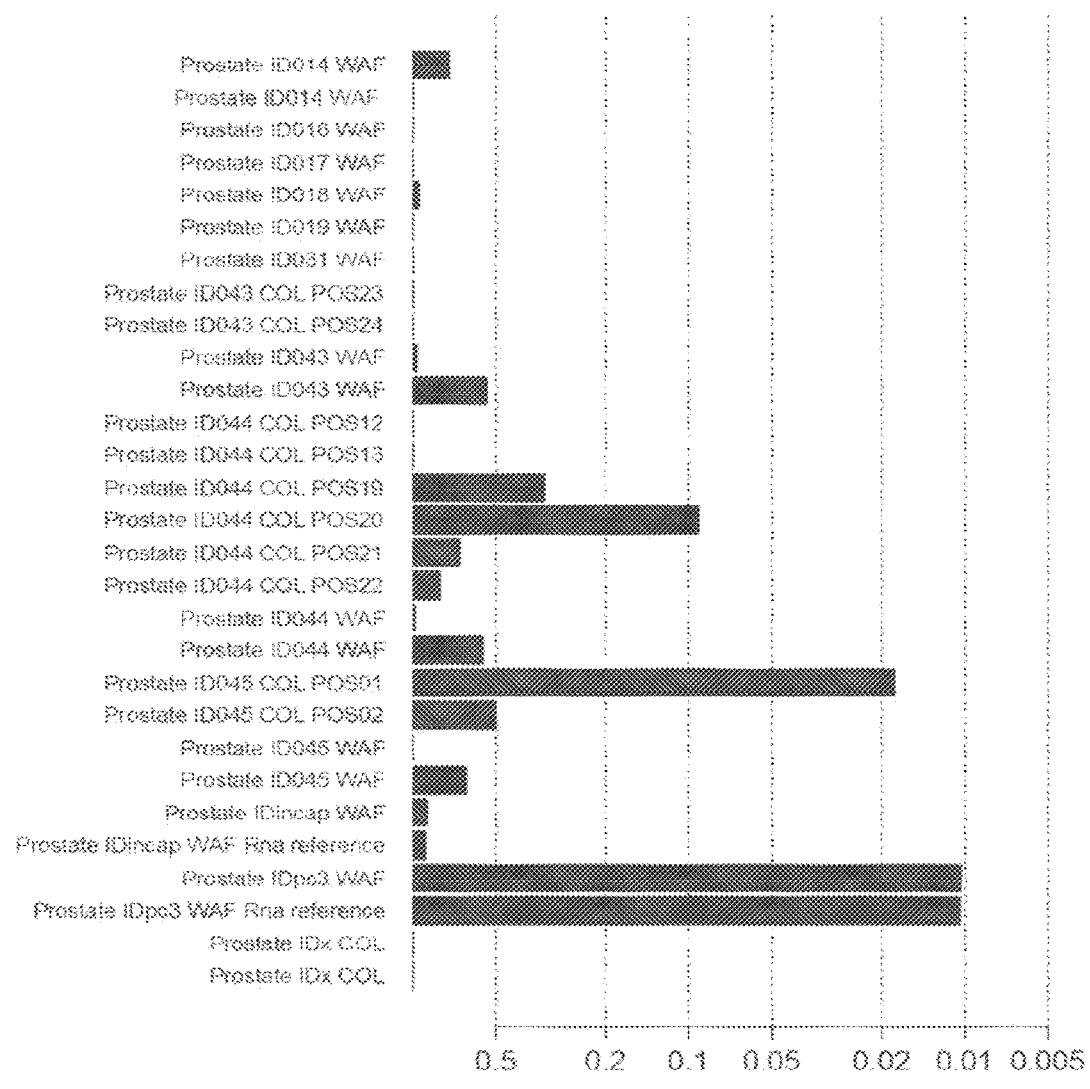
FIG. 8 displays results of mRNA sequencing analysis for the Aurora A signaling pathway.
Figure 9:
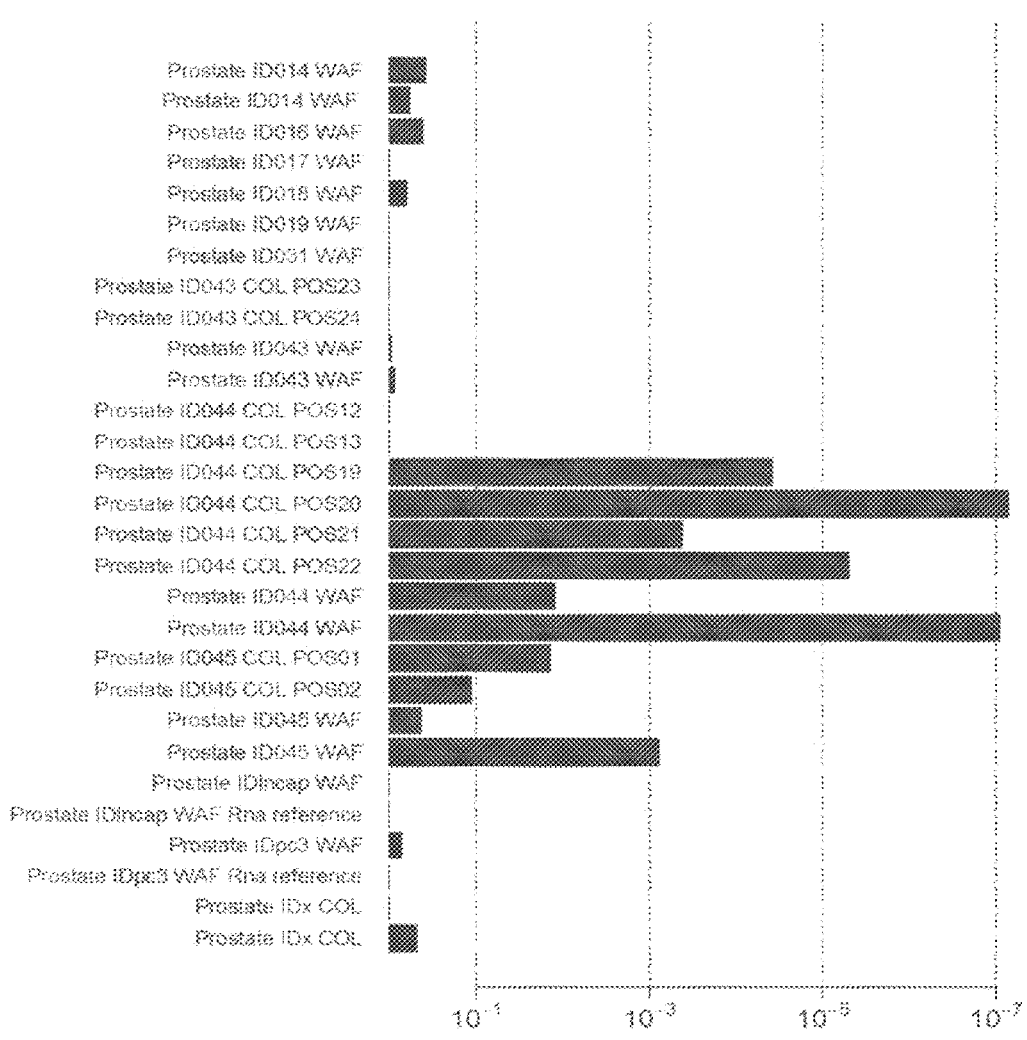
FIG. 9 displays results of mRNA sequencing analysis for the Kit receptor signaling pathway.

FIGS. 7-9 display results of a mRNA sequencing analysis to determine differential expression of specific signaling pathways among CTC colonies obtained from a sample of subjects. The CTC colonies were obtained using a method as described in FIGS. 2-3. The RNA sequence of the cells was mapped to specific genes, and the gene counts were normalized across a collection of samples. Using a non-parametric enrichment algorithm, statistical tests were performed to detect pathways associated with relatively high expression in each sample. False discovery rates were calculated across large collections of pathways. The enrichment test results were expressed as a false discovery rate on the x-axis for each prostate sample RNA profile as seen in FIGS. 7-9. The enrichment for gene expression in different pathways was different across the samples. Pathways that show enrichment in prostate CTC colonies included Nerve Growth Factor Receptor Signaling (FIG. 7), Aurora A Signaling (FIG. 8), and Kit Receptor Signaling (FIG. 9)

Example 4: EPCAM Expression of Pancreatic CTC Colonies

Figure 10:
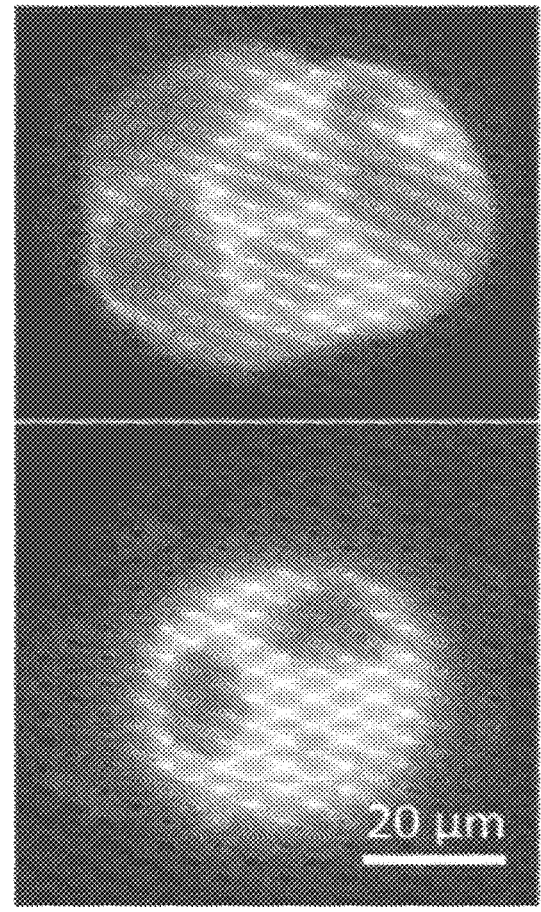
FIG. 10 is an immunofluorescence image for EPCAM expression in a PDAC CTC.
Figure 10:
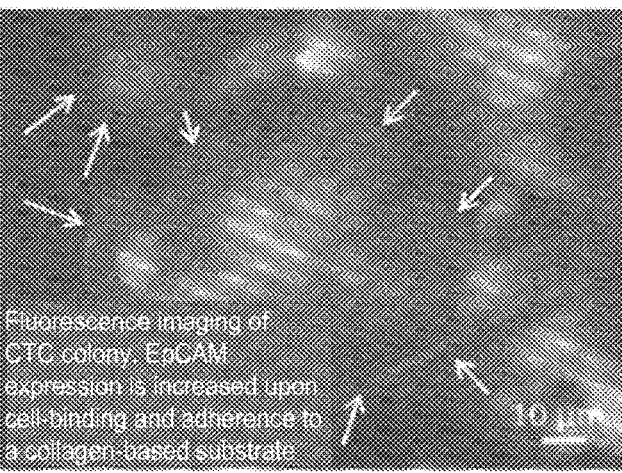

To determine EPCAM expression in pancreatic CTC colonies, 6 patients with pancreatic ductal adenocarcinoma (PDAC) were profiled. Apheresed blood samples were collected and cultured to yield CTC colonies. The cells were stained for cytokeratin 19 (CK19; top left panel, and circular staining in right panel) and EPCAM (punctate staining around cell in bottom left panel, and peripheral staining indicated by white arrows in right panel) as shown in FIG. 10. Cell binding to the collagen-based substrate used for culturing of the CTCs led to increased expression of EPCAM.

Example 5: Mutations Exhibited by Pancreatic CTC Colonies

Six pancreatic CTC colony samples were analyzed for mutations found in pancreatic cancer as determined from the COSMIC (Catalogue of Somatic Mutations in Cancer) database. In the COSMIC database for PDAC tumors, the mutation rate in KRAS is 69%, p53 is 51%, cyclin-dependent kinase inhibitor 2A (CDKN2A) is 23%, SMAD4 is 21%, AT-rich interactive domain-containing protein 1A (ARID1A) is 6%, and beta-catenin (CTNNB1) is 2%. For CTC colonies obtained after culturing, 2/6 of the colonies displayed mutations in KRAS, and 1/6 colonies displayed mutations in p53, CDK2NA, and CTNNB1.

Example 6: Gene Expression in Pancreatic and mCRPC CTC Colonies

Figure 11:
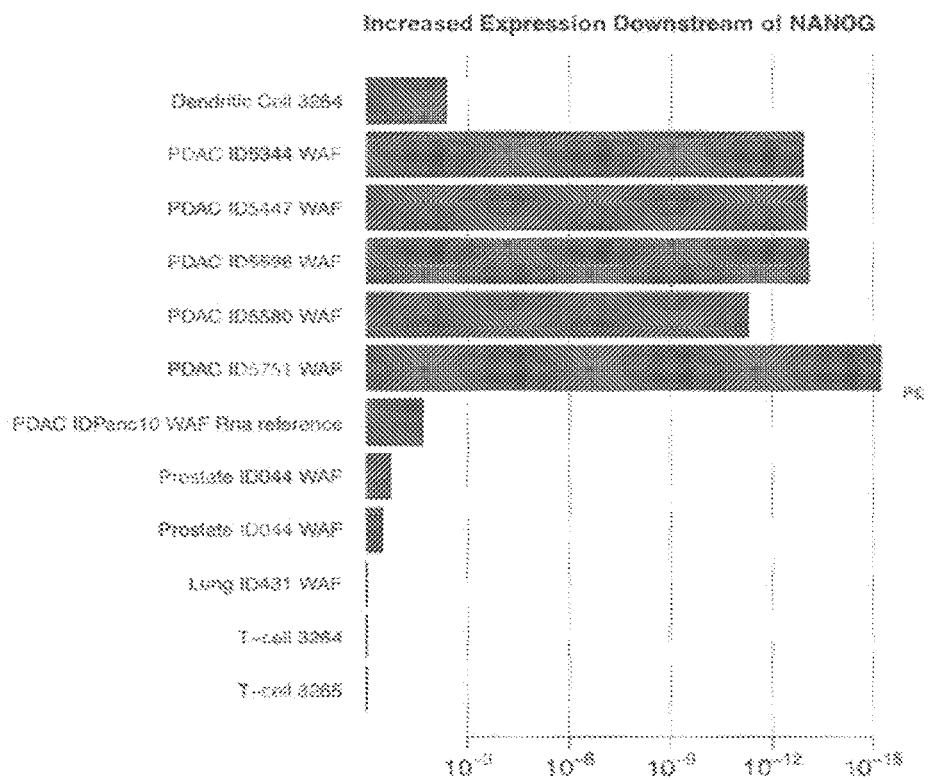
FIG. 11 depicts results of NANOG signaling pathway expression in PDAC versus mCRPC CTCs.
Figure 12:
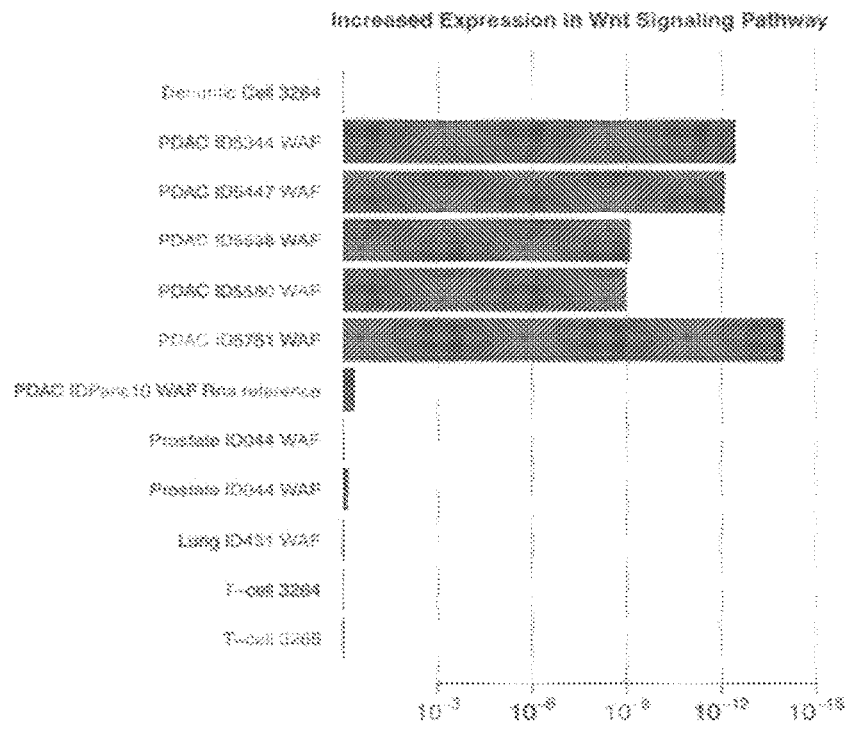
FIG. 12 depicts results of Wnt signaling pathway expression in PDAC versus mCRPC CTCs.

To determine whether there was differential expression between CTCs obtained from different tumors, PDAC CTCs were compared to mCRPC CTCs. Pancreatic CTCs exhibited increased gene expression in the NANOG, Wnt, insulin-like growth factor 1 (IGFR1), FOXP1, and AR signaling pathways. The RNA sequence of the cells was mapped to specific genes, and the gene counts were normalized across a collection of samples. Using a non-parametric enrichment algorithm, statistical tests were performed to detect pathways associated with relatively high expression in each sample. False discovery rates were calculated across large collections of pathways. The enrichment test results were expressed as a false discovery rate on the x-axis for each prostate sample RNA profile as seen in FIGS. 11-12. The enrichment for gene expression in different pathways was different across the samples. Pathways that show enrichment in pancreatic CTC colonies over prostate cancer CTCs included the NANOG signaling pathway (FIG. 11) and the Wnt signaling pathway (FIG. 12). Dendritic cells, lung and T-cells were used as controls, and the rest of the samples were CTCs obtained from the subjects.

Example 7: SNP/INDEL Variant Analysis

Figure 13:
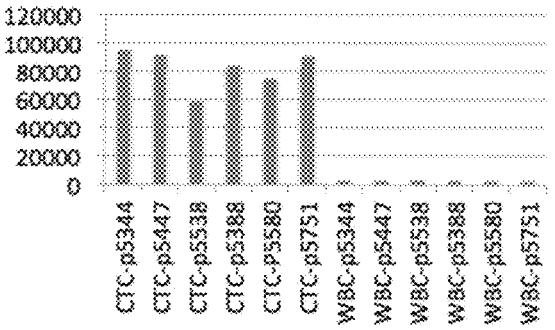
FIG. 13 displays results of SNP and INDEL analysis for CTCs.
Figure 13:
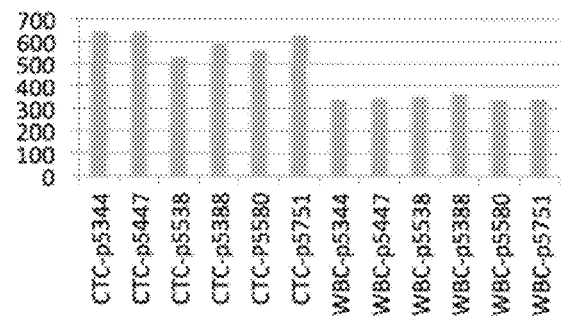

To determine if CTC fractions displayed more genetic variation than whole blood cell controls, single nucleotide polymorphisms (SNPs) and insertions/deletions (INDELs) were analyzed for six patients with stage 4 PDAC. FIG. 13 depicts the results of SNP and INDEL analysis and indicates that both in terms of total events (left panel) and total number of genes with events (right panel), the CTC samples were able to uncover more genetic variants compared to whole blood cell controls.

Figure 14:
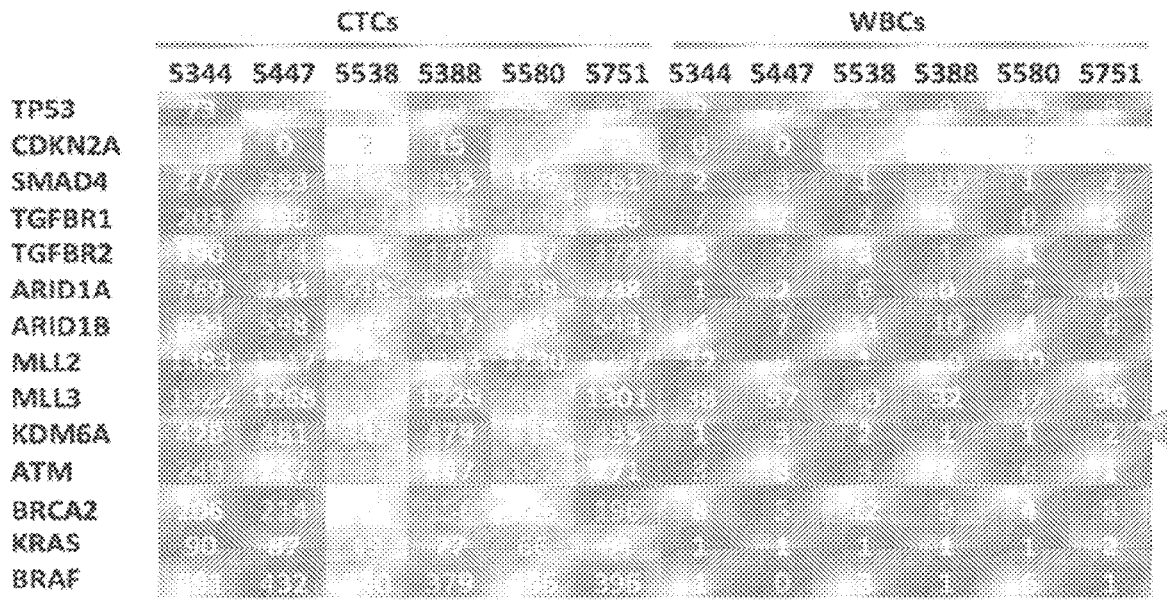
FIG. 14 displays results of SNP and INDEL analysis for CTCs.

Using a targeted sequencing method, patient samples were assessed for 238 genes associated with PDAC. FIG. 14 illustrates the results of the sequencing analysis and shows that CTCs (left side) revealed about 20-30 times more SNPs and INDELs compared to whole blood cell controls for specific genes. The numbers at the top of the chart denote the patient from which the sample was obtained.

Example 8: User Interfaces for Displays in a System of the Invention

Figure 15:
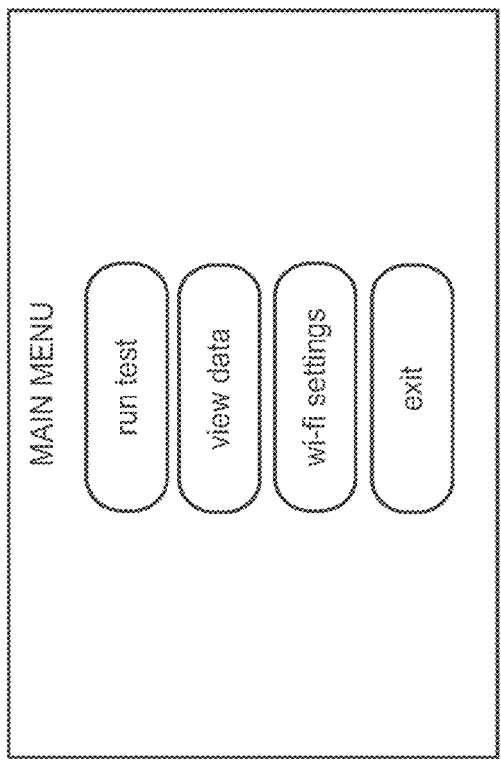
FIG. 15 depicts an illustrative user interface for a system of the invention.
Figure 15:
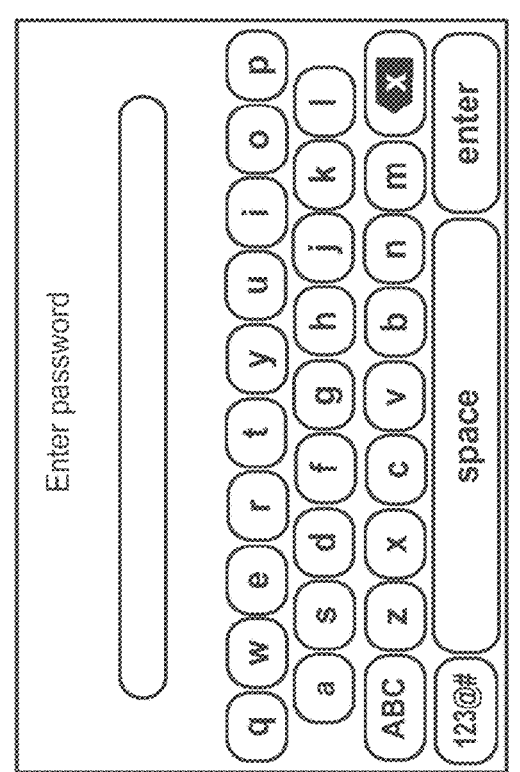
Figure 15:
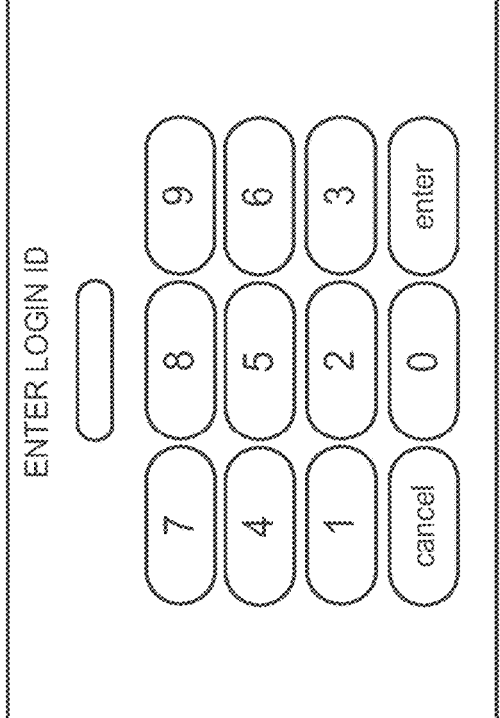
Figure 15:
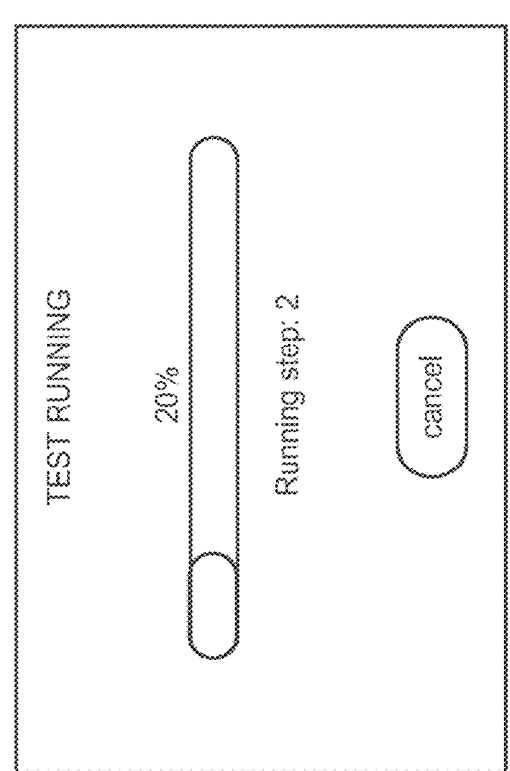

FIG. 15 depicts a graphical interface that is seen by the user upon initialization of a system of the invention. In the top-left corner, the user enters his/her user identification code. In the top-right corner, the user selects the desired option. The quadrant at the bottom-left corner indicates the progress of the desired operation. The bottom-right corner allows the user to enter his/her password for the system. FIG. 16 depicts an additional user interface that can be displayed by a system of the invention upon logging into the system. The user interface of FIG. 16 can be configured to be displayed, for example, for a minimum duration of time, until the hardware connectivity is verified, and until the user hits the start button.

FIG. 17 is a screen displaying the status of the oxygen level (%), chamber pressure (PSI), temperature (° C.), and carbon dioxide level (%) in the culture chamber. The screen further displays the relative humidity and experiment time remaining. The user can further enter alarm settings and time settings using the icons at the bottom of the screen. In this scenario, the oxygen level was 20.0%, the chamber pressure was 3.7 PSIG, the temperature was 34.2° C., and the carbon dioxide level was 6.3%. The relative humidity was 90%, and the experiment time remaining was 2 hours 38 minutes and 20 seconds.

FIG. 18 shows that upon selection of a specific parameter, the user can touch the arrows and decrease or increase the parameter to a desired value. The user can tap the arrow to change the value in small increments, or hold down the arrow to change the value at larger increments. Once the user has reached the desired value, the user touches the value, and the desired value becomes confirmed.

Example 9: Coating Process for Cell Adhesion

To prepare a surface for covalent binding of cellular proteins, glass slides were prepared by incubating the slides with 0.1 M hydrochloric acid (HCl) for two hours to overnight at room temperature. Then, the glass slides were incubated with 0.1 M NaOH for two hours to overnight at room temperature. The slides were then incubated with 0.5-5% (3-aminopropyl)-trimethoxysilane for two hours to overnight at room temperature. Then, the slides were incubated with 0.5-5% glutaraldehyde (diluted in PBS) for 2 hours to overnight at room temperature. The glass slides were then rinsed with water overnight, sterilized under UV light for one hour, and then stored dry at room temperature.

The slides were then further treated to facilitate cell binding using a mixture containing extracellular matrix (ECM) proteins. The ECM mix contained from about 0.1 to about 3 mg/mL collagen, from about 0.1 to about 10 µg/mL fibronectin, and from about 0.1 to about 10 µg/mL of a basement membrane cocktail. The ECM mix was diluted with either a glycine buffer at pH 10 or a DMEM buffer at pH 7 depending on the cellular application.

Example 10: Transfection Efficiency Using a Method of the Invention

Figure 23:
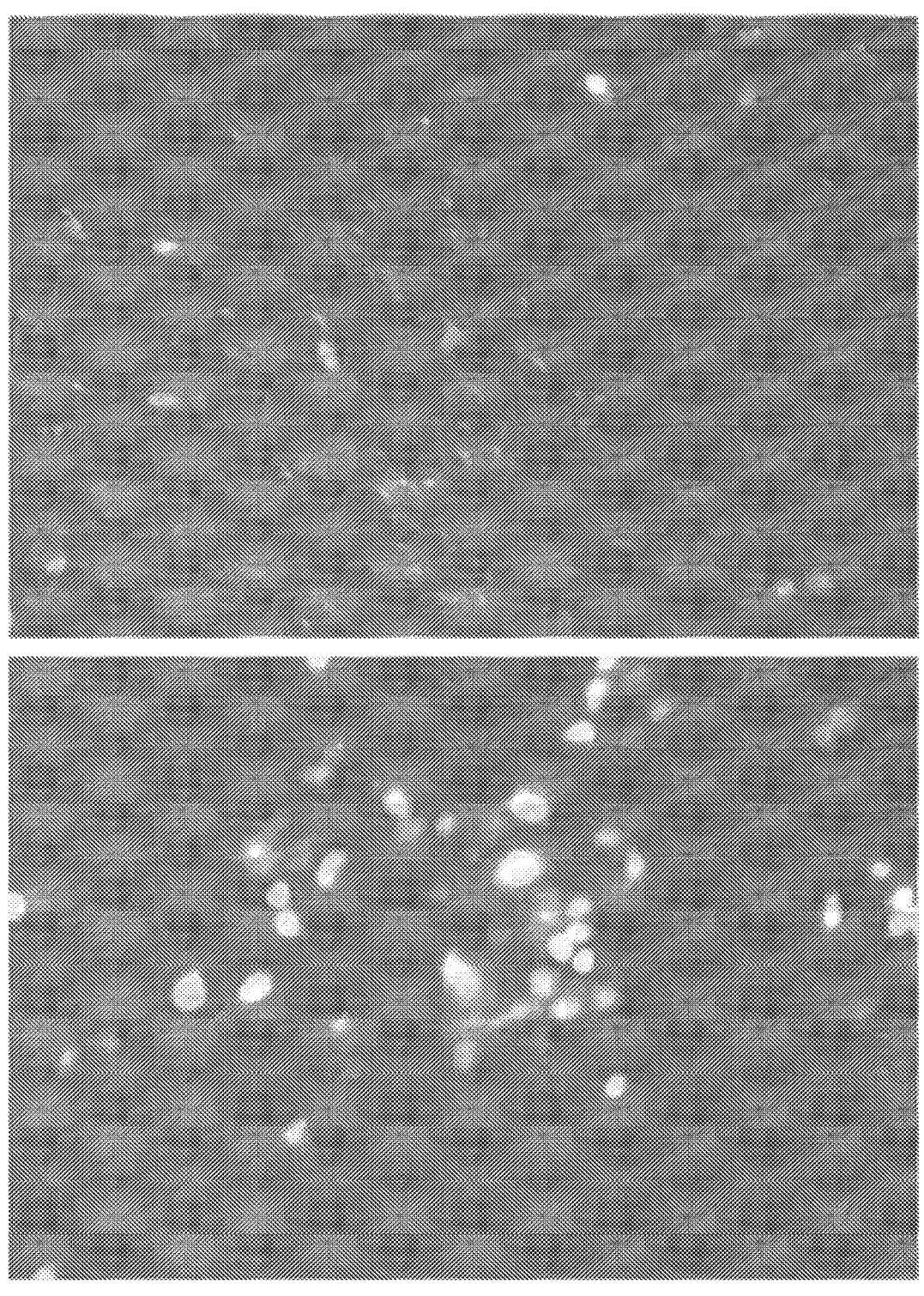
FIG. 23 depicts increased cellular transfection efficiency using green fluorescent protein.

DU145 (human prostate cancer) cells were transfected with a GFP plasmid using electroporation. $5 \times 10^6$ cells/mL were electroporated using a protocol of 1260 V for 20 ms twice with 50 ng DNA plasmid/μL of the cell resuspension. After transfection, the cells were split into separate 35 mm cell culture plates. One plate was placed in a standard CO2 incubator, and the other plate was place in an incubator of the invention. The second plate's incubator was set to 1% O2 and 2 PSIG. After 48 hours, the cells were fixed and imaged for GFP expression using a fluorescent microscope. The data shown in FIG. 23 indicate that cells incubated at low oxygen and high pressure showed higher transfection efficiency (lower panel) than those cells incubated at standard conditions (upper panel) as depicted by a greater number of bright cells.

EMBODIMENTS

The following non-limiting embodiments provide illustrative examples of the invention, but do not limit the scope of the invention.

Embodiment 1. A cell culture incubator, wherein the cell culture incubator comprises: a) an enclosed environmental chamber; and b) a control unit, wherein the control unit is operably linked to the enclosed environmental chamber, wherein the control unit comprises a computer program product comprising a computer-readable medium having computer-executable code encoded therein, the computer-executable code adapted to encode: (i) an oxygen level module, wherein the oxygen level module is encoded to regulate an oxygen level of the enclosed environmental chamber, wherein the oxygen level module is encoded to control the removal of oxygen in the enclosed environmental chamber to generate a hypoxic oxygen level within the enclosed environmental chamber; (ii) a pressure module, wherein the pressure module is encoded to regulate a pressure of the enclosed environmental chamber, wherein the pressure module controls the addition of gas to generate a positive pressure condition in the enclosed environmental chamber; (iii) a temperature module, wherein the temperature module is encoded to regulate a temperature of the enclosed environmental chamber; and (iv) a humidity module, wherein the humidity module is encoded to regulate a humidity of the enclosed environmental chamber, wherein each of the oxygen level, pressure, temperature, and humidity mimics an in vivo microenvironment for a cell, wherein the cell culture incubator reaches each of an instructed oxygen level, pressure, temperature, and humidity within about 20 minutes of receiving an input of each of the instructed oxygen level, pressure, temperature, and humidity.

Embodiment 2. The cell culture incubator of embodiment 1, wherein the in vivo microenvironment is a tumor microenvironment.

Embodiment 3. The cell culture incubator of any one of embodiments 1-2, wherein the cell is a stem cell.

Embodiment 4. The cell culture incubator of any one of embodiments 1-2, wherein the cell is a cancer cell.

Embodiment 5. The cell culture incubator of any one of embodiments 1-2, wherein the cell is a circulating tumor cell.

Embodiment 6. The cell culture incubator of any one of embodiments 1-2, wherein the cell is an immune cell.

Embodiment 7. The cell culture incubator of any one of embodiments 1-6, wherein the cell is obtained from a biological sample.

Embodiment 8. The cell culture incubator of embodiment 7, wherein the biological sample is blood.

Embodiment 9. The cell culture incubator of embodiment 7, wherein the biological sample is a tumor.

Embodiment 10. The cell culture incubator of embodiment 7, wherein the biological sample is saliva.

Embodiment 11. The cell culture incubator of embodiment 7, wherein the biological sample is a tissue.

Embodiment 12. The cell culture incubator of any one of embodiments 1-11, wherein the control unit is user-controlled.

Embodiment 13. The cell culture incubator of any one of embodiments 1-11, wherein the control unit is automated.

Embodiment 14. The cell culture incubator of any one of embodiments 1-13, wherein the oxygen module is encoded to maintain a hypoxic oxygen level.

Embodiment 15. The cell culture incubator of any one of embodiments 1-14, wherein the pressure module is encoded to maintain a positive pressure condition.

Embodiment 16. The cell culture incubator of any one of embodiments 1-15, wherein the oxygen level module is encoded to maintain the oxygen level in the enclosed environmental chamber at about 0.1% to about 21%.

Embodiment 17. The cell culture incubator of any one of embodiments 1-16, wherein the oxygen level module is encoded to maintain the oxygen level in the enclosed environmental chamber at about 2%.

Embodiment 18. The cell culture incubator of any one of embodiments 1-17, wherein the oxygen level module is encoded to maintain the oxygen level in the enclosed environmental chamber at about 0.1%.

Embodiment 19. The cell culture incubator of any one of embodiments 1-18, wherein the pressure module is encoded to maintain the pressure in the enclosed environmental chamber at from about 1 PSIG to about 5 PSIG.

Embodiment 20. The cell culture incubator of any one of embodiments 1-19, wherein the humidity module is encoded to maintain the humidity in the enclosed environmental chamber at about 85%.

Embodiment 21. The cell culture incubator of any one of embodiments 1-20, wherein the control unit further comprises a computer program product comprising a computer-readable medium having computer-executable code encoded therein, the computer-executable code adapted to encode a carbon dioxide module, wherein the carbon dioxide module is encoded to regulate a carbon dioxide level of the enclosed environmental chamber.

Embodiment 22. The cell culture incubator of any one of embodiments 1-21, wherein the cell culture incubator further comprises a gas inlet controlled by the oxygen level module.

Embodiment 23. The cell culture incubator of any one of embodiments 1-22, wherein the cell culture incubator further comprises a gas inlet controlled by the pressure module.

Embodiment 24. The cell culture incubator of any one of embodiments 1-23, wherein the cell culture incubator further comprises a water humidity tray controlled by the humidity module.

Embodiment 25. The cell culture incubator of any one of embodiments 1-24, wherein the cell culture incubator further comprises a heating element controlled by the temperature module.

Embodiment 26. The cell culture incubator of any one of embodiments 1-25, wherein the cell culture incubator is configured to accept a cell culture plate.

Any one or more features of any embodiment of the inventions disclosed herein may be combined with any one or more other features of any other embodiment of the inventions, without departing from the scope of the invention. It should also be understood that while some theoretical considerations may have been provided to further an understanding of embodiments of the invention, the claims to the invention are not bound by such theory. It should also be understood that the invention is not limited to the embodiments that are described or depicted herein for purposes of exemplification, but is to be defined only by a fair reading of claims appended to the patent application, including the full range of equivalency to which each element thereof is entitled.

What is claimed is:

1. A non-transitory computer readable storage medium storing a program for operating a cell culture incubator system using a controller, wherein the program operates the system by:

a. sensing a chamber oxygen level in an enclosed environmental chamber with an oxygen sensor that is electrically coupled to the controller;

b. sensing a total gas pressure in the enclosed environmental chamber with a pressure sensor that is electrically coupled to the controller;

c. providing instructions to the controller to regulate the enclosed environmental chamber oxygen level to a set oxygen level within a range of 0.1% to 12% oxygen;

d. providing instructions to the controller to regulate the total gas pressure to a set positive pressure level within 0.1-0.5 psi;

e. regulating the enclosed environmental chamber oxygen level to the set oxygen level;

f. regulating the total gas pressure to the set positive pressure level; and g. maintaining the enclosed environmental chamber oxygen level to the set oxygen level within a range of 0.1% to 12% oxygen and maintaining the total gas pressure to the set positive pressure level within 0.1-0.5 psi, wherein the set oxygen level is controlled by a first sensor the first sensor consisting of the oxygen sensor and the set positive pressure level is controlled by a second sensor the second sensor consisting of the pressure sensor, and wherein the instructed set oxygen level prevails despite the oxygen partial pressure-increasing effect of the positive pressure condition associated with the instructed positive pressure level.

2. The non-transitory computer readable storage medium of claim 1, wherein regulating the total gas pressure further comprises the controller opening a valve connecting the chamber to a nitrogen source, permitting a flow of nitrogen into the chamber, wherein the valve is electrically coupled to the controller.

3. The non-transitory computer readable storage medium of claim 1, wherein, when the pressure sensor senses the total gas pressure less to be less than the set positive pressure level, regulating the total gas pressure to the set positive pressure level further comprises:

a. providing instructions to the controller to regulate the total gas pressure to the set positive pressure level, wherein the controller opens a valve connecting the chamber to a nitrogen source to permit a flow of nitrogen into the chamber, wherein the valve is electrically coupled to the controller.

4. The non-transitory computer readable storage medium of claim 3, further comprising the controller providing instructions to the valve connecting the chamber to a nitrogen source to permit a flow of nitrogen into the chamber.

5. The non-transitory computer readable storage medium of claim 1, wherein, when the pressure sensor senses the total gas pressure to be greater than the set positive pressure level, maintaining the total gas pressure to the set positive pressure level further comprises releasing gas from the chamber using a vent efflux to reduce the total gas pressure in the chamber.

6. The non-transitory computer readable storage medium of claim 1, wherein providing instructions to the controller to regulate the total gas pressure to the set positive pressure level comprises the program providing instructions to the controller to adjust the set positive pressure level to a value within a range of about 0.5 PSIG to about 30 PSIG.

7. The non-transitory computer readable storage medium of claim 1, wherein providing instructions to the controller to regulate the total gas pressure to a set positive pressure level comprises the program providing instructions to the controller to adjust the set positive pressure level to a value within a range of about 1.0 PSIG to about 20 PSIG.

8. The non-transitory computer readable storage medium of claim 1, wherein providing instructions to the controller to regulate the total gas pressure to a set positive pressure level comprises the program providing instructions to the controller to adjust the set positive pressure level to a value within a range of about 2.0 PSIG to about 10 PSIG.

9. The non-transitory computer readable storage medium of claim 1, wherein providing instructions to the controller to regulate the total gas pressure to a set positive pressure level comprises the program providing instructions to the controller to adjust the set positive pressure level to a value within a range of about 2.5 PSIG to about 5.0 PSIG.

10. The non-transitory computer readable storage medium of claim 1, wherein, when the oxygen sensor senses sensing the chamber oxygen level to be above the set oxygen level, regulating the chamber oxygen level further comprises opening a valve connecting the chamber to a nitrogen source, and permitting a flow of nitrogen into the chamber to dilute the chamber oxygen level, wherein the valve is electrically coupled to the controller.

11. The non-transitory computer readable storage medium of claim 1, wherein maintaining the chamber oxygen level to the set oxygen level further comprises:

a. sensing the chamber oxygen level in the chamber to be above the set oxygen level;

b. regulating the chamber oxygen level by opening a valve connecting the chamber to a nitrogen source, and permitting a flow of nitrogen into the chamber, wherein the valve is electrically coupled to the controller;

c. sensing the chamber oxygen level to be at the set oxygen level as a result of a dilution of oxygen in the chamber by the flow of nitrogen; and d. ceasing the flow of nitrogen by closing the valve.

12. The non-transitory computer readable storage medium of claim 1, wherein maintaining the chamber oxygen level to the set oxygen level further comprises:

a. sensing the chamber oxygen level in the chamber to be below the set oxygen level; and b. regulating the chamber oxygen level by pumping atmospheric air using an air injection pump into the chamber to increase the chamber oxygen level, wherein the air injection pump is electrically coupled to the controller.

13. The non-transitory computer readable storage medium of claim 12, further comprising the controller providing instructions to a valve connecting the chamber to a nitrogen source, to permit a flow of nitrogen into the chamber.

14. The non-transitory computer readable storage medium of claim 12, wherein maintaining the chamber oxygen level to the set level despite an oxygen partial pressure increasing effect of a positive pressure condition resulting from the set positive pressure level further comprises:

a. sensing the total gas pressure in the chamber to be above the set positive pressure level;

b. releasing gas from the chamber using a vent efflux to reduce the total gas pressure in the chamber;

c. sensing the chamber oxygen level to be above the set oxygen level;

d. regulating the chamber oxygen level by opening a valve connecting the chamber to a nitrogen source, and permitting a flow of nitrogen into the chamber;

e. sensing the chamber oxygen level to be at the set oxygen level as a result of a dilution of oxygen in the chamber by the flow of nitrogen;

f. ceasing the flow of nitrogen by closing the valve; and g. repeating steps a-f until the oxygen sensor senses to chamber oxygen level to be at the set oxygen level, and the pressure sensor senses the total gas pressure to be within a specified range of the set positive pressure level.

15. The non-transitory computer readable storage medium of claim 1, wherein when the oxygen sensor senses the chamber oxygen level above the oxygen set level, regulating the chamber oxygen level to the set oxygen level further comprises:

a. providing instructions to the controller to regulate the chamber oxygen level to the set oxygen level, wherein the controller opens a valve connecting the chamber to a nitrogen source and permits a flow of nitrogen into the chamber, wherein the valve is electrically coupled to the controller.

16. The non-transitory computer readable storage medium of claim 1, wherein providing instructions to the controller to regulate the chamber oxygen level to the set oxygen level comprises instructions to adjust the chamber oxygen level to a value within a range of about 2.0% to about 6% oxygen.

17. The non-transitory computer readable storage medium of claim 1, further comprising maintaining the total gas pressure to the set positive pressure level by:

a. sensing the total gas pressure in the chamber is below the set positive pressure level;

b. regulating the total gas pressure by opening a valve connecting the chamber to a nitrogen source, and permitting a flow of nitrogen into the chamber;

c. sensing the total gas pressure is at the set positive pressure level as a result of the flow of nitrogen; and d. ceasing the flow of nitrogen by closing the valve.

18. The non-transitory computer readable storage medium of claim 1, further comprising:

a. sensing a chamber carbon dioxide level in the enclosed environmental chamber with a carbon dioxide sensor that is electrically coupled to the controller;

b. providing instructions to the controller to regulate the chamber carbon dioxide level to a set carbon dioxide level;

c. regulating the chamber carbon dioxide level by opening a valve connecting the chamber to a carbon dioxide source, and permitting a flow of carbon dioxide into the chamber; and d. maintaining the chamber carbon dioxide level.

19. The non-transitory computer readable storage medium of claim 18, wherein maintaining the carbon dioxide to the set carbon dioxide level further comprises a. sensing the chamber carbon dioxide level in the chamber is above the set carbon dioxide level;

b. regulating the chamber carbon dioxide level by opening a valve connecting the chamber to a carbon dioxide source, and permitting a flow of carbon dioxide into the chamber;

c. sensing the chamber carbon dioxide level is at the set carbon dioxide level as a result of the flow of carbon dioxide; and d. ceasing the flow of carbon dioxide by closing the valve.

20. The non-transitory computer readable storage medium of claim 1, wherein the controller is a computer.

21. The non-transitory computer readable storage medium of claim 1, wherein the controller comprises a server; a central processing unit; a memory drive; and a network adapter.

22. The non-transitory computer readable storage medium of claim 1, wherein the controller comprises a central processing unit; a memory drive; and a network adapter, and wherein the controller is in communication with a remote computer server storing and executing the non-transitory computer readable storage medium.

23. The non-transitory computer readable storage medium of claim 1, wherein step b is performed prior to step a.

24. The non-transitory computer readable storage medium of claim 1, wherein step d is performed prior to step c.

25. The non-transitory computer readable storage medium of claim 1, wherein steps c-d are performed prior to steps a-b.

26. The non-transitory computer readable storage medium of claim 1, wherein maintaining the chamber oxygen level to the set oxygen level comprises regulating a composition of gases in the enclosed environmental chamber such that (1) when the oxygen sensor senses the chamber oxygen level to be below the set oxygen level, regulating the oxygen level comprises injecting air into the enclosed chamber, and (2) when the oxygen sensor senses the chamber oxygen level to be above the set oxygen level, regulating the chamber oxygen level comprises injecting nitrogen into the enclosed chamber, wherein both injecting air and injecting nitrogen in response to the sensed oxygen signal occur independently of a sensed total gas pressure level.

27. The non-transitory computer readable storage medium of claim 1, wherein maintaining the total gas pressure to the set positive pressure level comprises regulating the total gas pressure such that (1) when the pressure sensor senses the total gas pressure to be below the set positive pressure level, regulating the total gas pressure comprises injecting nitrogen into the enclosed chamber, and (2) when the pressure sensor senses the total gas pressure to be above the set positive pressure level, regulating the total gas pressure comprises releasing gas from the enclosed chamber by way of a vent efflux, wherein both injecting nitrogen and releasing gas occur independently of a sensed oxygen level.

* * * * *